US007867629B2

(12) United States Patent
Yamamoto et al.

(10) Patent No.: US 7,867,629 B2
(45) Date of Patent: Jan. 11, 2011

(54) NITROGENOUS HETEROCYCLIC DERIVATIVE AND ORGANIC ELECTROLUMINESCENT ELEMENT EMPLOYING THE SAME

(75) Inventors: Hiroshi Yamamoto, Chiba (JP); Masahide Matsuura, Chiba (JP); Hidetsugu Ikeda, Chiba (JP); Mineyuki Kubota, Chiba (JP); Masahiro Kawamura, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 713 days.

(21) Appl. No.: 10/541,745

(22) PCT Filed: Sep. 26, 2003

(86) PCT No.: PCT/JP03/12322

§ 371 (c)(1), (2), (4) Date: Jul. 8, 2005

(87) PCT Pub. No.: WO2004/063159

PCT Pub. Date: Jul. 29, 2004

(65) Prior Publication Data

US 2006/0154105 A1 Jul. 13, 2006

(30) Foreign Application Priority Data

Jan. 10, 2003 (JP) ............................ 2003-004139
Jan. 14, 2003 (JP) ............................ 2003-005184

(51) Int. Cl.
*H01L 51/54* (2006.01)
*C09K 11/00* (2006.01)

(52) U.S. Cl. ....................... 428/690; 428/917; 313/504; 313/506; 252/301.16; 257/40; 257/103; 548/303.1; 548/303.4; 548/302.7; 544/180; 544/182; 544/224; 544/242

(58) Field of Classification Search ................. 546/121; 428/690, 917; 427/58, 66; 313/502–509; 257/40, 88–103, E51.001–E51.052; 252/301.16–301.35; 548/303.1, 303.4, 304.4
See application file for complete search history.

(56) References Cited

U.S. PATENT DOCUMENTS

| | | | | |
|---|---|---|---|---|
| 4,965,302 | A | 10/1990 | Hirahara et al. | 524/83 |
| 5,077,142 | A | 12/1991 | Sakon et al. | 428/690 |
| 6,013,384 | A * | 1/2000 | Kido et al. | 428/690 |
| 6,461,747 | B1 | 10/2002 | Okada et al. | 428/690 |
| 6,998,487 | B2 * | 2/2006 | Kim et al. | 546/15 |
| 2002/0048687 | A1 * | 4/2002 | Hosokawa et al. | 428/690 |
| 2006/0147747 | A1 * | 7/2006 | Yamamoto et al. | 428/690 |
| 2006/0154105 | A1 | 7/2006 | Yamamoto et al. | 428/690 |
| 2007/0138950 | A1 * | 6/2007 | Yamamoto et al. | 313/504 |
| 2007/0200490 | A1 * | 8/2007 | Kawamura et al. | 313/504 |
| 2007/0267970 | A1 * | 11/2007 | Yamamoto et al. | 313/506 |

FOREIGN PATENT DOCUMENTS

| | | |
|---|---|---|
| EP | 786926 | 7/1997 |
| EP | 1061112 | 12/2000 |
| EP | 1167488 | 1/2002 |
| EP | 1221434 | 7/2002 |
| EP | 1549112 | 6/2005 |
| EP | 1551206 | 7/2005 |
| GB | 2351081 | * 12/2000 |
| JP | 10-152676 | 6/1988 |
| JP | 07-109413 | 4/1995 |
| JP | 08101520 | 4/1996 |
| JP | 11-111458 | 4/1999 |
| JP | 11-329732 | 11/1999 |
| JP | 2001-6877 | 1/2001 |
| JP | 2001-35664 | 2/2001 |
| JP | 2001-43978 | 2/2001 |
| JP | 2001-110572 | 4/2001 |
| JP | 2001-223082 | 8/2001 |
| JP | 2001335776 | * 12/2001 |
| JP | 2002-038141 A | * 2/2002 |
| JP | 2002-235075 | 8/2002 |
| JP | 2002-265938 | 9/2002 |
| JP | 2003-109763 | 4/2003 |
| JP | 2003-109765 | 4/2003 |
| JP | 2003-128651 | 5/2003 |
| JP | 2003-229273 | 8/2003 |
| JP | 2003-238534 | 8/2003 |
| JP | 2003-277743 | 10/2003 |
| JP | 2003-282270 | 10/2003 |

(Continued)

OTHER PUBLICATIONS

Machine Translation of JP 2001-035664 (2001).*

(Continued)

*Primary Examiner*—D. Lawrence Tarazano
*Assistant Examiner*—Michael Wilson
(74) *Attorney, Agent, or Firm*—Steptoe & Johnson LLP

(57) ABSTRACT

A specific derivative of heterocyclic compound having nitrogen atom and an organic electroluminescence device comprising the compound. An organic electroluminescence device comprising at least one of organic compound layers including a light emitting layer sandwiched between an anode and a cathode, wherein said at least one of the organic compound layers comprises the derivative of the heterocyclic compound having nitrogen atom as a sole component or as mixed component. The organic electroluminescence device achieves elevation of luminance and excellent efficiency of light emission, and also achieves long lifetime by an improvement of an electrode adhesion.

12 Claims, No Drawings

FOREIGN PATENT DOCUMENTS

| | | |
|---|---|---|
| WO | WO 00/78726 | 12/2000 |
| WO | WO 01/19815 | 3/2001 |
| WO | WO 02/088274 | 11/2002 |
| WO | WO 02/100977 | 12/2002 |
| WO | WO 03/078541 | 9/2003 |
| WO | WO 2004/003079 | 1/2004 |

OTHER PUBLICATIONS

English machine translation of JP 2002-038141 A.*

English machine translation of JP 2002-038141 A, 2002.*

Han, X. et al, "The isoxazole as a linchpin for molecules that target folded DNA conformations: selective lateral lithiation and palladation," Tetrahedron Letters, 2002, vol. 43, No. 43, pp. 7673-7677.

Aoyama, Y. et al, "Crystal Engineering of Stacked Aromatic Columns. Three-Dimensional Control of the Alignment of Orthogonal Aromatic Triads and Guest Quinones via Self-Assembly of Hydrogen-Bonded Networks," Journal of the American Chemical Society, 1966, vol. 118, No. 24, pp. 5562-5571.

Dodge, J. et al, "Regioselective synthesis of substituted rubrenes," Journal of Organic Chemistry, 1990, vol. 55, No. 13, pp. 4190-4198.

Forrester, A. et al, "Iminyls. Part 4. Intramolecular abstraction of benzylic hydrogen by diaryliminyls," Journal of the Chemical Society, Perkin Transactions 1: Organic and Bio-Organic Chemistry (1972-1999), 1979, No. 3, pp. 621-631.

Puchov, V. et al, "Transformation in the series of diazoamino compounds. II. Thermal decomposition of substituted anthraquinonylphenyl-1,3-triazenes," Zhurnal Obshchej Khimii, 1959, vol. 29, pp. 3058-3064.

Contour-Galcéra, M. et al, "Synthesis of Substituted Imidazopyrazines as Ligands for the Human Somatostatin Receptor Subtype 5," Bioorganic & Medicinal Chemistry Letters, Mar. 8, 2001, vol. 11, No. 5, pp. 741-745.

* cited by examiner

NITROGENOUS HETEROCYCLIC DERIVATIVE AND ORGANIC ELECTROLUMINESCENT ELEMENT EMPLOYING THE SAME

The present application is based on International Application PCT/JP2003/012322, filed Sep. 26, 2003, which application is incorporated herein by reference in its entirety.

TECHNICAL FIELD

The present invention relates to a novel nitrogenous heterocyclic derivative, i.e., a novel derivative of heterocyclic compound having nitrogen atom and to an organic electroluminescent device (an electroluminescent device will be referred to as an electroluminescence device, hereinafter) which utilizes the novel compound. More particularly, the present invention relates to a derivative of heterocyclic compound having nitrogen atom useful as constituting component of an organic electroluminescence ("electroluminescence" will be occasionally referred to as "EL", hereinafter) device, i.e., an organic EL device achieving elevation of luminance and of efficiency in light emission even under low driving voltage, and also achieving long term stabilization by improvement of an electrode adhesion in accordance with an employment of the derivative of heterocyclic compound having nitrogen atom for at least one layer composing organic compound layers of the EL device.

BACKGROUND ART

An organic electroluminescence device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed among the light emitting layer can be enclosed.

As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

Conventionally, trials for raising efficiency of light emission of the organic EL device by providing an electron injecting/transporting layer have been repeated. In this case, there were drawbacks that formation of exciplex was found, and that lifetime of light emission was short in spite of obtaining highly illuminant light emission. Further, a long time electric drive caused separation between a metal-electrode and an organic compound or crystallization of the organic compound layer and the electrode resultantly whitening, further decreasing luminance of light emission, and it was necessary to prevent such a phenomena.

As the examples of heterocyclic compound having nitrogen atom such as pyrazine compound, quinoline compound, quinoxaline compound and so on employed as a constituting component of the organic EL device, there are 2,3,5,6-tetraphenyl pyrazine, 2,3,4-triphenyl quinoline and 2,3-diphenyl quinoxaline that are all disclosed in U.S. Pat. No. 5,077,142. However, because melting points of these compounds is low, there were disadvantages of such as inviting unfavorable fact such that even employing these compounds as amorphous thin-film layer of the organic EL device soon induces crystallization and disturbs light emission almost at all. Also, there were disadvantages that an electric drive caused the above separation, which made the lifetime short.

Furthermore, a blue-light-emitting device with the use of a heterocyclic compound having nitrogen atom is disclosed in Japanese Unexamined Patent Application Laid-Open No. 2001-6877, and an organic EL device with the use of a heterocyclic compound having nitrogen atom for a light emitting material or a hole injection transport material is disclosed in Japanese Unexamined Patent Application Laid-Open No. 2001-35664. The invention of Japanese Unexamined Patent Application Laid-Open No. 2001-6877 provides blue-light emission having peak wave-length in 430 to 480 nm, and the invention of Japanese Unexamined Patent Application Laid-Open No. 2001-35664 provides a luminance of about 500 $cd/m^2$ under the application of an electric voltage of 6 V when using the heterocyclic compound having nitrogen atom as hole injection material, and also provides a luminance of about 2300 $cd/m^2$ under the application of electric voltage of 12 V when using the compound as a light emitting material. However, the voltage was too high to keep practical performance and an organic EL device having excellent efficiency of light emission under the application of lower electric voltage was required.

DISCLOSURE OF THE INVENTION

The object of the present invention is to provide a novel derivative of heterocyclic compound having nitrogen atom useful as a constitutional component of an organic EL device. Another object of the present invention is to provide an organic EL device achieving elevation of luminance and of efficiency in light emission and also achieving long lifetime by improvement of an electrode adhesion in accordance with an employment of the derivative of heterocyclic compound having nitrogen atom for at least one layer composing organic compound layers of the EL device.

As a result of intensive researches and studies to achieve the above object by the present inventors, a derivative of heterocyclic compound having nitrogen atom was found to be a novel compound with specific structure useful as a material for an organic El device. Further, employing the compound as a component of at least one layer (in particular, electron injecting layer) in organic compound layers of an organic EL device was also found enabling to achieve elevation of luminance and of efficiency in light emission and also to achieve long lifetime by improvement of an electrode adhesion. Such being the case, the present invention has been accomplished on the basis of the foregoing findings and information.

Namely, the present invention provides a derivative of heterocyclic compound having nitrogen atom represented by any one of general formulae (1) and (1') to (3') below.

$$HAr\text{-}L\text{-}Ar^1\text{—}Ar^2 \quad (1)$$

wherein HAr represents a heterocyclic group having nitrogen atom, which has 3 to 40 carbon atoms and which may have a substituent;

L represents a single bond, an arylene group having 6 to 60 carbon atoms and may have a substituent, a heteroarylene group having 3 to 60 carbon atoms and may have a substituent or a fluorenylene group which may have a substituent;

$Ar^1$ represents a divalent aromatic hydrocarbon group having 6 to 60 carbon atoms and may have a substituent; and $Ar^2$ represents an aryl group having 6 to 60 carbon atoms and may have a substituent or a heteroaryl group having 3 to 60 carbon atoms and may have a substituent.

(1')

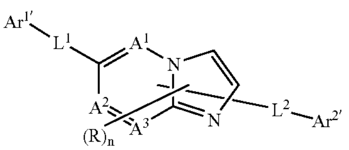

wherein $A^1$, $A^2$ and $A^3$ each independently represents nitrogen atom or carbon atom;

$Ar^{1'}$ represents a substituted or unsubstituted aryl group having 6 to 60 nuclear carbon atoms or a substituted or unsubstituted heteroaryl group having 3 to 60 nuclear carbon atoms; $Ar^{2'}$ represents a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms; or a substituted or unsubstituted alkoxy group having 1 to 20 carbon atoms; at least one of $Ar^{1'}$ or $Ar^{2'}$ represents a substituted or unsubstituted condensed ring group having 10 to 60 nuclear carbon atoms or a substituted or unsubstituted mono hetero condensed ring group having 3 to 60 nuclear carbon atoms;

$L^1$ and $L^2$ in general formula (1') each independently represents a single bond, a substituted or unsubstituted arylene group having 6 to 60 nuclear carbon atoms, a substituted or unsubstituted hetero arylene group having 3 to 60 nuclear carbon atoms, or a substituted or unsubstituted fluorenylene group;

R in general formula (1') represents hydrogen atom, a substituted or unsubstituted aryl group having 6 to 60 nuclear carbon atoms or a substituted or unsubstituted heteroaryl group having 3 to 60 nuclear carbon atoms, a substituted or unsubstituted alkyl group having 1 to 20 carbon atoms, or a substituted or unsubstituted alkoxy group having 1 to 20 carbon atoms; n represents an integer of 0 to 5; when n represents an integer of 2 or greater, the atoms or groups represented by a plurality of R may be the same with or different from each other, and the groups represented by the plurality of R which are adjacent to each other may be bonded to each other to form an alicyclic carbon ring or an aromatic carbon ring.

(2')

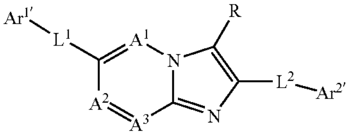

wherein $A^1$, $A^2$ and $A^3$ each independently represents nitrogen atom or carbon atom;

$Ar^{1'}$ represents a substituted or unsubstituted aryl group having 6 to 60 nuclear carbon atoms or a substituted or unsubstituted heteroaryl group having 3 to 60 nuclear carbon atoms; $Ar^{2'}$ represents a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms; or a substituted or unsubstituted alkoxy group having 1 to 20 carbon atoms; at least one of $Ar^{1'}$ or $Ar^{2'}$ represents a substituted or unsubstituted condensed ring group having 10 to 60 nuclear carbon atoms or a substituted or unsubstituted mono hetero condensed ring group having 3 to 60 nuclear carbon atoms;

$L^1$ and $L^2$ in general formula (2') each independently represents a single bond, a substituted or unsubstituted arylene group having 6 to 60 nuclear carbon atoms, a substituted or unsubstituted hetero arylene group having 3 to 60 nuclear carbon atoms, or a substituted or unsubstituted fluorenylene group; and R' in general formula (2') represents hydrogen atom, a substituted or unsubstituted aryl group having 6 to 60 nuclear carbon atoms or a substituted or unsubstituted heteroaryl group having 3 to 60 nuclear carbon atoms, a substituted or unsubstituted alkyl group having 1 to 20 carbon atoms, or a substituted or unsubstituted alkoxy group having 1 to 20 carbon atoms.

(3')

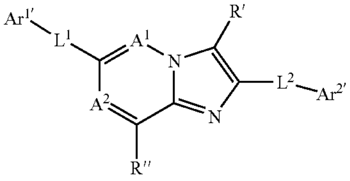

wherein $A^1$ and $A^2$ each independently represents nitrogen atom or carbon atom;

$Ar^{1'}$ represents a substituted or unsubstituted aryl group having 6 to 60 nuclear carbon atoms or a substituted or unsubstituted heteroaryl group having 3 to 60 nuclear carbon atoms; $Ar^{2'}$ represents a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms; or a substituted or unsubstituted alkoxy group having 1 to 20 carbon atoms; at least one of $Ar^{1'}$ or $Ar^{2'}$ represents a substituted or unsubstituted condensed ring group having 10 to 60 nuclear carbon atoms or a substituted or unsubstituted mono hetero condensed ring group having 3 to 60 nuclear carbon atoms;

$L^1$ and $L^2$ in general formula (3') each independently represents a single bond, a substituted or unsubstituted arylene group having 6 to 60 nuclear carbon atoms, a substituted or unsubstituted hetero arylene group having 3 to 60 nuclear carbon atoms, or a substituted or unsubstituted fluorenylene group; and R' and R" in general formula (3') each independently represents hydrogen atom, a substituted or unsubstituted aryl group having 6 to 60 nuclear carbon atoms or a substituted or unsubstituted heteroaryl group having 3 to 60 nuclear carbon atoms, a substituted or unsubstituted alkyl group having 1 to 20 carbon atoms, or a substituted or unsubstituted alkoxy group having 1 to 20 carbon atoms. Further, R' and R" may be the same or different from each other.

Also, the present invention provides a material for the organic EL device comprising the above derivative of heterocyclic compound having nitrogen atom.

Moreover, the present invention provides an organic EL device comprising at least one of organic compound layers including a light emitting layer sandwiched between a pair of electrode, wherein the organic EL device comprises the foregoing derivative of heterocyclic compound having nitrogen atom of the invention in at least one of the organic compound layers.

THE PREFERRED EMBODIMENT TO CARRY OUT THE INVENTION

The derivatives of heterocyclic compound having nitrogen atom of the present invention (referred to as "compound of the present invention" below) are represented by any one of the above general formulae (1), (1') to (3').

First, the derivatives of heterocyclic compound having nitrogen atom represented by general formula (1) of the present invention will be explained below.

In general formula (1), HAr represents a heterocyclic group having nitrogen atom, which has 3 to 40 carbon atoms and which may have a substituent. The heterocyclic group having nitrogen atom and having 3 to 40 carbon atoms is not specifically restricted and may be a cyclic group having at least one nitrogen atom as constituent element of a ring, may be a monocyclic group or may be a polycyclic group with condensed plural rings. Examples of the heterocyclic group having nitrogen atom and having 3 to 40 carbon atoms include pyridine, pyrimidine, pyrazine, pyridazine, triazine, a quinoline, quinoxaline, acridine, imidazo [1,2-a] pyridine, imidazo [1,2-a] pyrimidine, etc. Examples of the substituent to the heterocyclic group having nitrogen atom include groups corresponding to $R^1$ to $R^{102}$ in $Ar^1$ which will be described below.

It is preferable that HAr is selected from among the group consisting of the following general formulae (2) to (36):

(2)

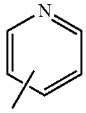

(3)

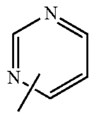

(4)

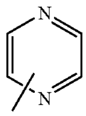

(5)

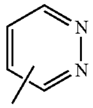

(6)

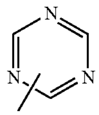

-continued (7)

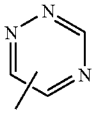

(8)

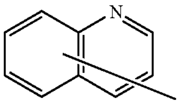

(9)

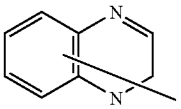

(10)

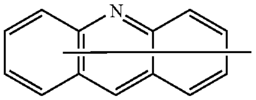

(11)

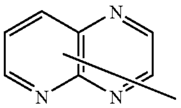

(12)

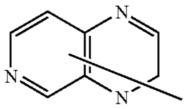

(13)

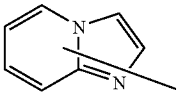

(14)

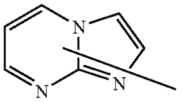

(15)

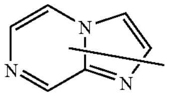

(16)

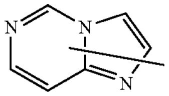

(17)

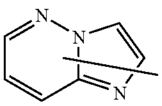

(18)

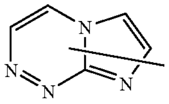

(19)

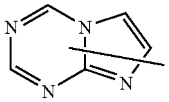

(20)

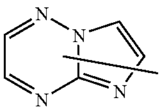

-continued (21)

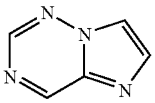

(22)

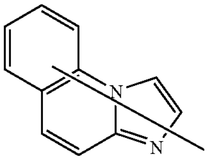

(23)

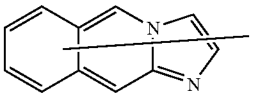

(24)

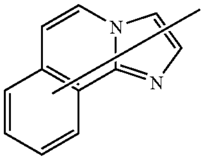

(25)

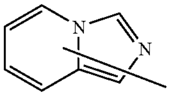

(26)

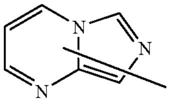

(27)

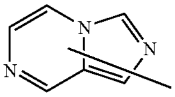

(28)

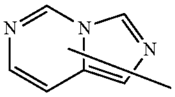

(29)

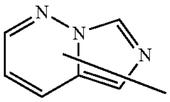

(30)

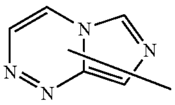

(31)

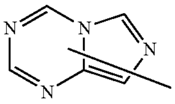

(32)

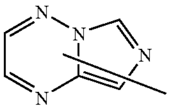

(33)

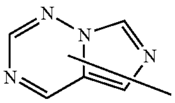

-continued (34)

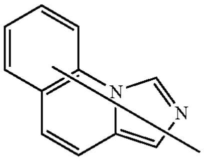

(35)

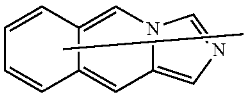

(36)

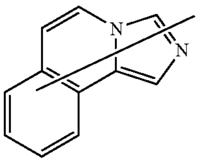

In the above general formulae (2) to (36), carbon atom in each heterocycle may be bonded with a bonding group comprising an aryl group having 6 to 60 carbon atoms and may have a substituent, a heteroaryl group having 3 to 60 carbon atoms and may have a substituent, an alkyl group having 1 to 20 carbon atoms and may have a substituent or an alkoxy group having 1 to 20 carbon atoms and may have a substituent. When there are plural of the bonding group, the bonding groups may be the same with or different from each other.

In the above general formulae (8) to (36), continuous lines showing bonding location between HAr and L are illustrated as going through all rings composing each many-membered ring, which mean that bonding location between HAr and L may be at any location among the many-membered ring of HAr.

The aryl group having 6 to 60 carbon atoms is preferably an aryl group having 6 to 40 carbon atoms, more preferably an aryl group having 6 to 20 carbon atoms. Specific examples of the aryl group having 6 to 20 carbon atoms include phenyl group, naphthyl group, anthryl group, phenanthryl group, naphthacenyl group, chrysenyl group, pyrenyl group, biphenyl group, terphenyl group, tolyl group, t-butylphenyl group, (2-phenylpropyl) phenyl group, fluoranthenyl group, fluorenyl group, monovalent group consisting of spirobifluorene, perfluorophenyl group, perfluoronaphthyl group, perfluoro anthryl group, perfluorinated biphenyl group, monovalent group consisting of 9-phenylanthracene, monovalent group consisting of 9-(1'-naphthyl) anthracene, monovalent group consisting of 9-(2'-naphthyl) anthracene, monovalent group consisting of 6-phenylchrysene, monovalent group consisting of 9-[4-(diphenylamino) phenyl] anthracene, etc. Among these, phenyl group, naphthyl group, biphenyl group, terphenyl group, 9-(10-phenyl) anthryl group, 9-[10-(1'-naphthyl)] anthryl group, 9-[10-(2'-naphthyl)] anthryl group or so is preferable.

The heteroaryl group having 3 to 60 carbon atoms is preferably a heteroaryl group having 3 to 40 carbon atoms, more preferably a heteroaryl group having 3 to 20 carbon atoms. Specific examples of the heteroaryl group having 3 to 20 carbon atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, etc. Among these, pyridyl group, quinolyl group and isoquinolyl group are preferable.

The alkyl group having 1 to 20 carbon atoms is preferably an alkyl group having 1 to 6 carbon atoms. Specific examples of the alkyl group having 1 to 6 carbon atoms include methyl group, ethyl group, propyl group, butyl group, pentyl group, hexyl group, etc. The alkyl group having 3 or more carbon atoms may be linear, cyclic or branched.

The alkoxy group having 1 to 20 carbon atoms is preferably an alkoxy group having 1 to 6 carbon atoms. Specific examples of the alkoxy group having 1 to 6 carbon atoms include methoxy group, ethoxy group, propoxy group, butoxy group, pentyloxy group, hexyloxy group, etc. The alkoxy group having 3 or more carbon atoms may be linear, cyclic or branched.

In general formula (1), it is preferable that HAr represents a group selected from the group consisting of

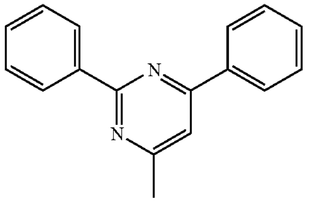

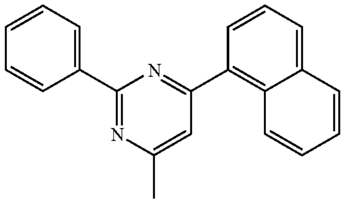

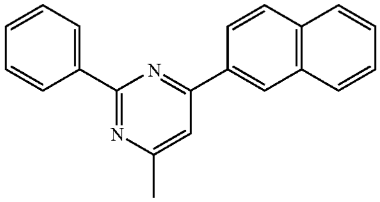

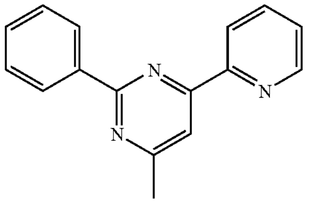

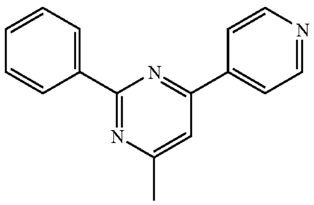

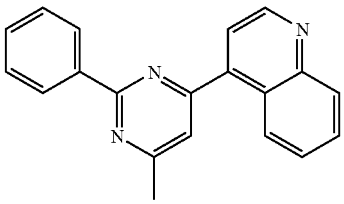

-continued

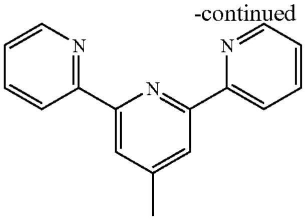

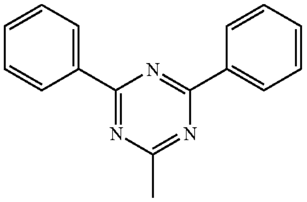

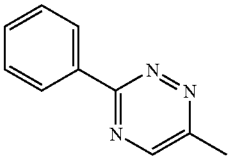 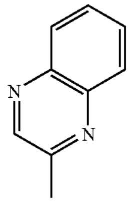 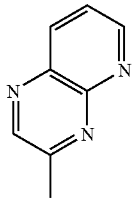

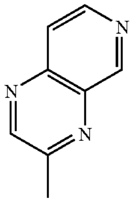 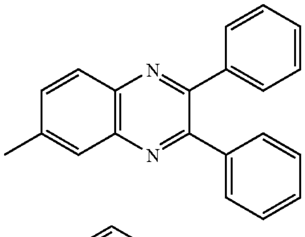

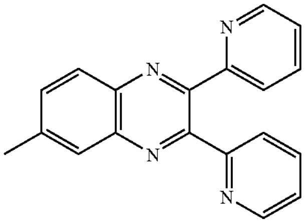

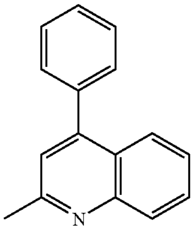 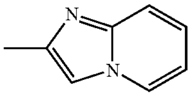

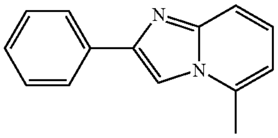

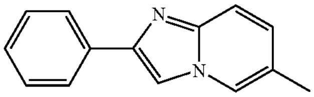

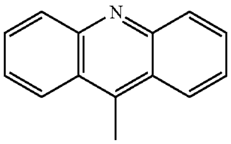

-continued

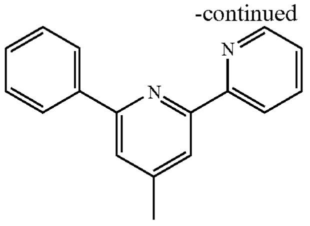

In general formula (1), L represents a single bond, an arylene group having 6 to 60 carbon atoms and may have a substituent, a heteroarylene group having 3 to 60 carbon atoms and may have a substituent or a fluorenylene group which may have a substituent.

The arylene group having 6 to 60 carbon atoms is preferably an arylene group having 6 to 40 carbon atoms, more preferably arylene group having 6 to 20 carbon atoms. Specific examples of arylene group having 6 to 20 carbon atoms include divalent groups formed by removing one hydrogen atom from the aryl groups described about the foregoing bonding group.

The heteroarylene group having 3 to 60 carbon atoms is preferably a heteroarylene group having 3 to 40 carbon atoms, more preferably heteroarylene group having 3 to 20 carbon atoms. Specific examples of heteroarylene group having 3 to 20 carbon atoms include divalent groups formed by removing one hydrogen atom from the heteroaryl groups described about the foregoing bonding group.

With regard to the foregoing arylene group having 6 to 60 carbon atoms or the heteroarylene group having 3 to 60 carbon atoms, there are a halogen atom, an alkyl group having 1 to 20 carbon atoms and may have a substituent, an alkoxy group having 1 to 20 carbon atoms and may have a substituent, an aryloxy group having 6 to 40 carbon atoms and may have a substituent, an aryl group having 6 to 40 carbon atoms and may have a substituent, a heteroaryl group having 3 to 40 carbon atoms and may have a substituent or so.

In general formula (1), it is preferable that L represents a group selected from the group consisting of

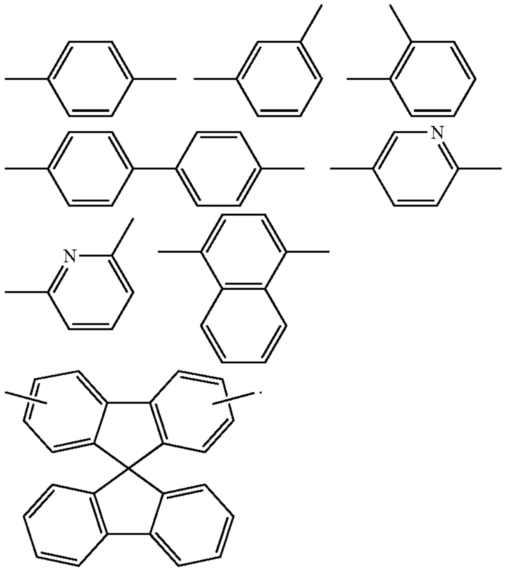

In general formula (1), $Ar^1$ represents a divalent aromatic hydrocarbon group having 6 to 60 carbon atoms and may have a substituent. The divalent aromatic hydrocarbon group having 6 to 60 carbon atoms is preferably a divalent aromatic hydrocarbon group having 6 to 40 carbon atoms, more preferably a divalent aromatic hydrocarbon group having 6 to 20 carbon atoms. Specific examples of the divalent aromatic hydrocarbon group having 6 to 20 carbon atoms include divalent groups formed by removing one hydrogen atom from the examples described about the foregoing aryl group of HAr.

It is preferable that, in general formula (1), $Ar^1$ represents a group represented by one of the following general formulae (43) to (54):

(43)

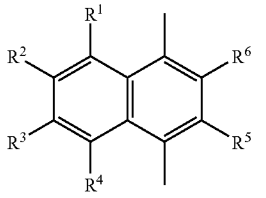

(44)

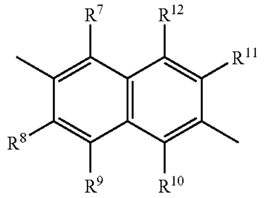

(45)

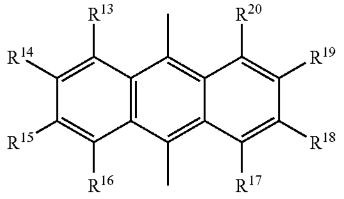

(46)

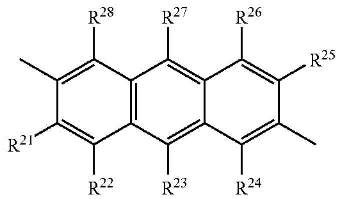

(47)

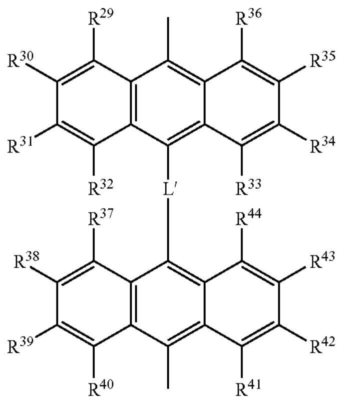

-continued (48)

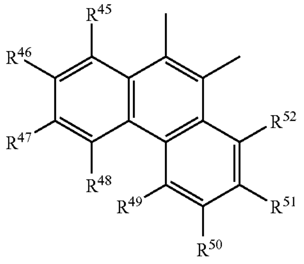

(49)

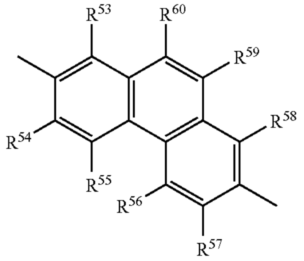

(50)

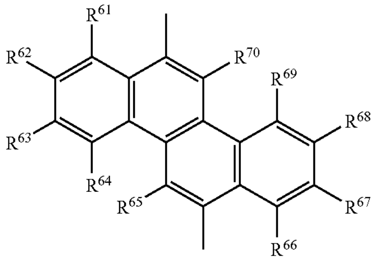

(51)

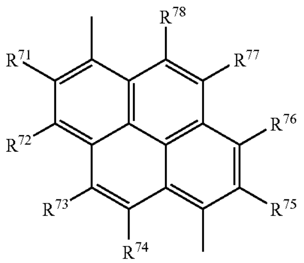

(52)

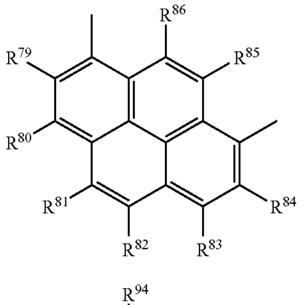

(53)

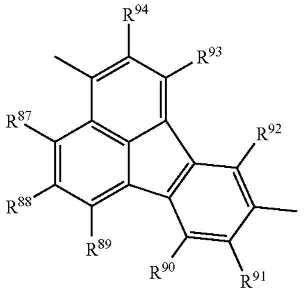

-continued (54)

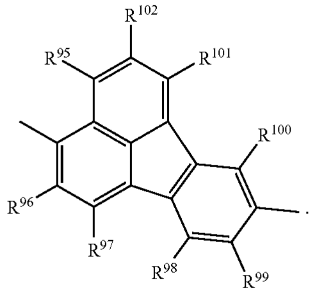

In the above formulae, $R^1$ to $R^{102}$ each may be independently bonded with a bonding group of a halogen atom, an alkyl group having 1 to 20 carbon atoms and may have a substituent, an alkoxyl group having 1 to 20 carbon atoms and may have a substituent, an aryloxyl group having 6 to 40 carbon atoms and may have a substituent, a diarylamino group having 12 to 80 carbon atoms and may have a substituent, an aryl group having 6 to 40 carbon atoms and may have a substituent, a heteroaryl group having 3 to 40 carbon atoms and may have a substituent, or a diarylamino group having 18 to 120 carbon atoms and may have a substituent. When there are plural of bonding groups, the bonding group may be the same or different with each other.

L' in the above formulae represents the single bond or a group selected from the following groups:

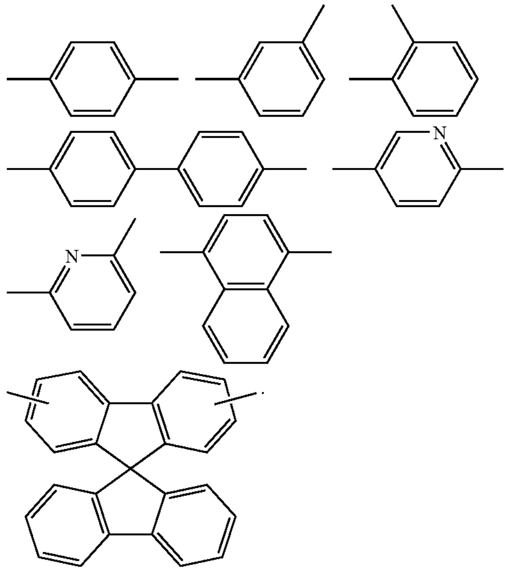

In general formula (1), $Ar^2$ represents an aryl group having 6 to 60 carbon atoms and may have a substituent or a heteroaryl group having 3 to 60 carbon atoms and may have a substituent.

Examples of the aryl group having 6 to 60 carbon atoms and the heteroaryl group having 3 to 60 carbon atoms include the groups described above as the examples about the foregoing bonding group. Examples of the substituent include a halogen atom, an alkyl group having 1 to 20 carbon atoms and may have a substituent, an alkoxyl group having 1 to 20 carbon atoms and may have a substituent, an aryloxyl group having 6 to 40 carbon atoms and may have a substituent, a diarylamino group having 12 to 80 carbon atoms and may have a substituent, an aryl group having 6 to 40 carbon atoms and may have a substituent, a heteroaryl group having 3 to 40 carbon atoms and may have a substituent, etc. Preferable examples of the substituent are alkyl groups having 1 to 6 carbon atoms. The foregoing arylene group having 6 to 60 carbon atoms or heteroarylene group having 3 to 60 carbon atoms is preferably unsubstituted.

Further, $Ar^2$ is preferably a group selected from the following groups:

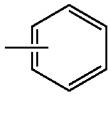
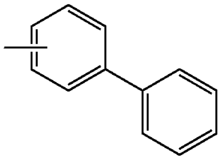
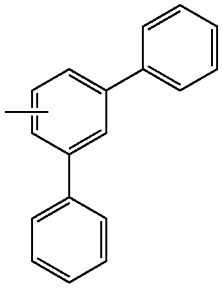
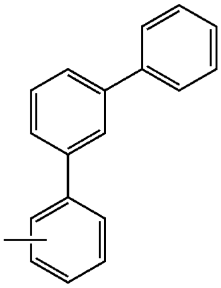
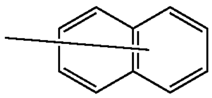
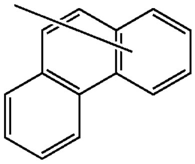
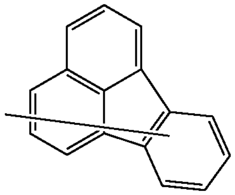
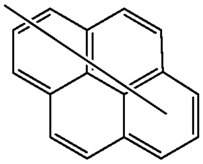
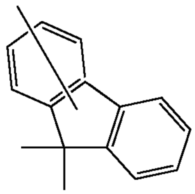

and more preferably a group selected from the following groups:

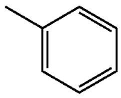
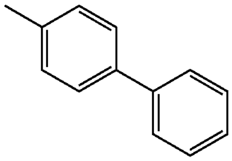

-continued

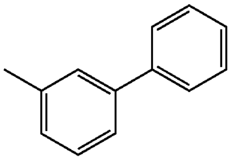
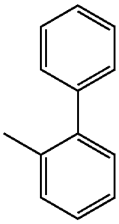
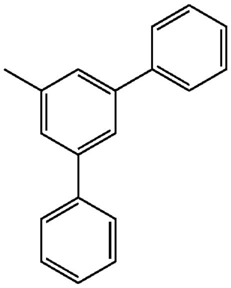
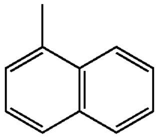
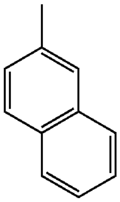
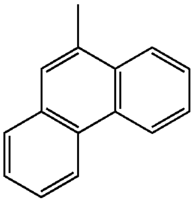
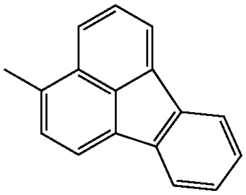
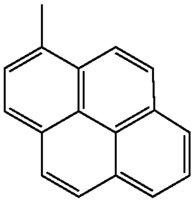
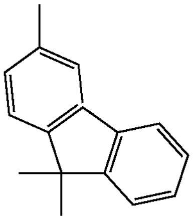

In the foregoing general formula (1), (i) a derivative of heterocyclic compound having nitrogen atom wherein L represents an arylene group having 6 to 60 carbon atoms and may have a substituent, a heteroarylene group having 3 to 60 carbon atoms and may have a substituent or or a fluorenylene group which may have a substituent; and $Ar^1$ represents a divalent condensed aromatic hydrocarbon group having 10 to 60 carbon atoms and may have a substituent; or (ii) L represents single bond and $Ar^1$ represents a divalent condensed aromatic hydrocarbon group having 11 to 60 carbon atoms and may have a substituent.

In the case of above item (i), $Ar^1$ is preferably any one selected from the condensed ring groups of the following general formula (37) to (42):

(37)

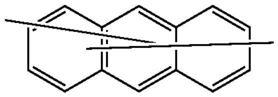

(38)

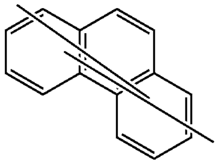

(39)

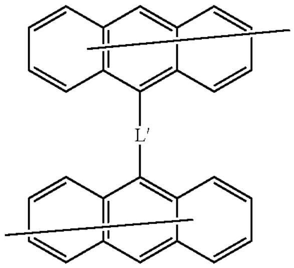

(40)

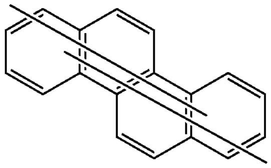

(41)

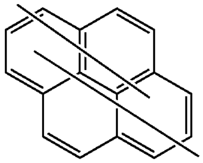

(42)

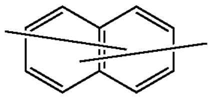

In the above general formulae, each condensed ring groups may be bonded with a bonding group of a halogen atom, an alkyl group having 1 to 20 carbon atoms and may have a substituent, an alkoxyl group having 1 to 20 carbon atoms and may have a substituent, an aryloxyl group having to 20 carbon atoms and may have a substituent, an aryloxyl group having 6 to 40 carbon atoms and may have a substituent, an aryl group having 6 to 40 carbon atoms and may have a substituent, or a heteroaryl group having 3 to 40 carbon atoms and may have a substituent. When there are plural of bonding groups, the bonding group may be the same or different with each other.

L' represents a single bond or a group selected from the following groups:

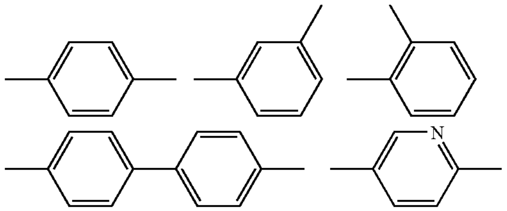

-continued

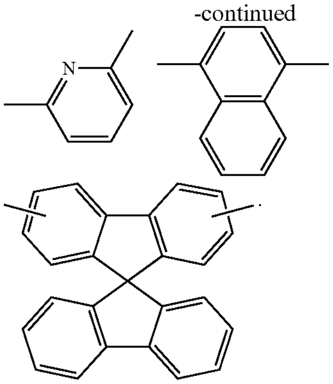

Examples of the halogen atom include fluorine atom, chlorine atom, bromine atom and iodine atom.

The alkyl group having 1 to 20 carbon atoms is preferably an alkyl group having 1 to 6 carbon atoms. Specific examples of the alkyl group having 1 to 6 carbon atoms include methyl group, ethyl group, propyl group, butyl group, pentyl group, hexyl group, etc. The alkyl group having 3 or more carbon atoms may be linear, cyclic or branched.

The alkoxy group having 1 to 20 carbon atoms is preferably an alkoxy group having 1 to 6 carbon atoms. Specific examples of the alkoxy group having 1 to 6 carbon atoms include methoxy group, ethoxy group, propoxy group, butoxy group, pentyloxy group, hexyloxy group, etc. The alkoxy group having 3 or more carbon atoms may be linear, cyclic or branched.

The aryloxy group having 6 to 40 carbon atoms is preferably an aryloxy group having 6 to 20 carbon atoms. Specific examples of the aryloxy group having 6 to 20 carbon atoms include phenoxy group, biphenyl oxy group, etc.

Examples of the aryl group having 6 to 40 carbon atoms and the heteroaryl group having 3 to 40 carbon atoms include the groups described above as the examples about the foregoing bonding group.

Further, examples of the substituent include a halogen atom, an alkyl group having 1 to 20 carbon atoms and may have a substituent, an alkoxyl group having 1 to 20 carbon atoms and may have a substituent, an aryloxyl group having 6 to 40 carbon atoms and may have a substituent, a diarylamino group having 12 to 80 carbon atoms and may have a substituent, an aryl group having 6 to 40 carbon atoms and may have a substituent, a heteroaryl group having 3 to 40 carbon atoms and may have a substituent, etc.

In the case of above item (ii), Ar1 is preferably any one selected from the condensed ring groups of the following general formula (37) to (41):

(37)

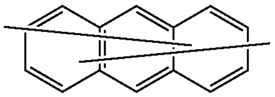

(38)

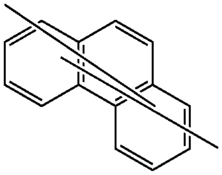

-continued (39)

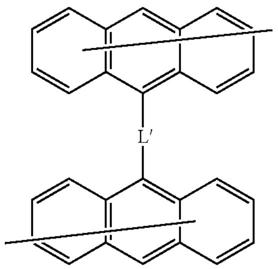

(40)

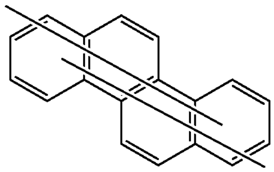

(41)

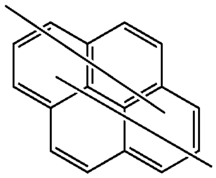

bonded with a bonding group of a halogen atom, an alkyl group having 1 to 20 carbon atoms and may have a substituent, an alkoxyl group having 1 to 20 carbon atoms and may have a substituent, an aryloxyl group having 6 to 40 carbon atoms and may have a substituent, an aryl group having 6 to 40 carbon atoms and may have a substituent, or a heteroaryl group having 3 to 40 carbon atoms and may have a substituent. When there are plural of bonding groups, the bonding group may be the same or different with each other. L' is the same as in the case of the foregoing item (i).

Preferable numbers of carbon atoms, specific examples and the substituents are also the same as in the case of the foregoing item (i).

The derivative of heterocyclic compound having nitrogen atom represented by general formula (1) of the present invention can be prepared by means of publicly known method.

For example, it may be prepared in accordance with Suzuki reaction between HAr-L-$Ar^1$—X or HAr-L-X and $(HO)_2B$—$Ar^2$ or $(HO)_2B$—$Ar^1$—$Ar^2$.

Specific examples of the derivative of heterocyclic compound having nitrogen atom represented by general formula (1) of the present invention are as follows, however, the present invention is not limited to these typical compounds.

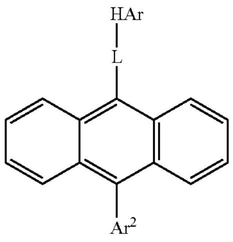

| Compound | HAr | L | $Ar^2$ |
|---|---|---|---|
| 1-1 | 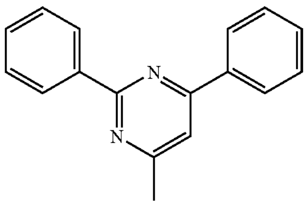 | — | 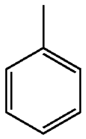 |
| 1-2 | 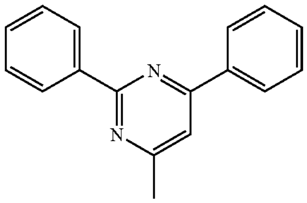 | — | 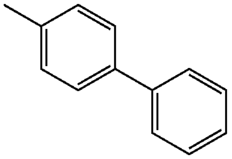 |

-continued
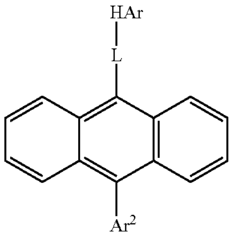
| Compound | HAr | L | $Ar^2$ |
|---|---|---|---|
| 1-3 | 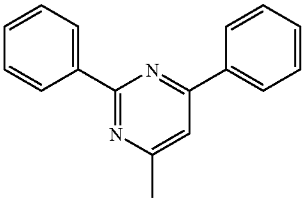 | — | 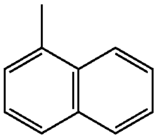 |
| 1-4 | 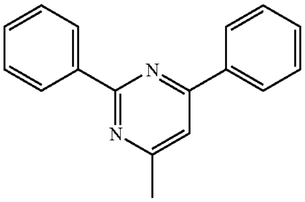 | — | 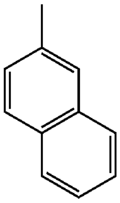 |
| 1-5 | 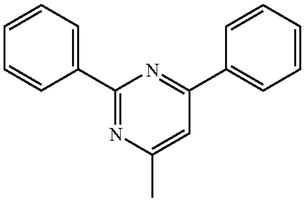 | — | 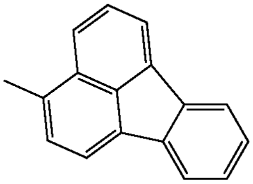 |
| 1-6 | 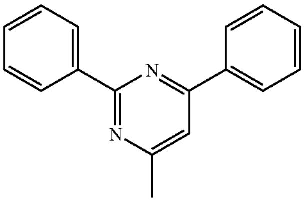 | — | 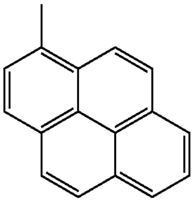 |
| 1-7 | 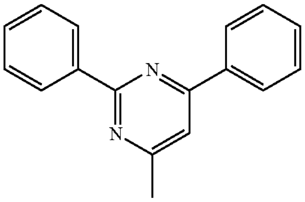 | — | 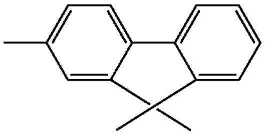 |
| 1-8 | 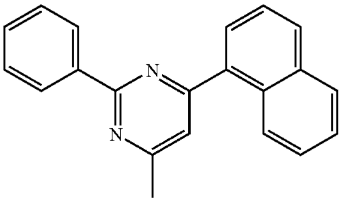 | — | 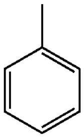 |

-continued
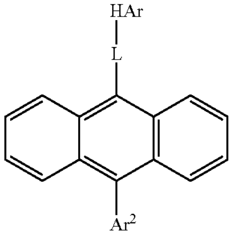
| Compound | HAr | L | $Ar^2$ |
| --- | --- | --- | --- |
| 1-9 | 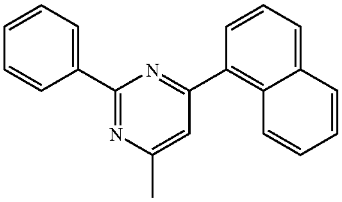 | — | 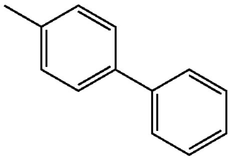 |
| 1-10 | 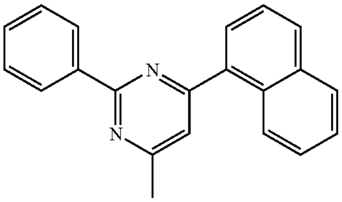 | — | 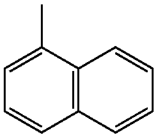 |
| 1-11 | 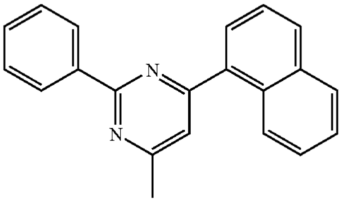 | — | 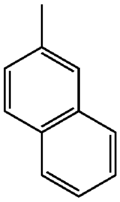 |
| 1-12 | 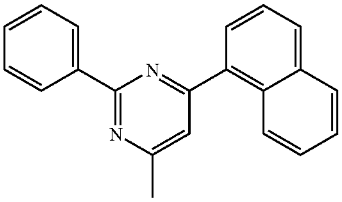 | — | 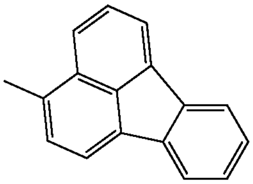 |
| 1-13 | 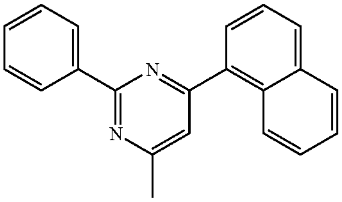 | — | 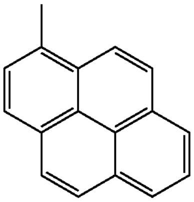 |
| 1-14 | 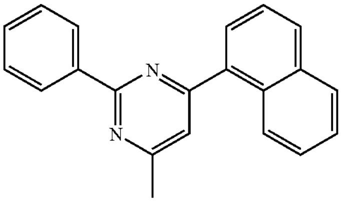 | — | 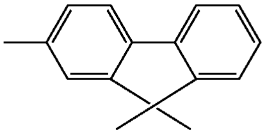 |

-continued
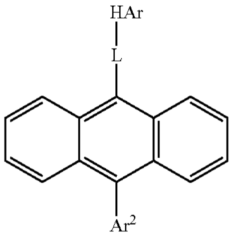
| Compound | HAr | L | Ar² |
| --- | --- | --- | --- |
| 1-15 | 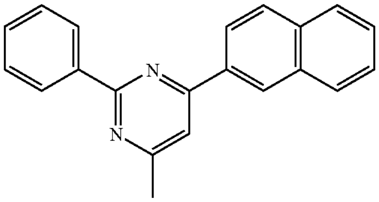 | — | 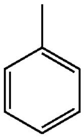 |
| 1-16 | 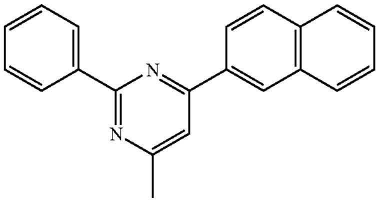 | — | 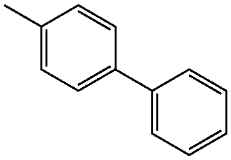 |
| 1-17 | 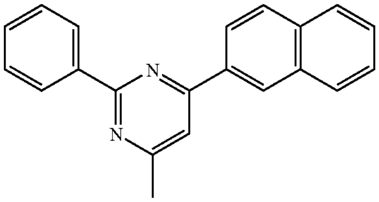 | — | 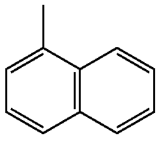 |
| 1-18 | 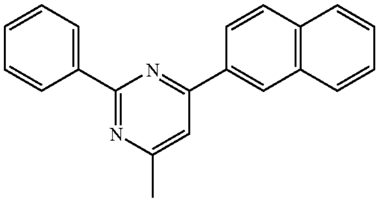 | — | 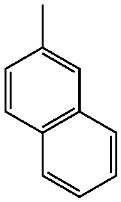 |
| 1-19 | 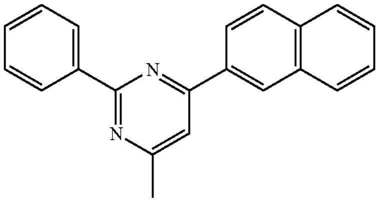 | — | 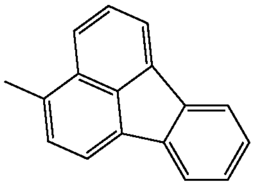 |
| 1-20 | 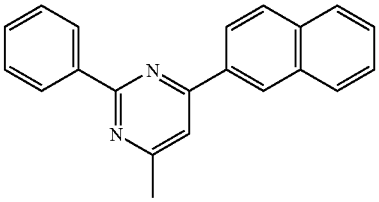 | — | 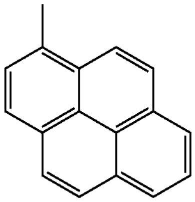 |

-continued
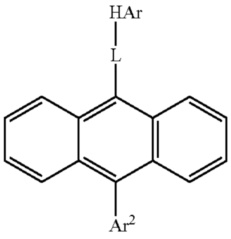
| Compound | HAr | L | Ar$^2$ |
| --- | --- | --- | --- |
| 1-21 | 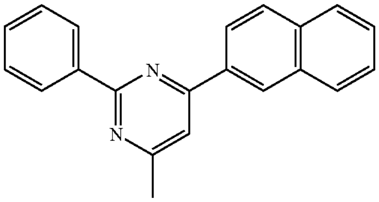 | — | 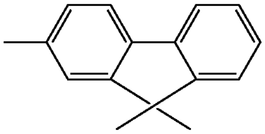 |
| 2-1 | 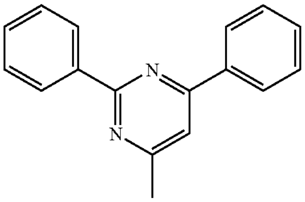 | 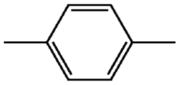 | 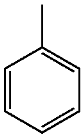 |
| 2-2 | 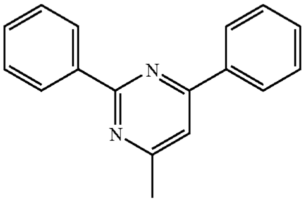 | 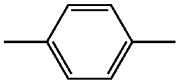 | 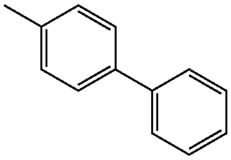 |
| 2-3 | 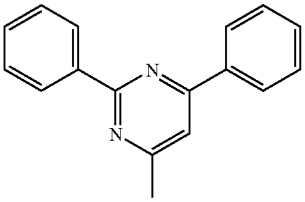 | 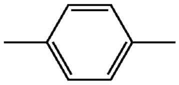 | 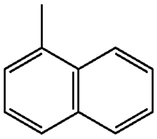 |
| 2-4 | 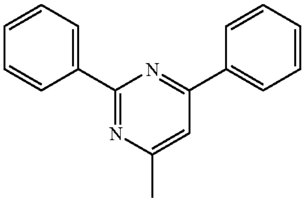 | 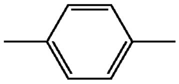 | 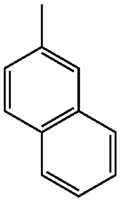 |
| 2-5 | 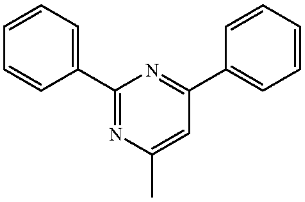 | 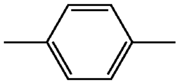 | 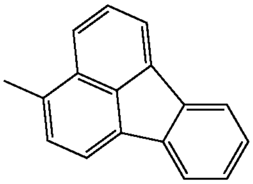 |

-continued
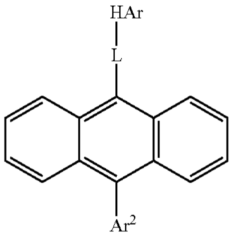
| Compound | HAr | L | Ar² |
|---|---|---|---|
| 2-6 | 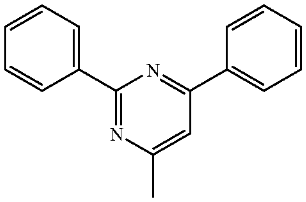 | 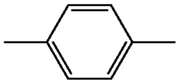 | 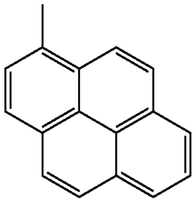 |
| 2-7 | 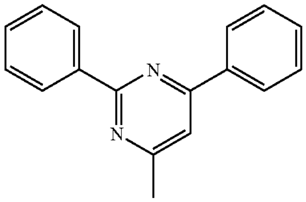 | 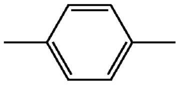 | 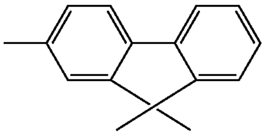 |
| 2-8 | 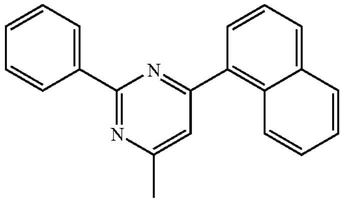 | 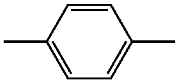 | 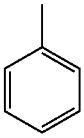 |
| 2-9 | 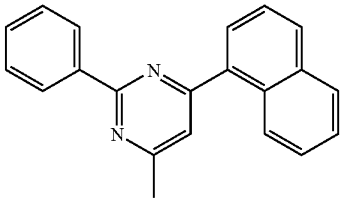 | 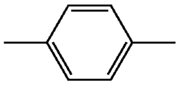 | 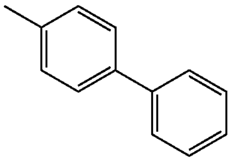 |
| 2-10 | 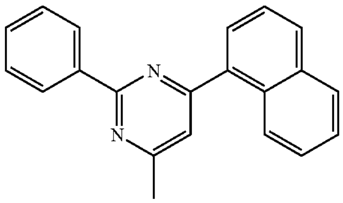 | 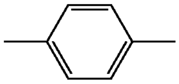 | 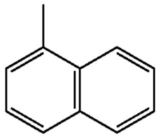 |
| 2-11 | 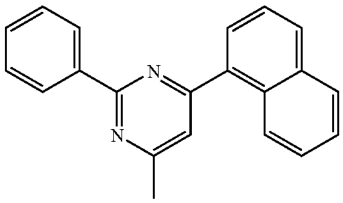 | 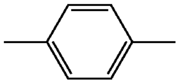 | 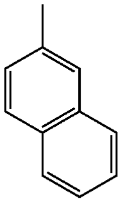 |

-continued
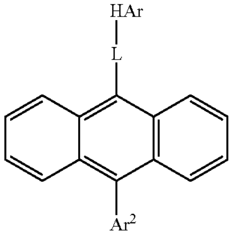
| Compound | HAr | L | $Ar^2$ |
| --- | --- | --- | --- |
| 2-12 | 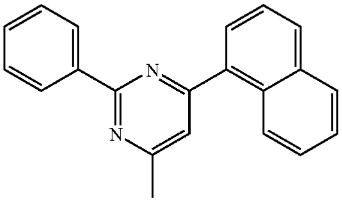 | 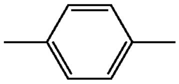 | 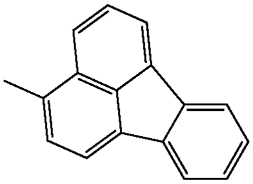 |
| 2-13 | 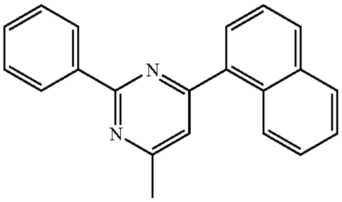 | 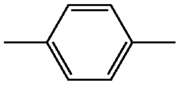 | 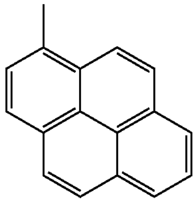 |
| 2-14 | 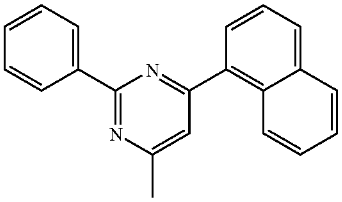 | 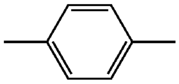 | 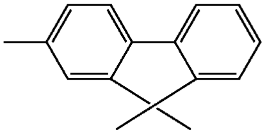 |
| 2-15 | 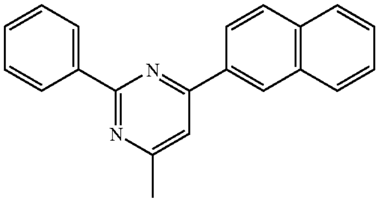 | 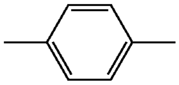 | 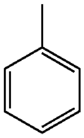 |
| 2-16 | 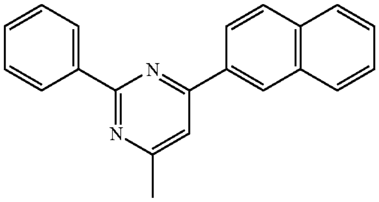 | 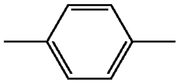 | 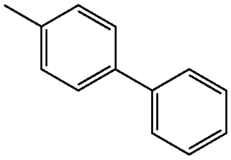 |
| 2-17 | 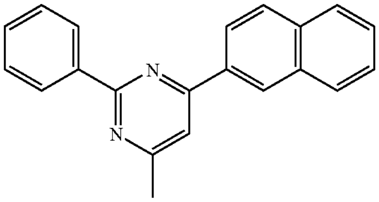 | 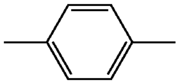 | 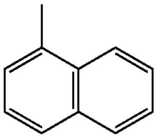 |

-continued
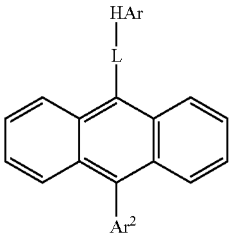
| Compound | HAr | L | $Ar^2$ |
| --- | --- | --- | --- |
| 2-18 | 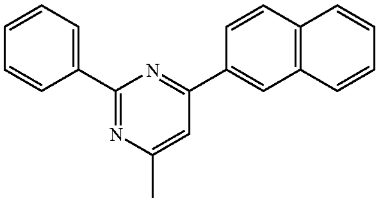 | 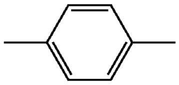 | 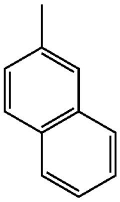 |
| 2-19 | 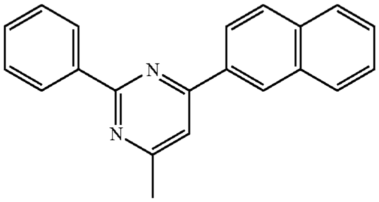 | 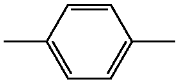 | 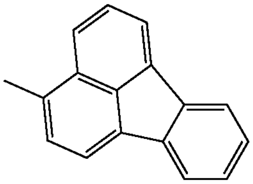 |
| 2-20 | 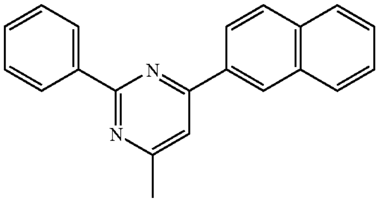 | 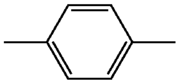 | 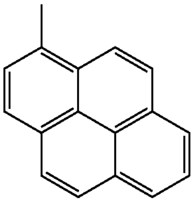 |
| 2-21 | 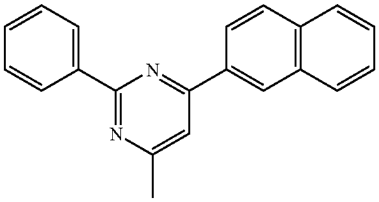 | 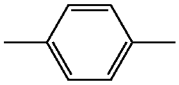 | 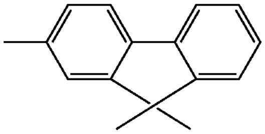 |
| 3-1 | 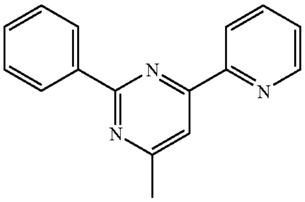 | — | 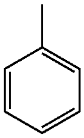 |
| 3-2 | 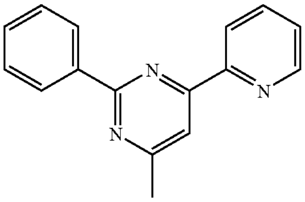 | — | 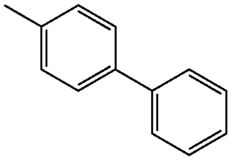 |

-continued
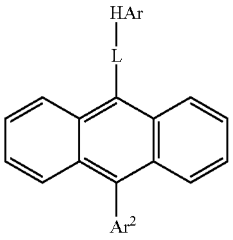
| Compound | HAr | L | $Ar^2$ |
| --- | --- | --- | --- |
| 3-3 | 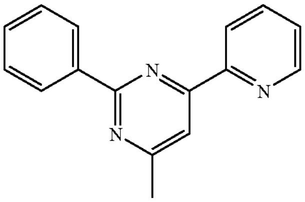 | — | 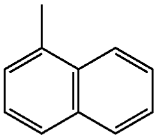 |
| 3-4 | 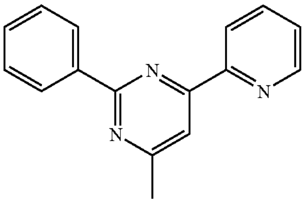 | — | 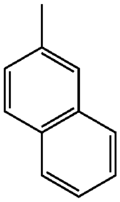 |
| 3-5 | 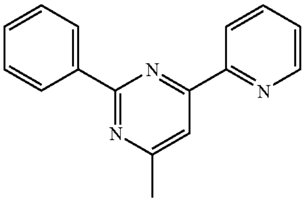 | — | 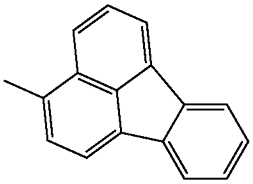 |
| 3-6 | 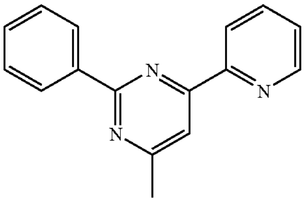 | — | 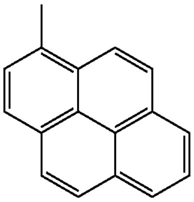 |
| 3-7 | 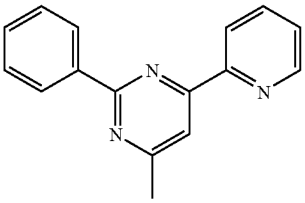 | — | 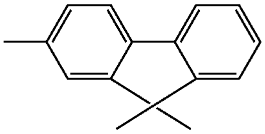 |
| 3-8 | 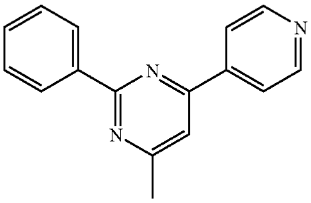 | — | 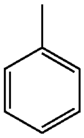 |

-continued
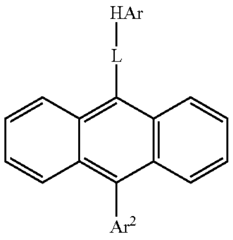
| Compound | HAr | L | Ar2 |
| --- | --- | --- | --- |
| 3-9 | 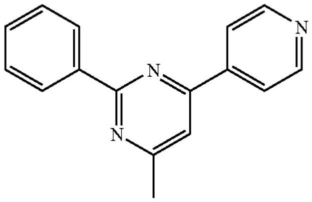 | — | 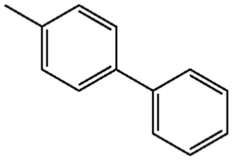 |
| 3-10 | 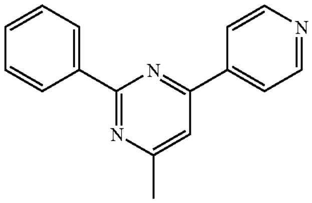 | — | 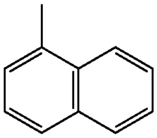 |
| 3-11 | 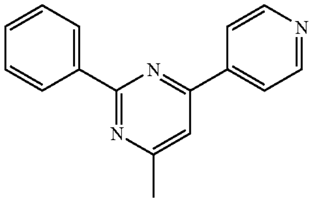 | — | 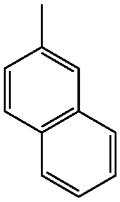 |
| 3-12 | 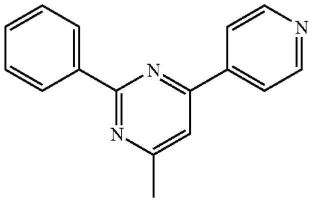 | — | 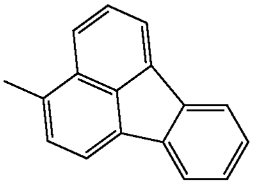 |
| 3-13 | 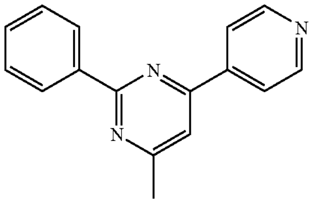 | — | 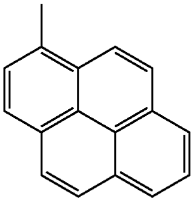 |
| 3-14 | 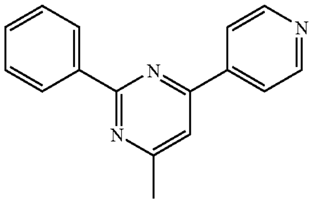 | — | 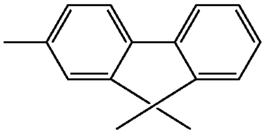 |

-continued
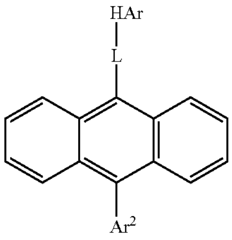
| Compound | HAr | L | $Ar^2$ |
| --- | --- | --- | --- |
| 3-15 | 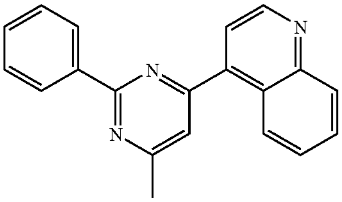 | — | 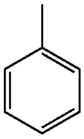 |
| 3-16 | 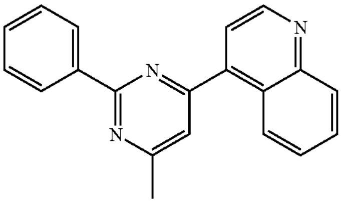 | — | 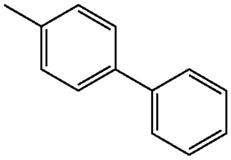 |
| 3-17 | 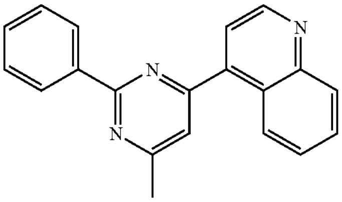 | — | 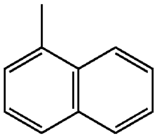 |
| 3-18 | 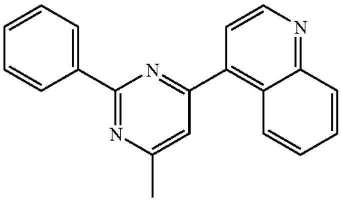 | — | 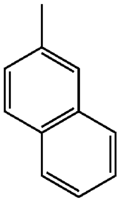 |
| 3-19 | 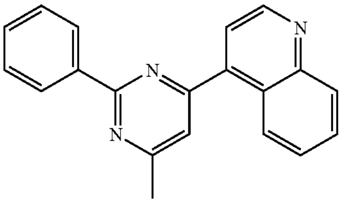 | — | 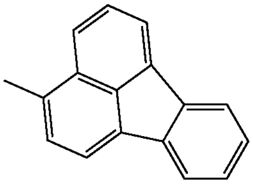 |
| 3-20 | 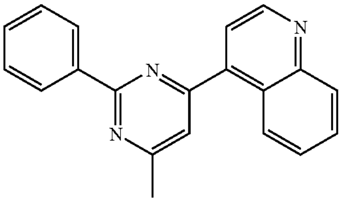 | — | 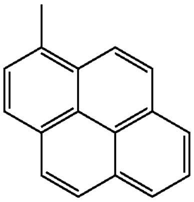 |

-continued
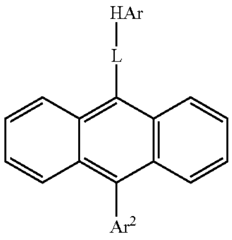
| Compound | HAr | L | Ar$^2$ |
| --- | --- | --- | --- |
| 3-21 | 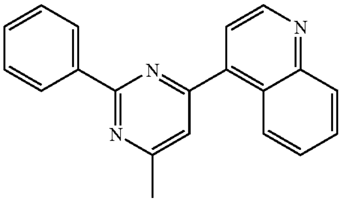 | — | 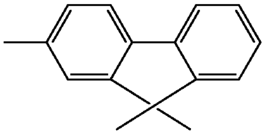 |
| 4-1 | 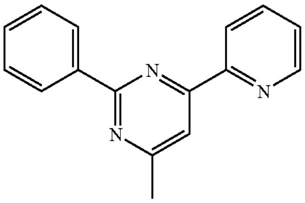 | 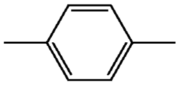 | 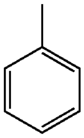 |
| 4-2 | 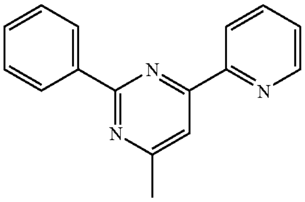 | 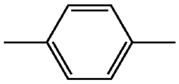 | 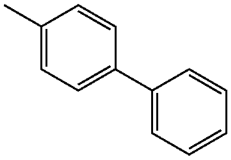 |
| 4-3 | 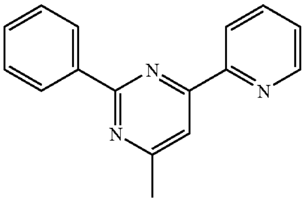 | 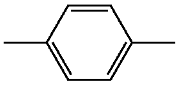 | 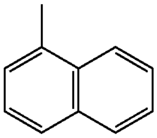 |
| 4-4 | 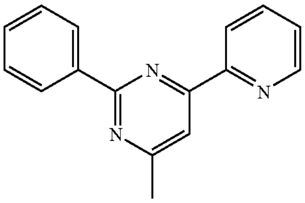 | 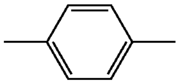 | 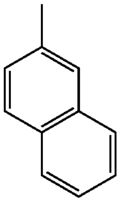 |
| 4-5 | 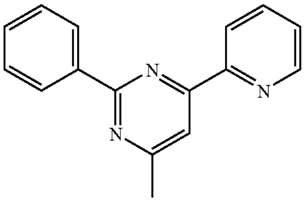 | 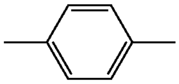 | 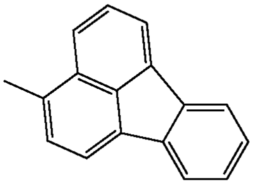 |

-continued
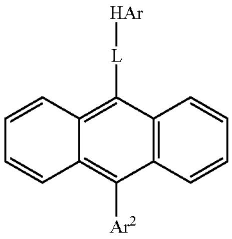
| Compound | HAr | L | Ar² |
|---|---|---|---|
| 4-6 | 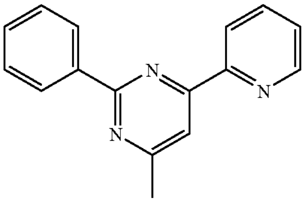 | 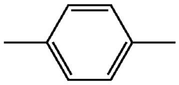 | 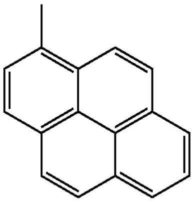 |
| 4-7 | 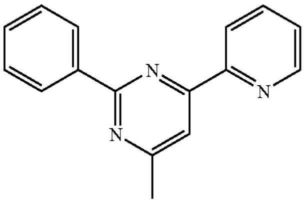 | 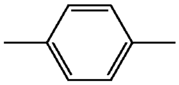 | 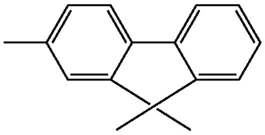 |
| 4-8 | 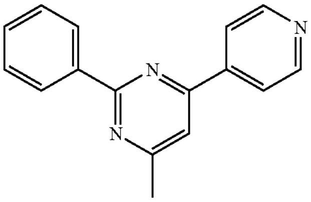 | 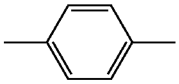 | 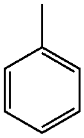 |
| 4-9 | 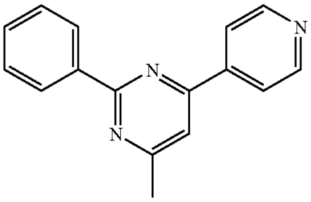 | 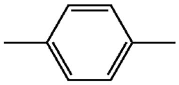 | 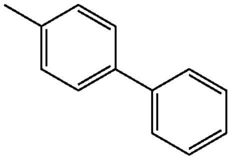 |
| 4-10 | 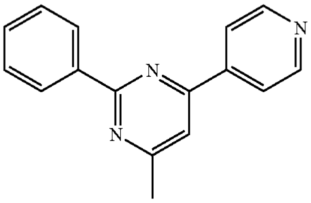 | 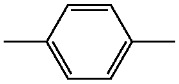 | 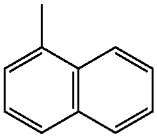 |
| 4-11 | 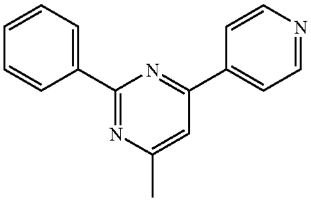 | 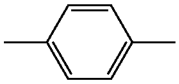 | 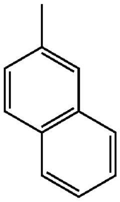 |

-continued
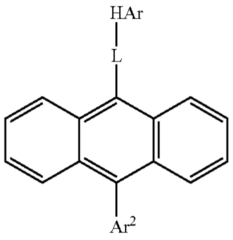
| Compound | HAr | L | Ar$^2$ |
|---|---|---|---|
| 4-12 | 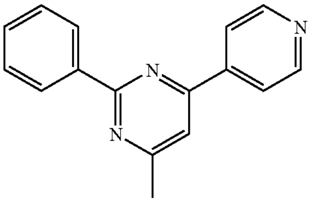 | 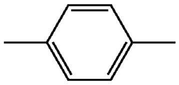 | 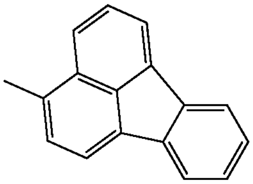 |
| 4-13 | 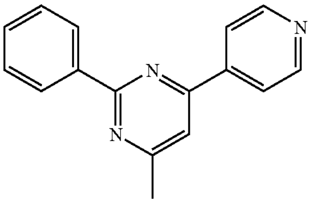 | 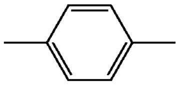 | 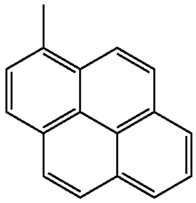 |
| 4-14 | 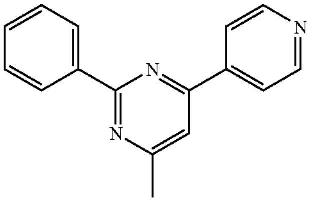 | 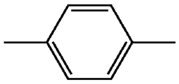 | 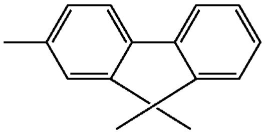 |
| 4-15 | 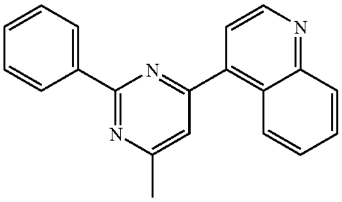 | 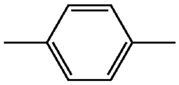 | 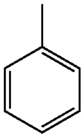 |
| 4-16 | 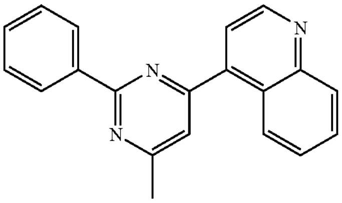 | 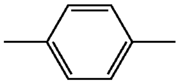 | 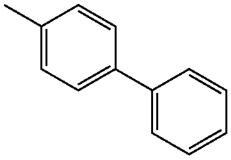 |
| 4-17 | 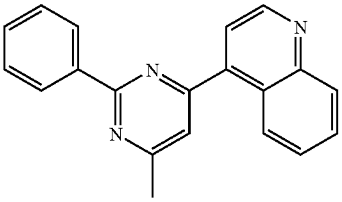 | 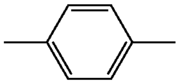 | 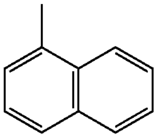 |

-continued
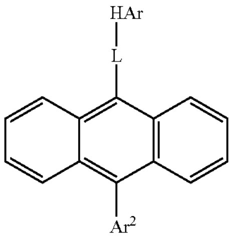
| Compound | HAr | L | Ar$^2$ |
|---|---|---|---|
| 4-18 | 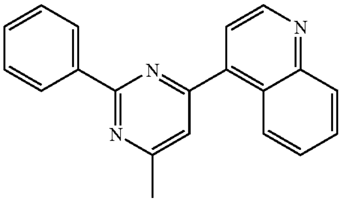 | 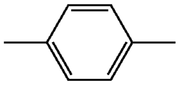 | 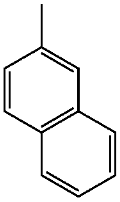 |
| 4-19 | 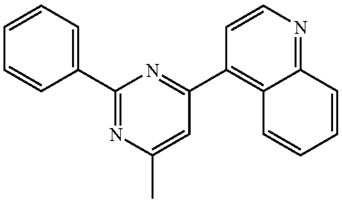 | 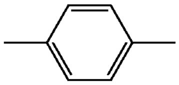 | 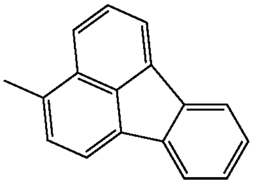 |
| 4-20 | 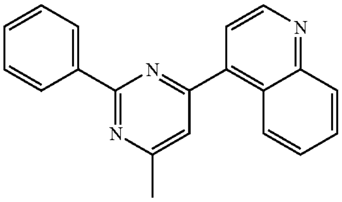 | 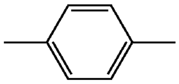 | 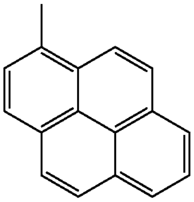 |
| 4-21 | 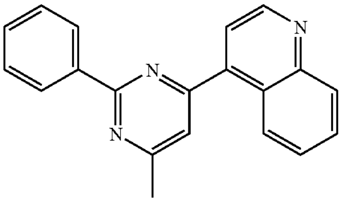 | 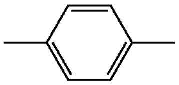 | 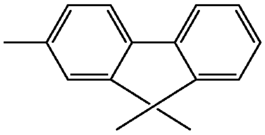 |
| 5-1 | 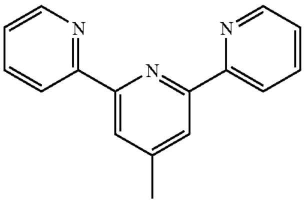 | — | 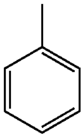 |
| 5-2 | 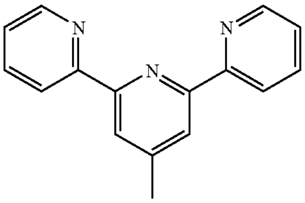 | — | 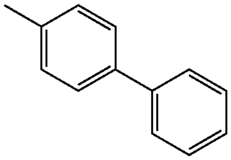 |

-continued
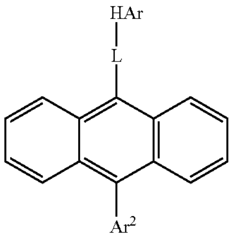
| Compound | HAr | L | Ar2 |
|---|---|---|---|
| 5-3 | 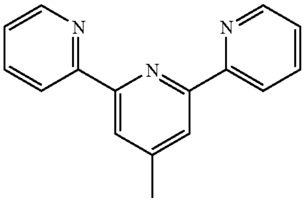 | — | 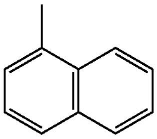 |
| 5-4 | 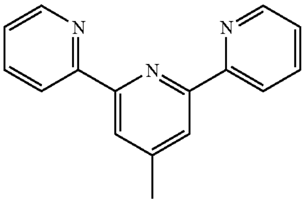 | — | 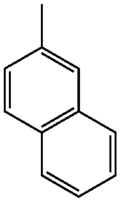 |
| 5-5 | 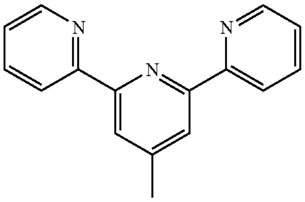 | — | 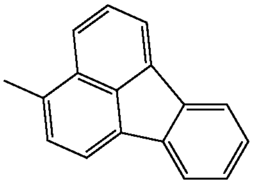 |
| 5-6 | 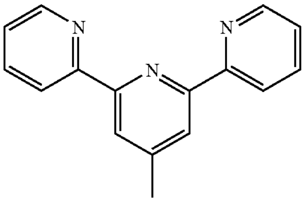 | — | 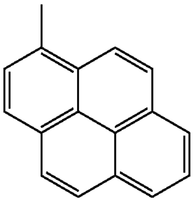 |
| 5-7 | 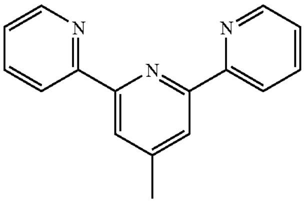 | — | 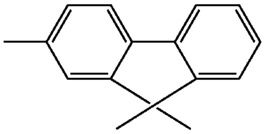 |
| 5-8 | 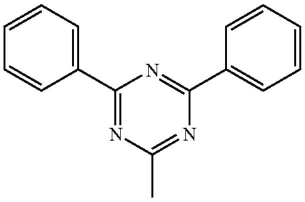 | — | 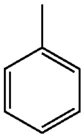 |

-continued
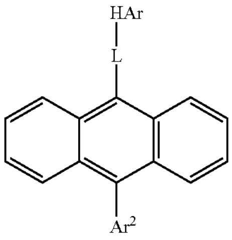
| Compound | HAr | L | $Ar^2$ |
|---|---|---|---|
| 5-9 | 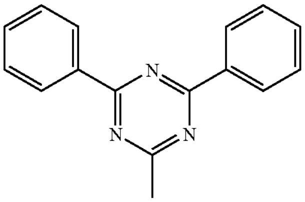 | — | 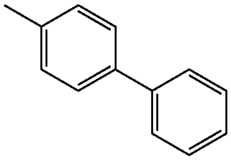 |
| 5-10 | 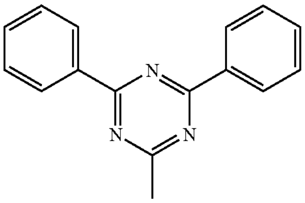 | — | 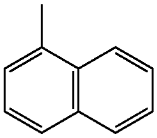 |
| 5-11 | 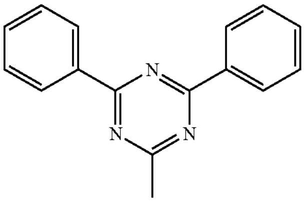 | — | 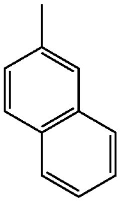 |
| 5-12 | 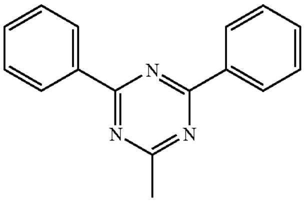 | — | 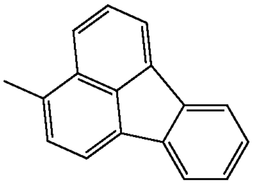 |
| 5-13 | 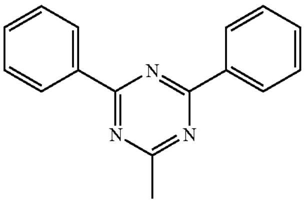 | — | 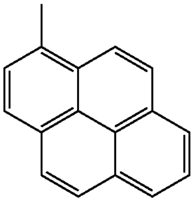 |
| 5-14 | 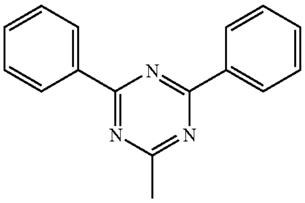 | — | 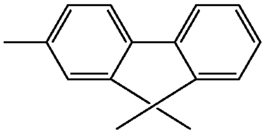 |

-continued
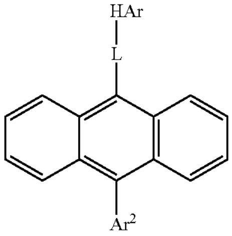
| Compound | HAr | L | Ar² |
| --- | --- | --- | --- |
| 5-15 | 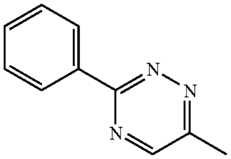 | — | 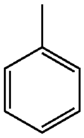 |
| 5-16 | 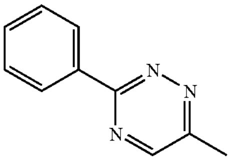 | — | 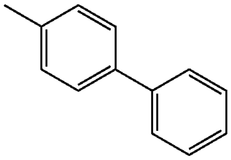 |
| 5-17 | 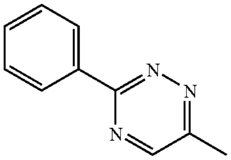 | — | 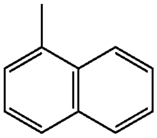 |
| 5-18 | 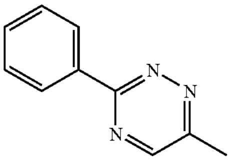 | — | 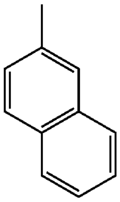 |
| 5-19 | 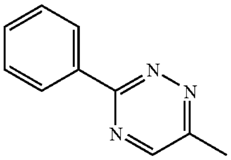 | — | 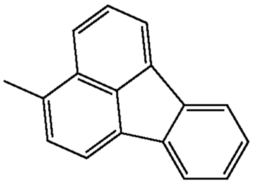 |
| 5-20 | 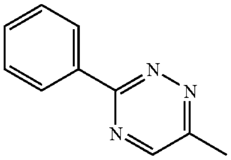 | — | 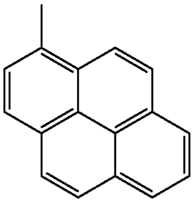 |
| 5-21 | 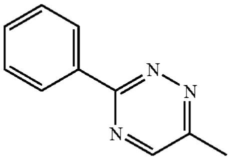 | — | 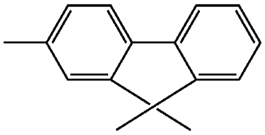 |

-continued
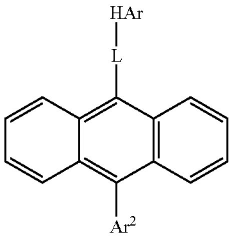
| Compound | HAr | L | $Ar^2$ |
|---|---|---|---|
| 6-1 | 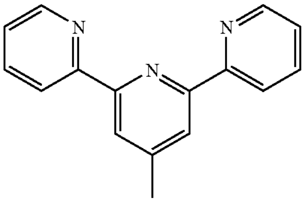 | 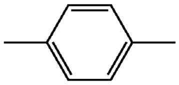 | 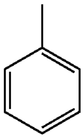 |
| 6-2 | 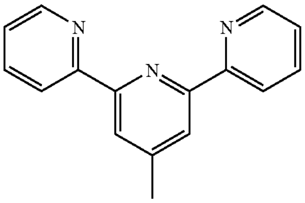 | 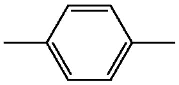 | 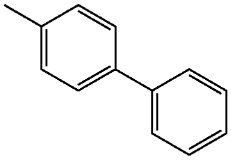 |
| 6-3 | 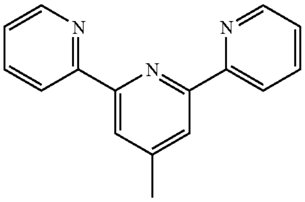 | 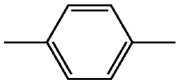 | 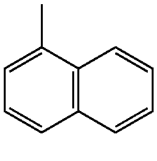 |
| 6-4 | 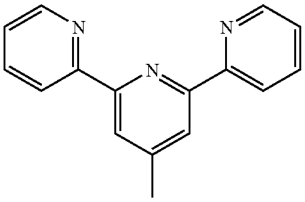 | 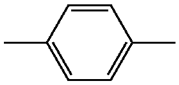 | 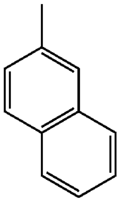 |
| 6-5 | 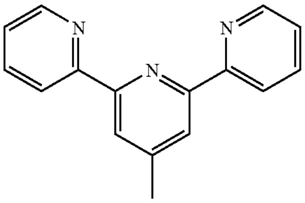 | 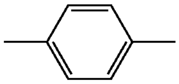 | 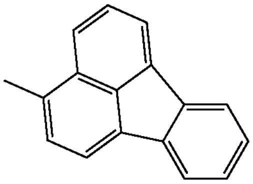 |
| 6-6 | 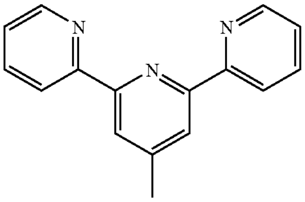 | 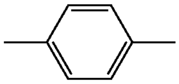 | 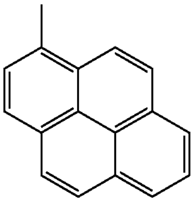 |

-continued
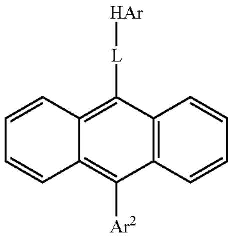
| Compound | HAr | L | Ar² |
| --- | --- | --- | --- |
| 6-7 | 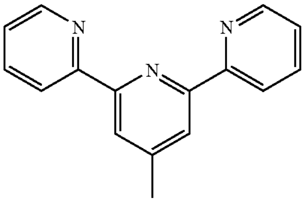 | 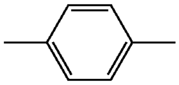 | 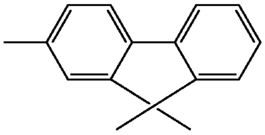 |
| 6-8 | 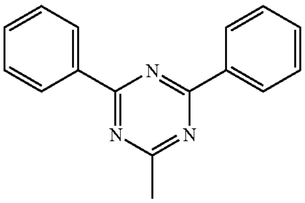 | 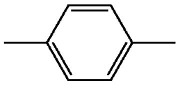 | 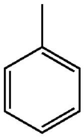 |
| 6-9 | 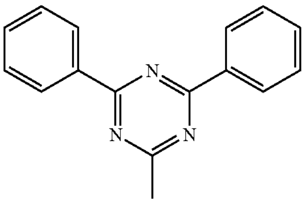 | 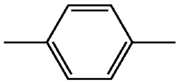 | 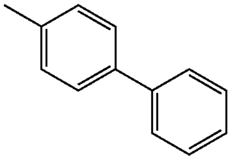 |
| 6-10 | 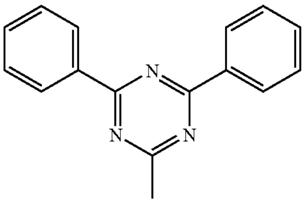 | 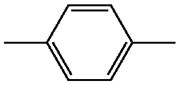 | 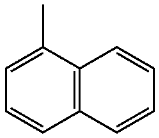 |
| 6-11 | 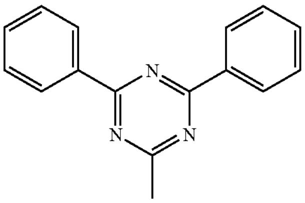 | 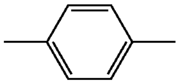 | 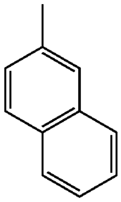 |
| 6-12 | 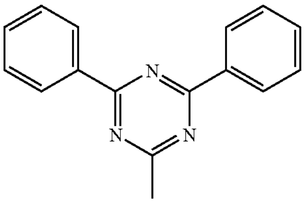 | 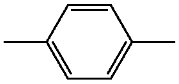 | 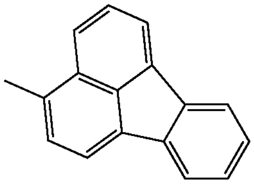 |

-continued
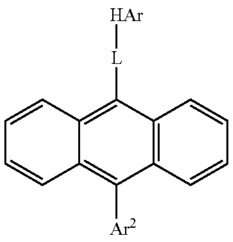
| Compound | HAr | L | $Ar^2$ |
| --- | --- | --- | --- |
| 6-13 | 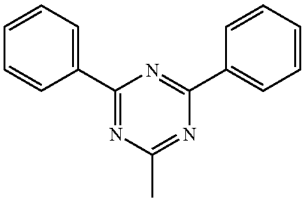 | 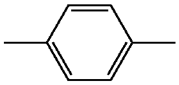 | 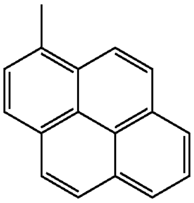 |
| 6-14 | 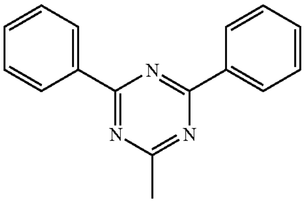 | 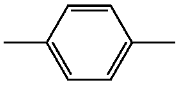 | 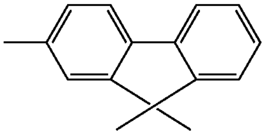 |
| 6-15 | 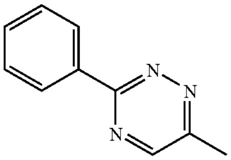 | 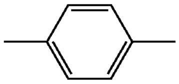 | 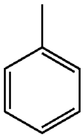 |
| 6-16 | 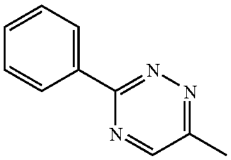 | 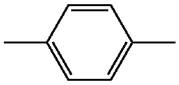 | 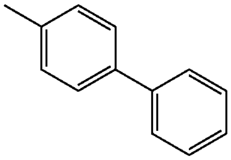 |
| 6-17 | 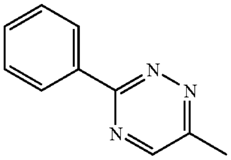 | 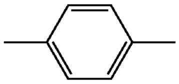 | 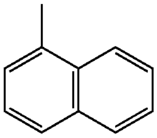 |
| 6-18 | 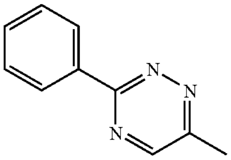 | 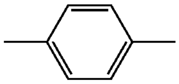 | 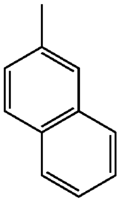 |

-continued
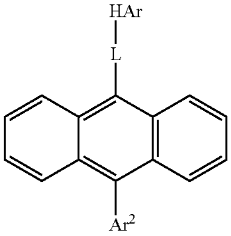
| Compound | HAr | L | $Ar^2$ |
| --- | --- | --- | --- |
| 6-19 | 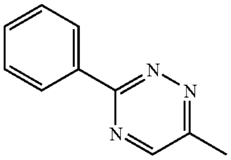 | 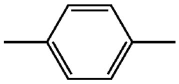 | 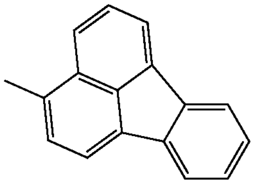 |
| 6-20 | 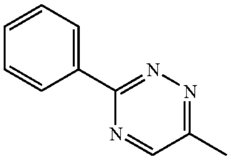 | 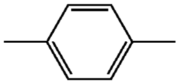 | 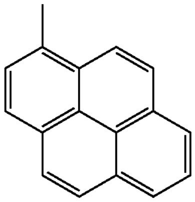 |
| 6-21 | 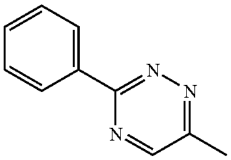 | 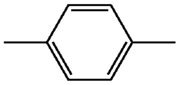 | 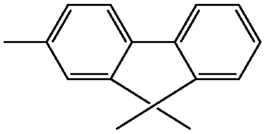 |
| 7-1 | 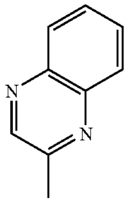 | — | 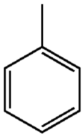 |
| 7-2 | 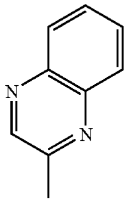 | — | 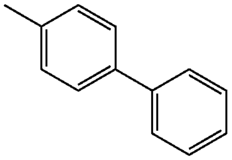 |
| 7-3 | 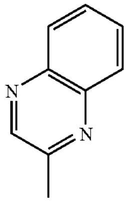 | — | 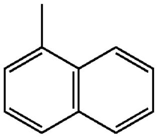 |

-continued
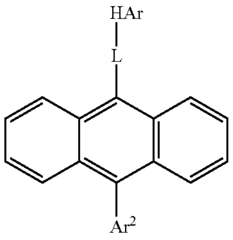
| Compound | HAr | L | $Ar^2$ |
| --- | --- | --- | --- |
| 7-4 | 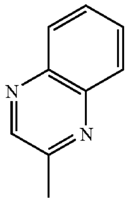 | — | 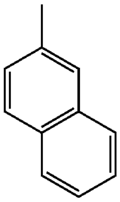 |
| 7-5 | 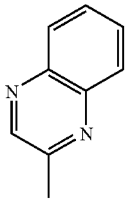 | — | 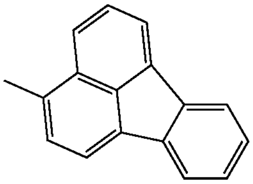 |
| 7-6 | 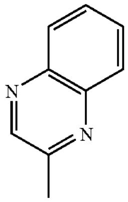 | — | 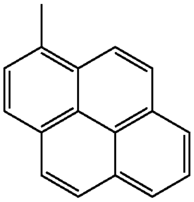 |
| 7-7 | 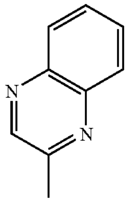 | — | 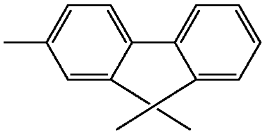 |
| 7-8 | 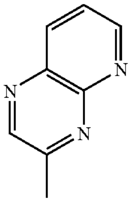 | — | 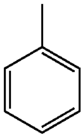 |
| 7-9 | 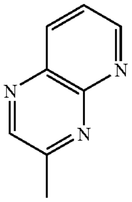 | — | 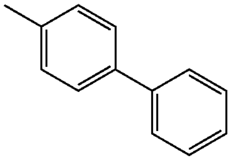 |

-continued
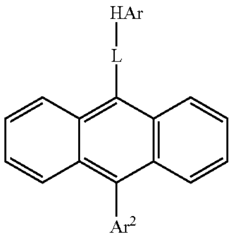
| Compound | HAr | L | $Ar^2$ |
|---|---|---|---|
| 7-10 | 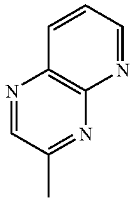 | — | 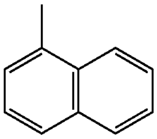 |
| 7-11 | 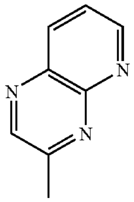 | — | 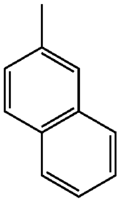 |
| 7-12 | 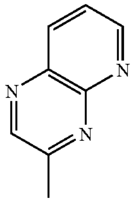 | — | 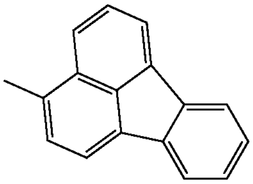 |
| 7-13 | 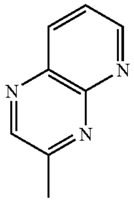 | — | 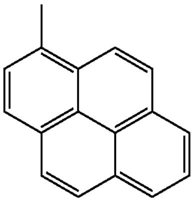 |
| 7-14 | 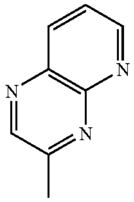 | — | 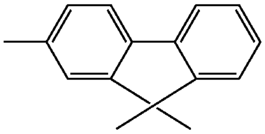 |
| 7-15 | 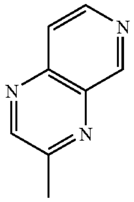 | — | 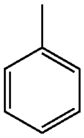 |

-continued
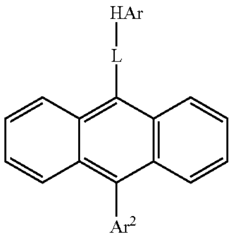
| Compound | HAr | L | Ar$^2$ |
|---|---|---|---|
| 7-16 | 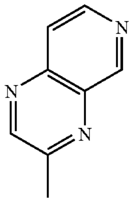 | — | 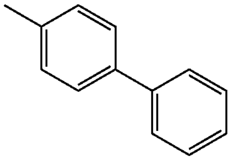 |
| 7-17 | 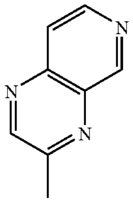 | — | 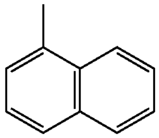 |
| 7-18 | 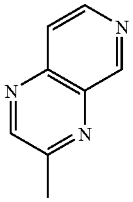 | — | 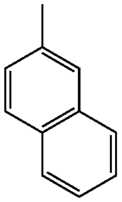 |
| 7-19 | 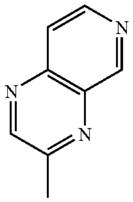 | — | 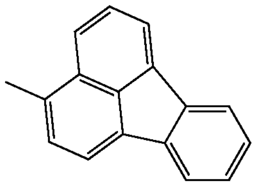 |
| 7-20 | 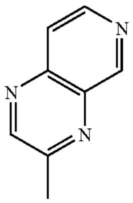 | — | 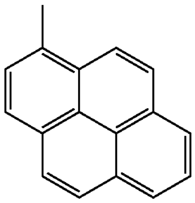 |
| 7-21 | 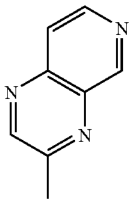 | — | 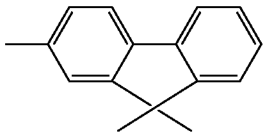 |

-continued
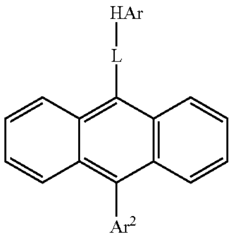
| Compound | HAr | L | $Ar^2$ |
|---|---|---|---|
| 8-1 | 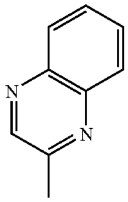 | 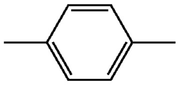 | 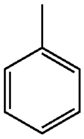 |
| 8-2 | 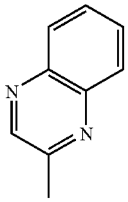 | 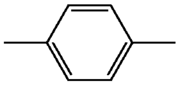 | 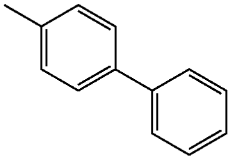 |
| 8-3 | 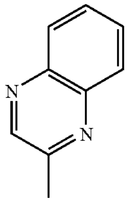 | 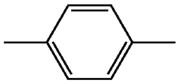 | 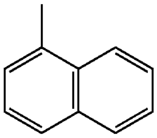 |
| 8-4 | 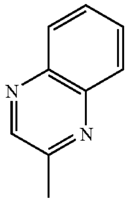 | 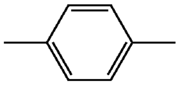 | 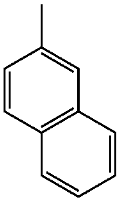 |
| 8-5 | 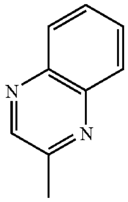 | 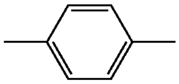 | 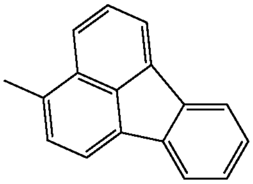 |
| 8-6 | 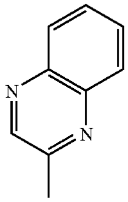 | 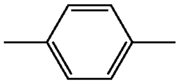 | 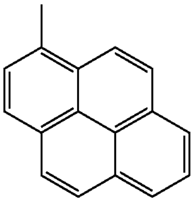 |

-continued
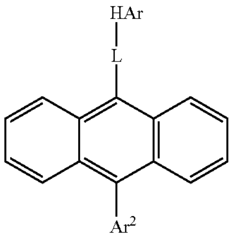
| Compound | HAr | L | Ar$^2$ |
|---|---|---|---|
| 8-7 | 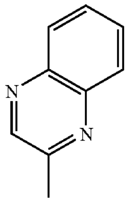 | 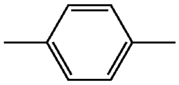 | 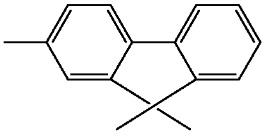 |
| 8-8 | 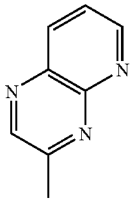 | 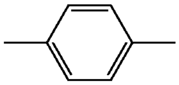 | 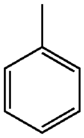 |
| 8-9 | 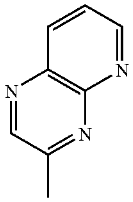 | 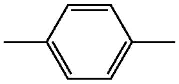 | 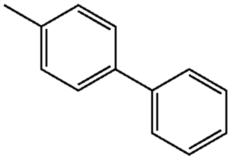 |
| 8-10 | 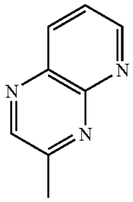 | 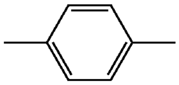 | 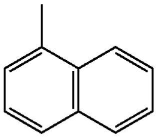 |
| 8-11 | 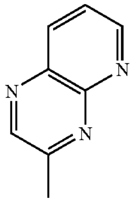 | 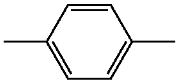 | 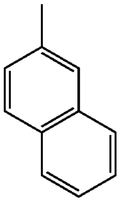 |
| 8-12 | 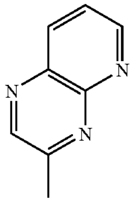 | 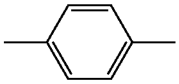 | 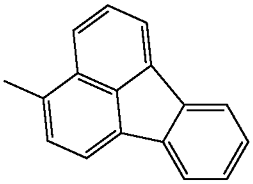 |

-continued
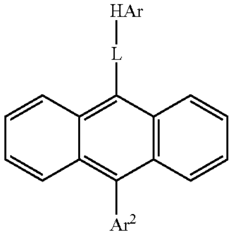
| Compound | HAr | L | $Ar^2$ |
| --- | --- | --- | --- |
| 8-13 | 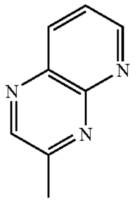 | 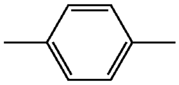 | 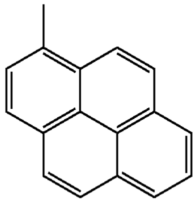 |
| 8-14 | 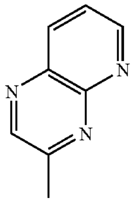 | 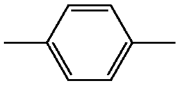 | 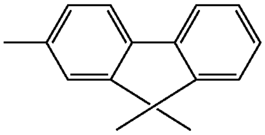 |
| 8-15 | 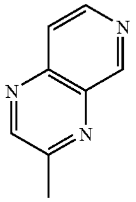 | 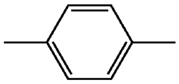 | 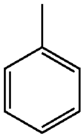 |
| 8-16 | 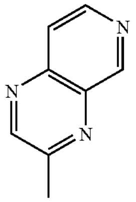 | 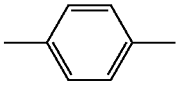 | 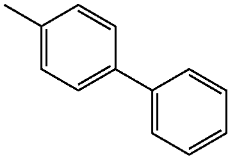 |
| 8-17 | 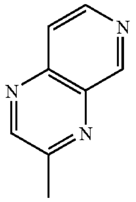 | 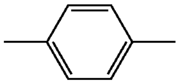 | 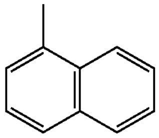 |
| 8-18 | 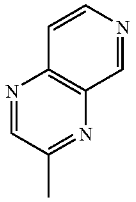 | 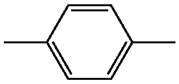 | 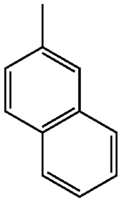 |

-continued
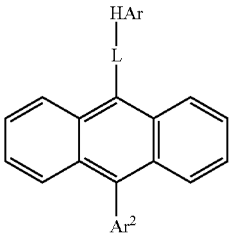
| Compound | HAr | L | Ar^2 |
|---|---|---|---|
| 8-19 | 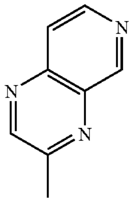 | 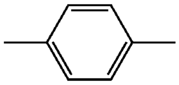 | 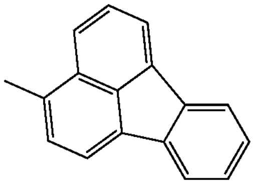 |
| 8-20 | 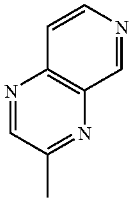 | 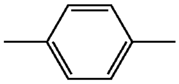 | 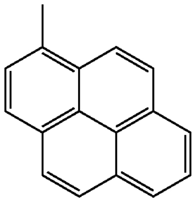 |
| 8-21 | 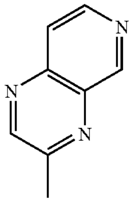 | 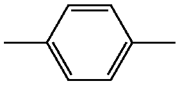 | 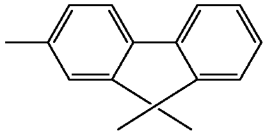 |
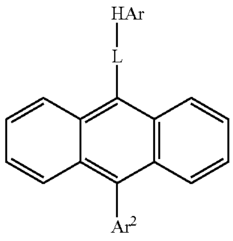
| Compound | HAr | L | Ar^2 |
|---|---|---|---|
| 9-1 | 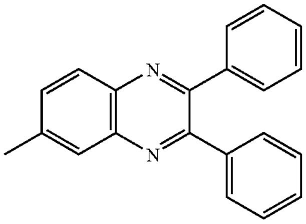 | — | 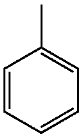 |

-continued
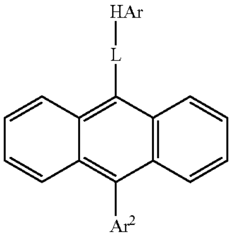
| Compound | HAr | L | $Ar^2$ |
| --- | --- | --- | --- |
| 9-2 | 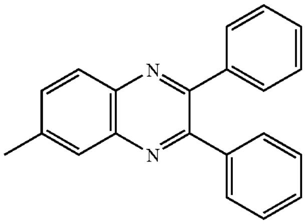 | — | 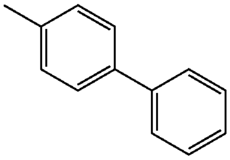 |
| 9-3 | 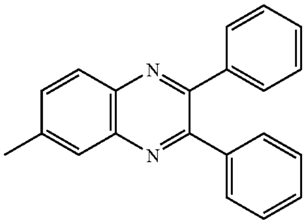 | — | 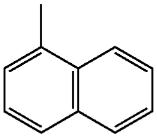 |
| 9-4 | 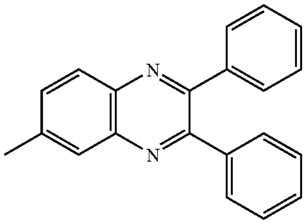 | — | 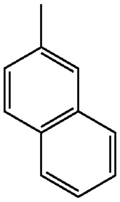 |
| 9-5 | 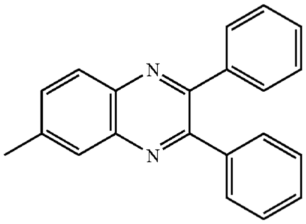 | — | 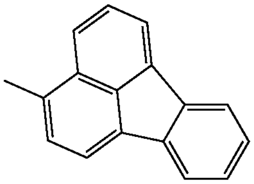 |
| 9-6 | 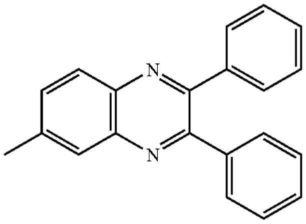 | — | 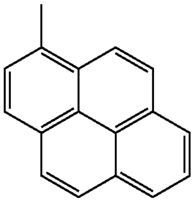 |

-continued
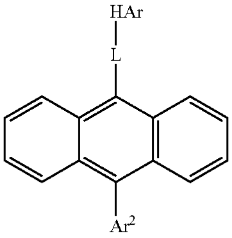
| Compound | HAr | L | $Ar^2$ |
| --- | --- | --- | --- |
| 9-7 | 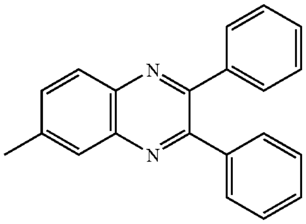 | — | 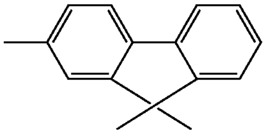 |
| 9-8 | 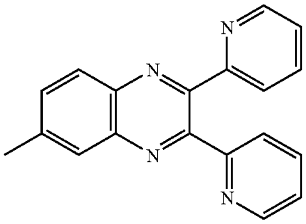 | — | 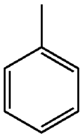 |
| 9-9 | 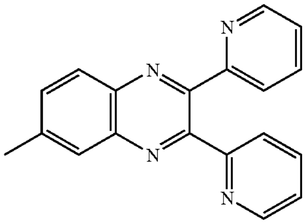 | — | 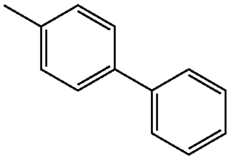 |
| 9-10 | 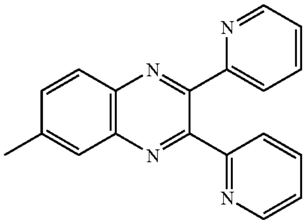 | — | 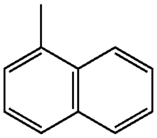 |
| 9-11 | 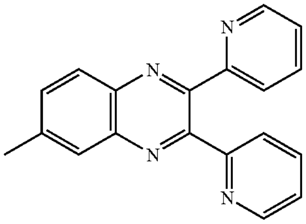 | — | 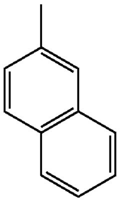 |

-continued
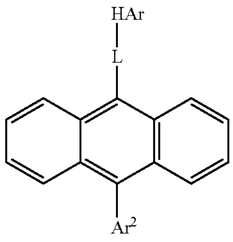
| Compound | HAr | L | $Ar^2$ |
| --- | --- | --- | --- |
| 9-12 | 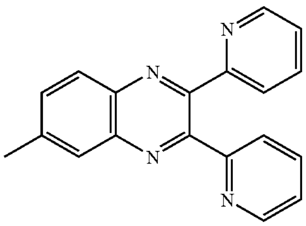 | — | 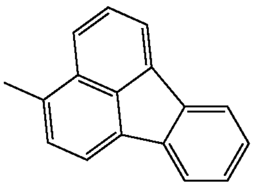 |
| 9-13 | 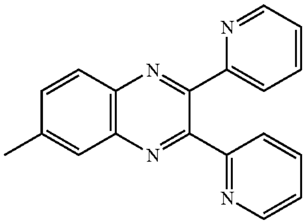 | — | 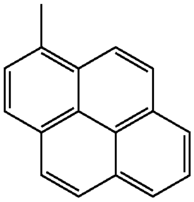 |
| 9-14 | 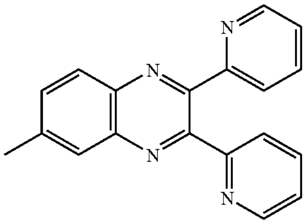 | — | 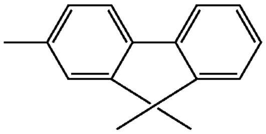 |
| 9-15 | 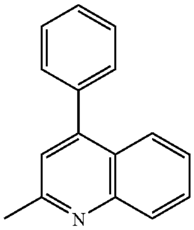 | — | 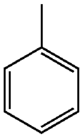 |
| 9-16 | 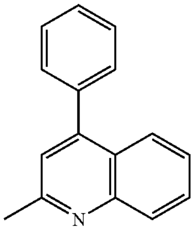 | — | 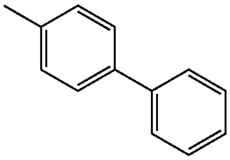 |

-continued
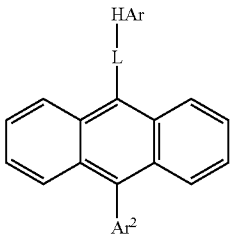
| Compound | HAr | L | $Ar^2$ |
| --- | --- | --- | --- |
| 9-17 | 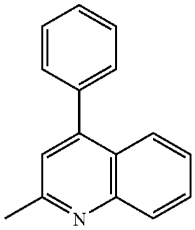 | — | 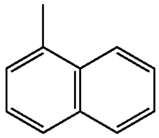 |
| 9-18 | 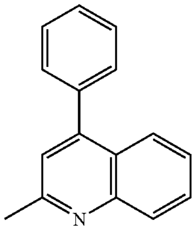 | — | 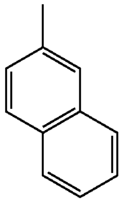 |
| 9-19 | 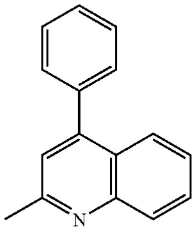 | — | 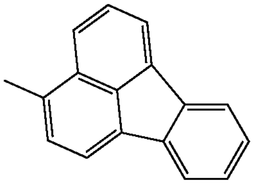 |
| 9-20 | 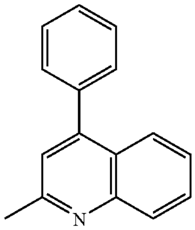 | — | 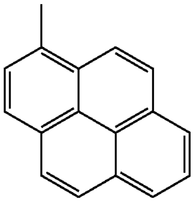 |
| 9-21 | 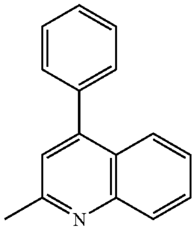 | — | 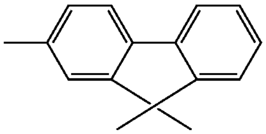 |

-continued
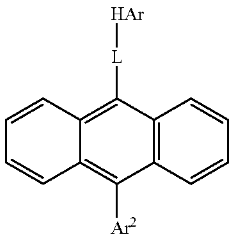
| Compound | HAr | L | $Ar^2$ |
| --- | --- | --- | --- |
| 10-1 | 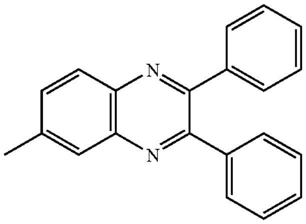 | 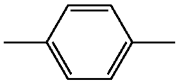 | 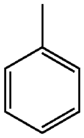 |
| 10-2 | 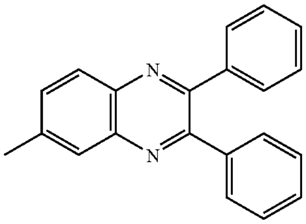 | 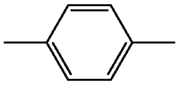 | 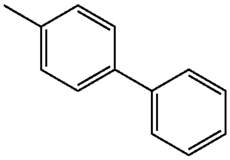 |
| 10-3 | 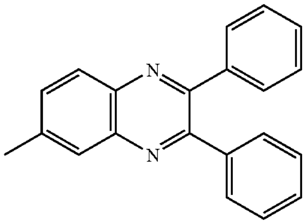 | 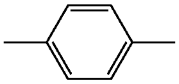 | 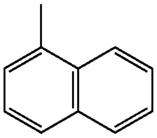 |
| 10-4 | 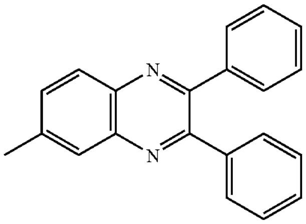 | 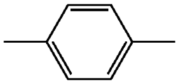 | 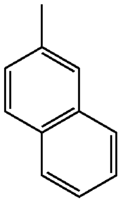 |
| 10-5 | 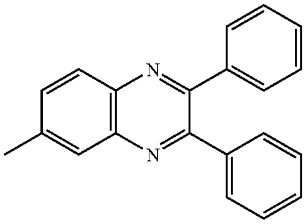 | 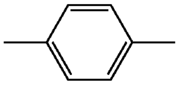 | 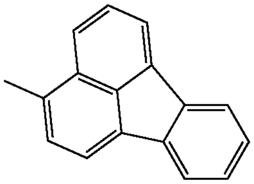 |

-continued
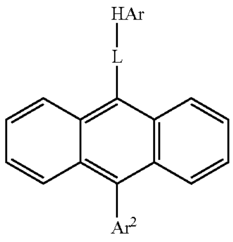
| Compound | HAr | L | $Ar^2$ |
| --- | --- | --- | --- |
| 10-6 | 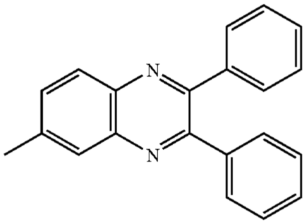 | 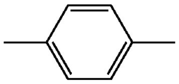 | 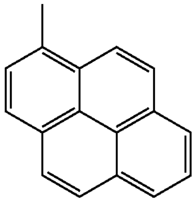 |
| 10-7 | 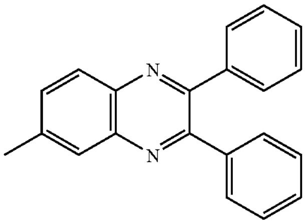 | 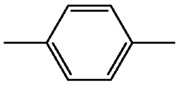 | 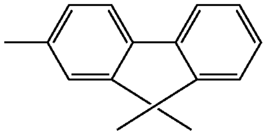 |
| 10-8 | 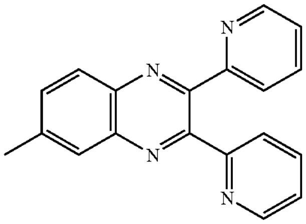 | 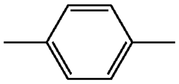 | 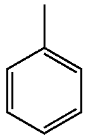 |
| 10-9 | 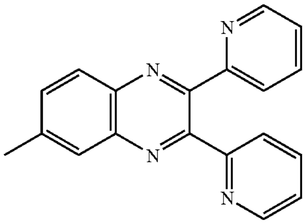 | 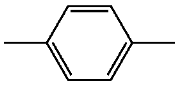 | 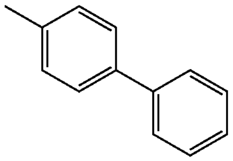 |
| 10-10 | 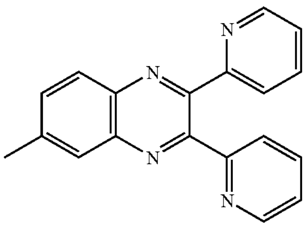 | 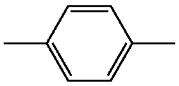 | 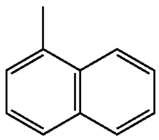 |

-continued
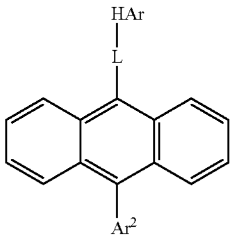
| Compound | HAr | L | $Ar^2$ |
| --- | --- | --- | --- |
| 10-11 | 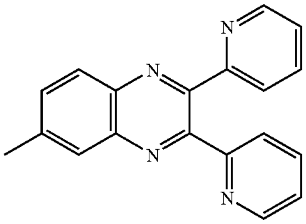 | 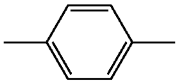 | 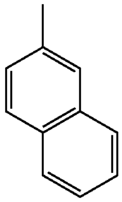 |
| 10-12 | 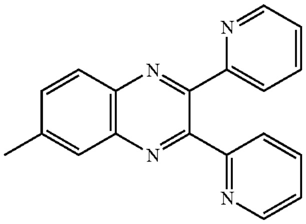 | 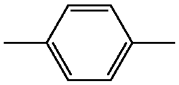 | 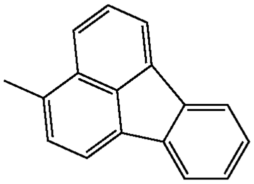 |
| 10-13 | 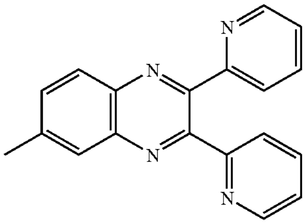 | 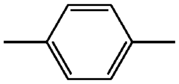 | 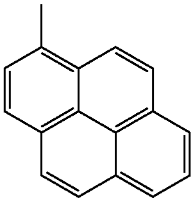 |
| 10-14 | 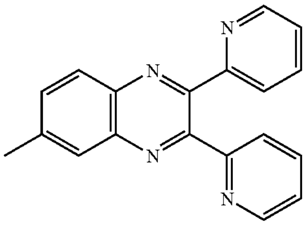 | 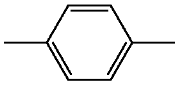 | 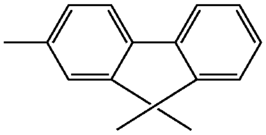 |
| 10-15 | 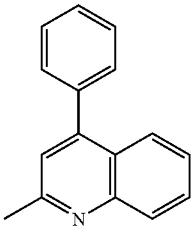 | 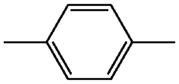 | 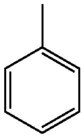 |

-continued
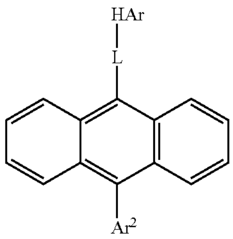
| Compound | HAr | L | Ar$^2$ |
|---|---|---|---|
| 10-16 | 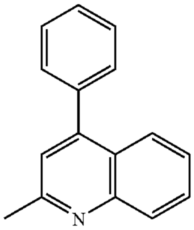 | 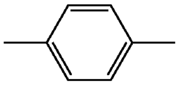 | 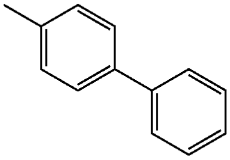 |
| 10-17 | 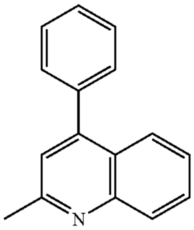 | 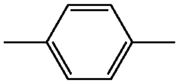 | 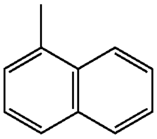 |
| 10-18 | 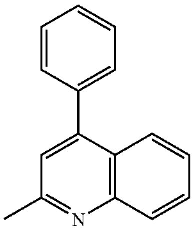 | 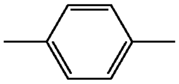 | 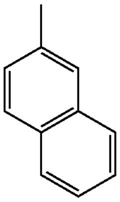 |
| 10-19 | 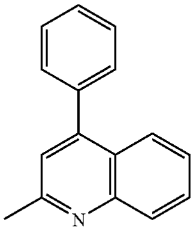 | 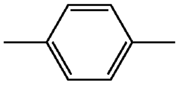 | 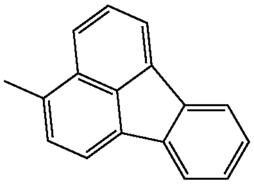 |
| 10-20 | 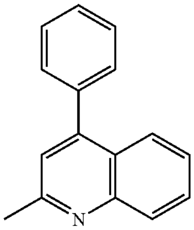 | 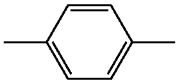 | 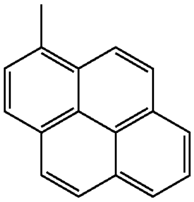 |

-continued
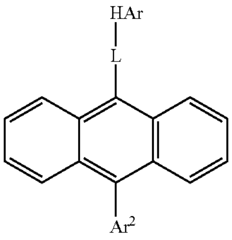
| Compound | HAr | L | $Ar^2$ |
| --- | --- | --- | --- |
| 10-21 | 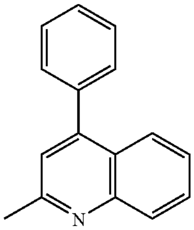 | 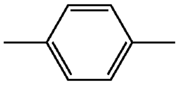 | 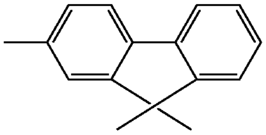 |
| 11-1 | 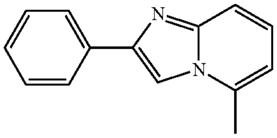 | — | 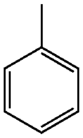 |
| 11-2 | 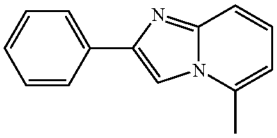 | — | 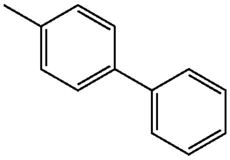 |
| 11-3 | 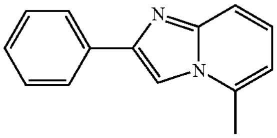 | — | 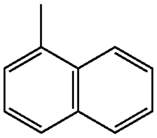 |
| 11-4 | 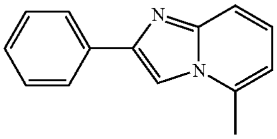 | — | 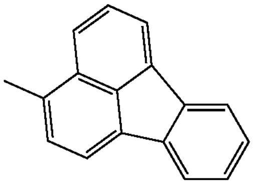 |
| 11-5 | 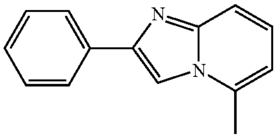 | — | 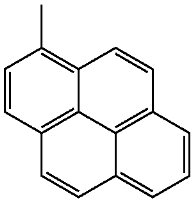 |
| 11-6 | 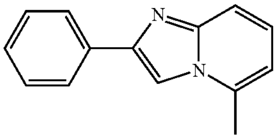 | — | 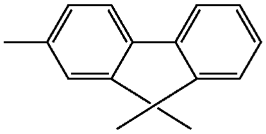 |

-continued
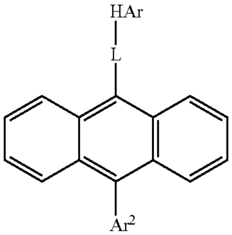
| Compound | HAr | L | $Ar^2$ |
|---|---|---|---|
| 11-7 | 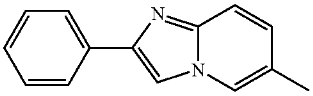 | — | 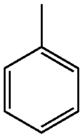 |
| 11-8 | 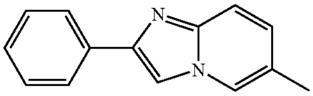 | — | 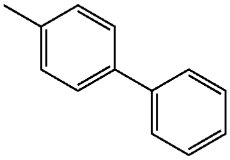 |
| 11-9 | 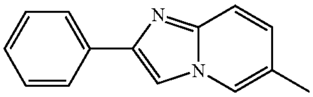 | — | 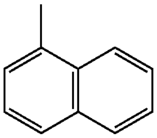 |
| 11-10 | 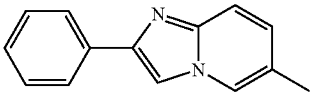 | — | 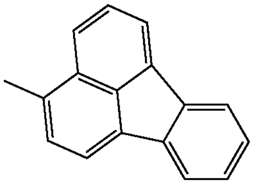 |
| 11-11 | 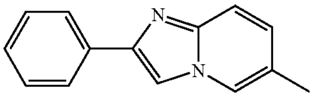 | — | 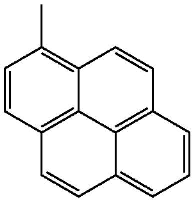 |
| 11-12 | 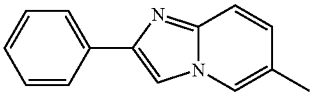 | — | 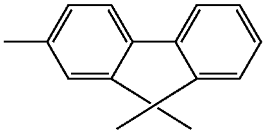 |
| 12-1 | 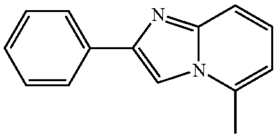 | 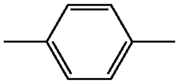 | 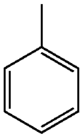 |

-continued
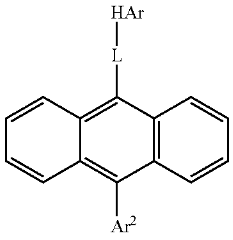
| Compound | HAr | L | $Ar^2$ |
| --- | --- | --- | --- |
| 12-2 | 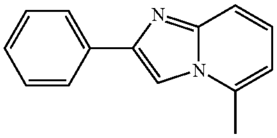 | 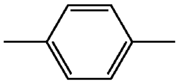 | 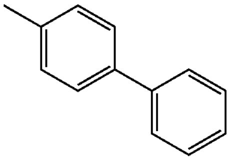 |
| 12-3 | 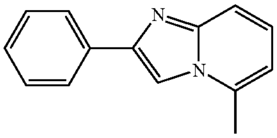 | 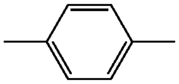 | 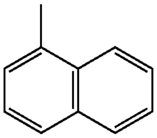 |
| 12-4 | 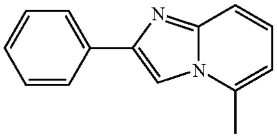 | 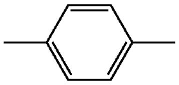 | 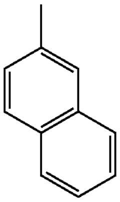 |
| 12-5 | 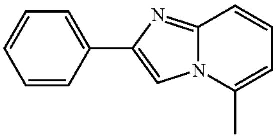 | 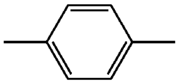 | 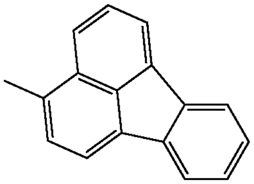 |
| 12-6 | 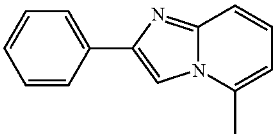 | 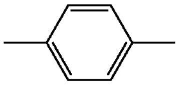 | 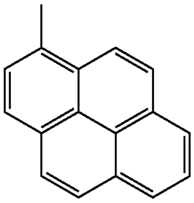 |
| 12-7 | 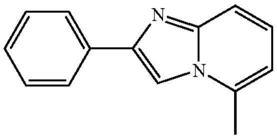 | 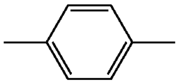 | 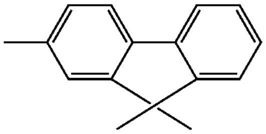 |
| 12-8 | 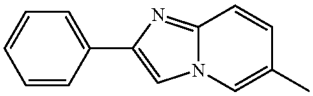 | 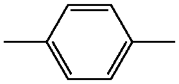 | 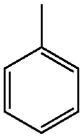 |

-continued
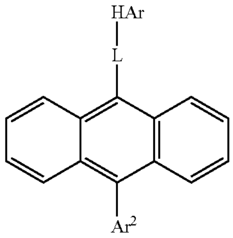
| Compound | HAr | L | $Ar^2$ |
|---|---|---|---|
| 12-9 | 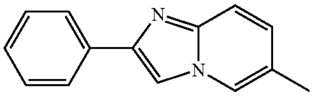 | 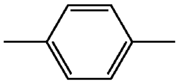 | 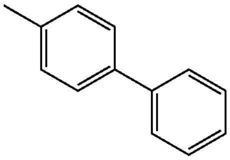 |
| 12-10 | 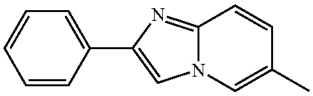 | 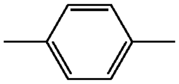 | 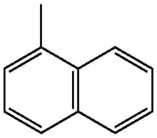 |
| 12-11 | 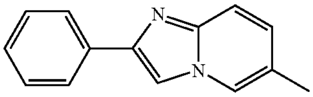 | 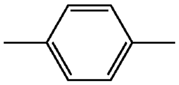 | 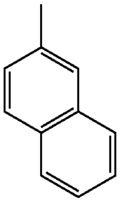 |
| 12-12 | 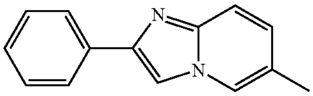 | 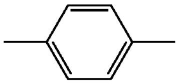 | 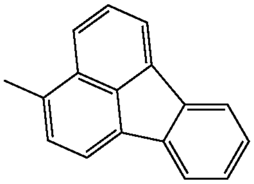 |
| 12-13 | 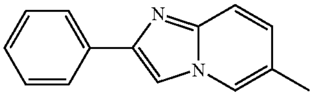 | 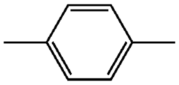 | 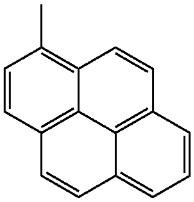 |
| 12-14 | 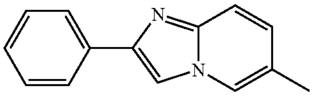 | 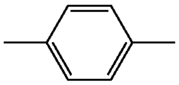 | 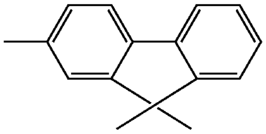 |
| 13-1 | 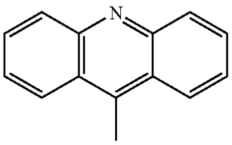 | — | 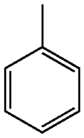 |

-continued
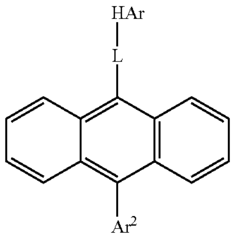
| Compound | HAr | L | Ar$^2$ |
| --- | --- | --- | --- |
| 13-2 | 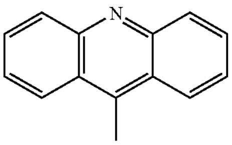 | — | 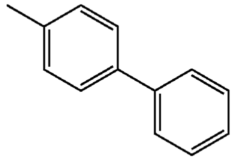 |
| 13-3 | 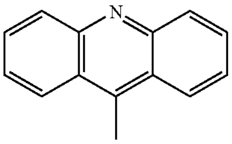 | — | 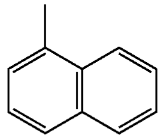 |
| 13-4 | 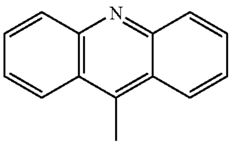 | — | 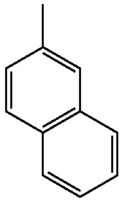 |
| 13-5 | 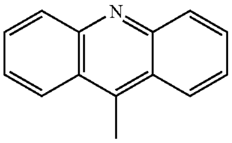 | — | 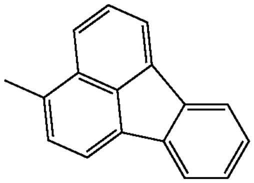 |
| 13-6 | 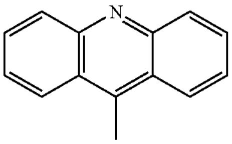 | — | 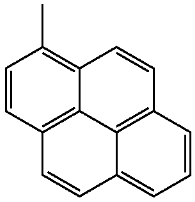 |
| 13-7 | 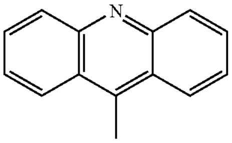 | — | 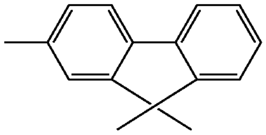 |
| 13-8 | 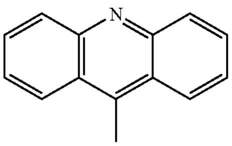 | — | 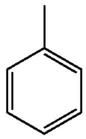 |

-continued
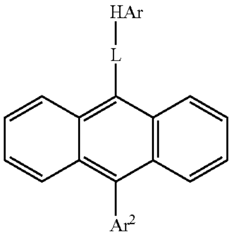
| Compound | HAr | L | $Ar^2$ |
| --- | --- | --- | --- |
| 13-9 | 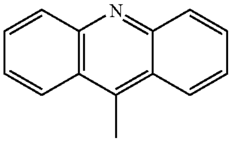 | 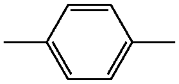 | 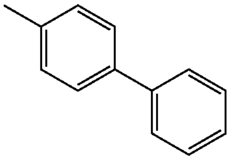 |
| 13-10 | 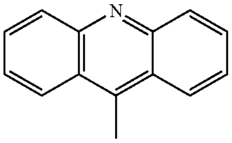 | 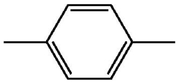 | 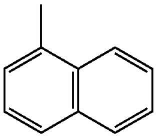 |
| 13-11 | 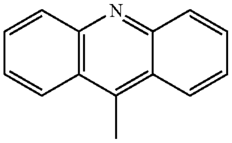 | 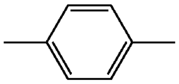 | 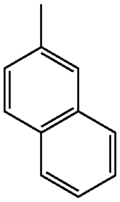 |
| 13-12 | 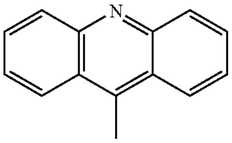 | 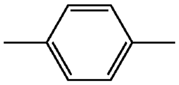 | 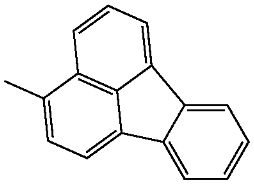 |
| 13-13 | 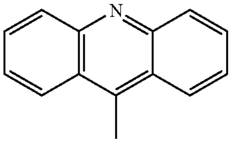 | 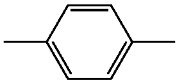 | 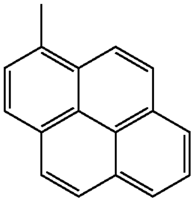 |
| 13-14 | 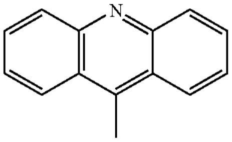 | 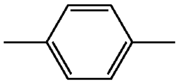 | 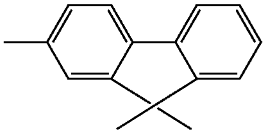 |

-continued
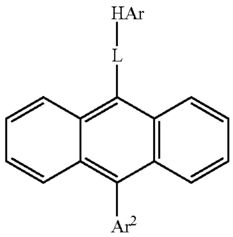
| Compound | HAr | L | $Ar^2$ |
|---|---|---|---|
| 13-15 | 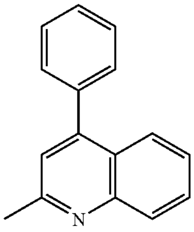 | 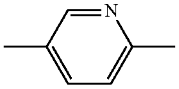 | 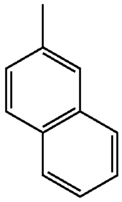 |
| 13-16 | 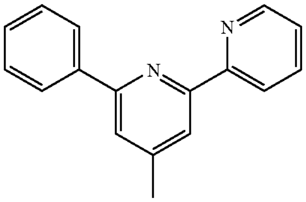 | — | 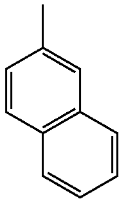 |
| | HAr—L—$Ar^1$—$Ar^2$ | | | |
|---|---|---|---|---|
| | HAr | L | $Ar^1$ | $Ar^2$ |
| 14-1 | 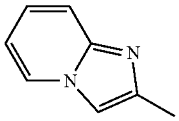 | 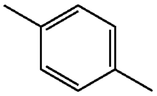 | 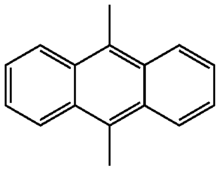 | 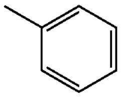 |
| 2 | 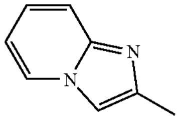 | 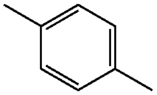 | 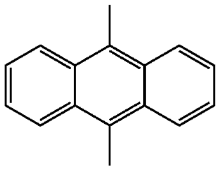 | 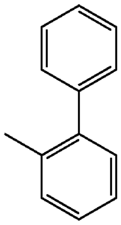 |
| 3 | 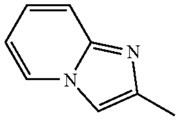 | 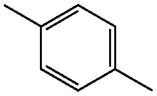 | 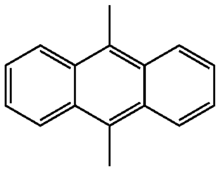 | 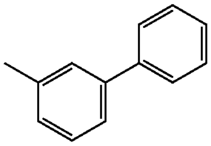 |

-continued
| | | | | |
|---|---|---|---|---|
| 4 | 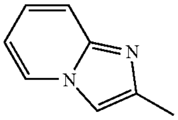 | 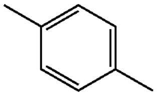 | 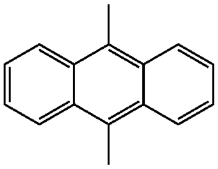 | 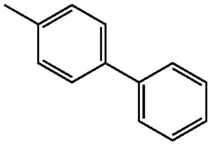 |
| 5 | 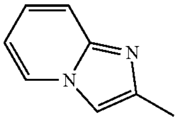 | 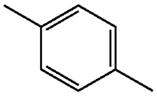 | 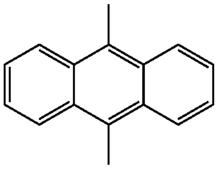 | 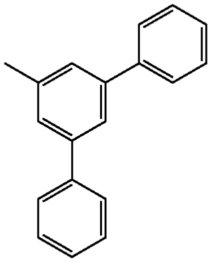 |
| 6 | 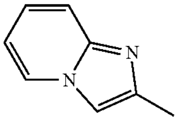 | 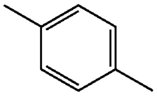 | 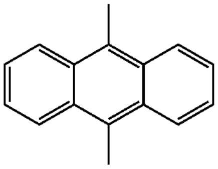 | 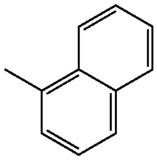 |
| 7 | 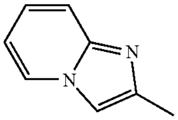 | 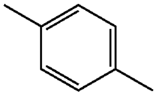 | 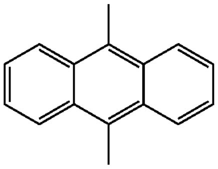 | 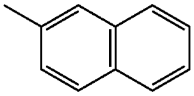 |
| 8 | 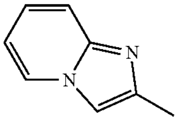 | 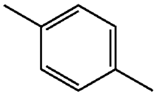 | 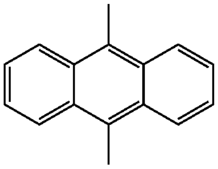 | 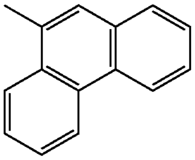 |
| 9 | 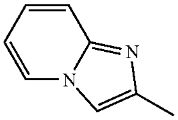 | 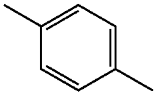 | 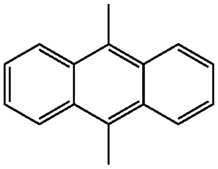 | 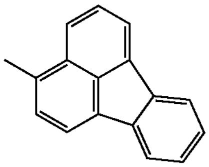 |
| 10 | 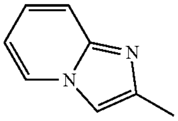 | 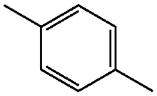 | 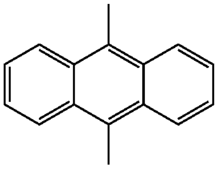 | 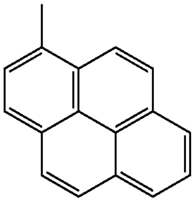 |
| 11 | 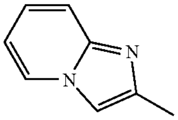 | 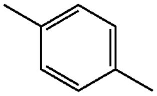 | 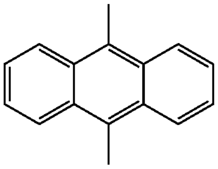 | 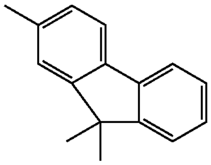 |

-continued
| | | | | |
|---|---|---|---|---|
| 15-1 | 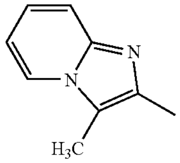 | 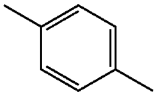 | 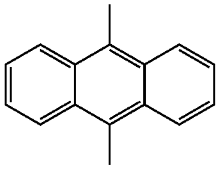 | 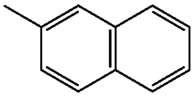 |
| 2 | 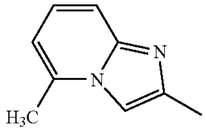 | 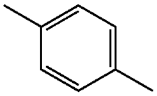 | 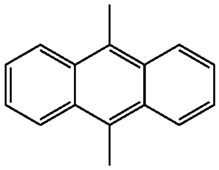 | 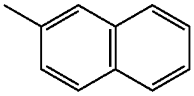 |
| 3 | 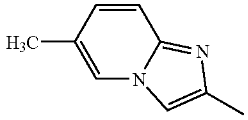 | 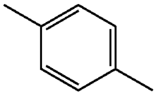 | 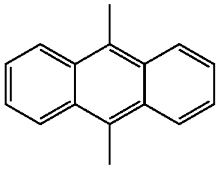 | 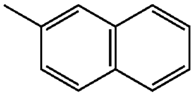 |
| 4 | 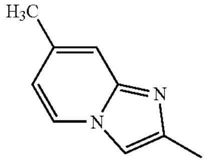 | 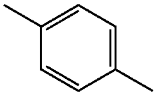 | 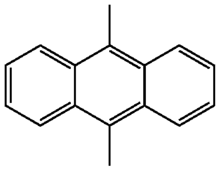 | 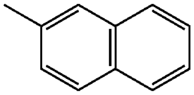 |
| 5 | 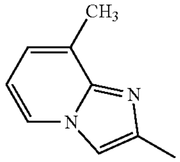 | 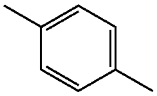 | 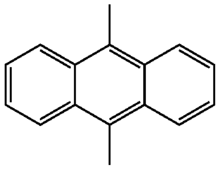 | 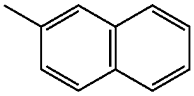 |
| 6 | 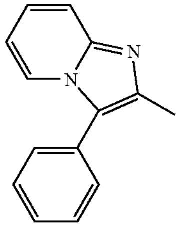 | 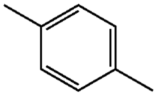 | 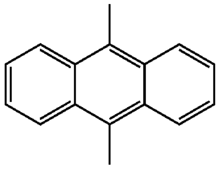 | 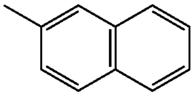 |
| 7 | 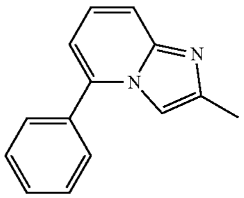 | 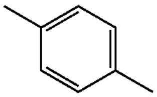 | 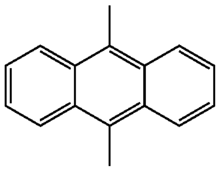 | 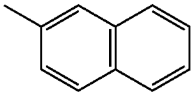 |
| 8 | 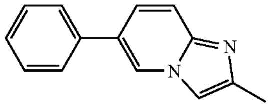 | 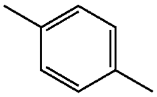 | 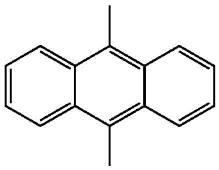 | 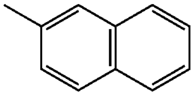 |

-continued
| | | | | |
|---|---|---|---|---|
| 9 | 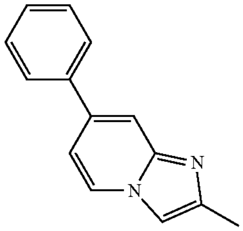 | 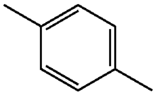 | 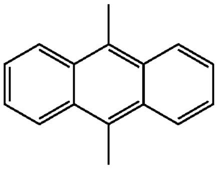 | 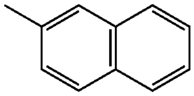 |
| 10 | 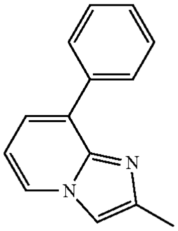 | 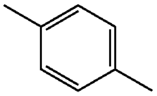 | 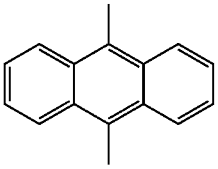 | 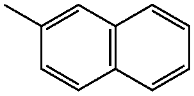 |
| 16-1 | 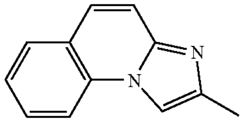 | 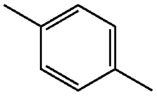 | 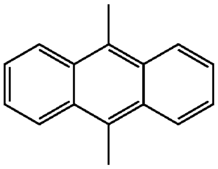 | 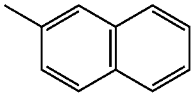 |
| 2 | 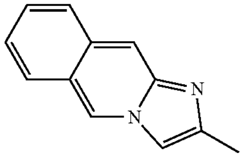 | 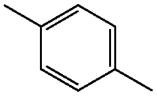 | 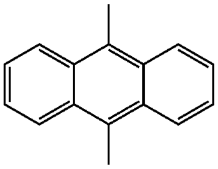 | 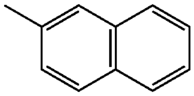 |
| 3 | 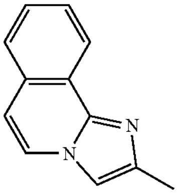 | 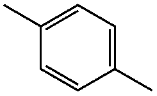 | 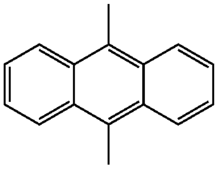 | 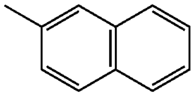 |
| 4 | 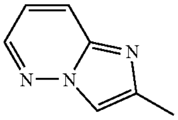 | 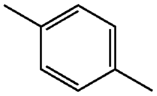 | 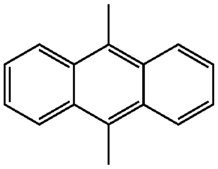 | 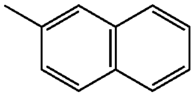 |
| 5 | 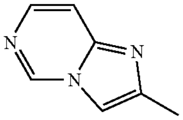 | 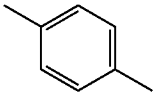 | 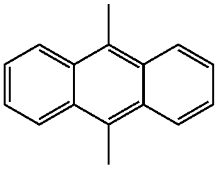 | 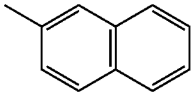 |
| 6 | 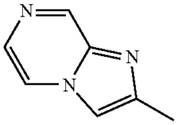 | 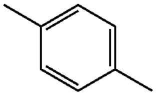 | 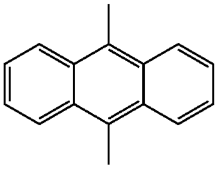 | 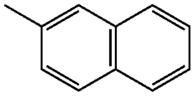 |

-continued
7 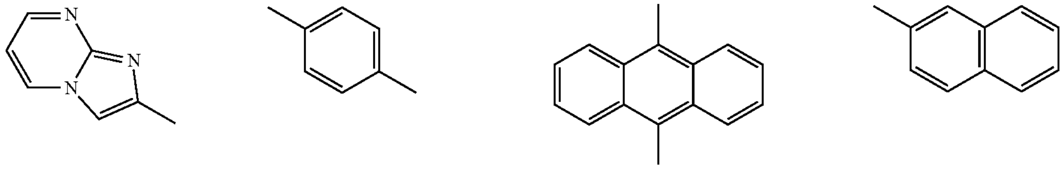
17-1 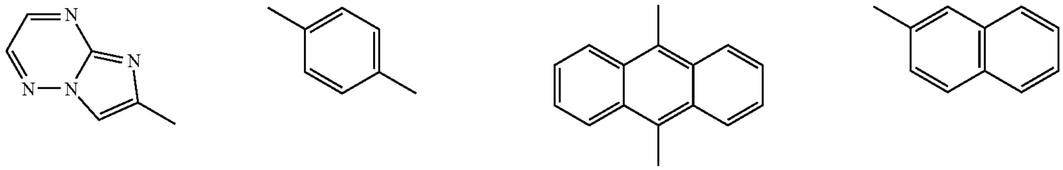
2 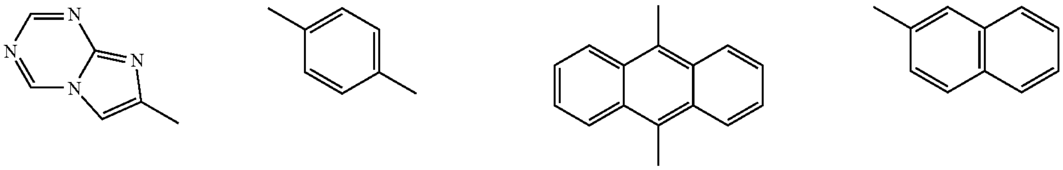
3 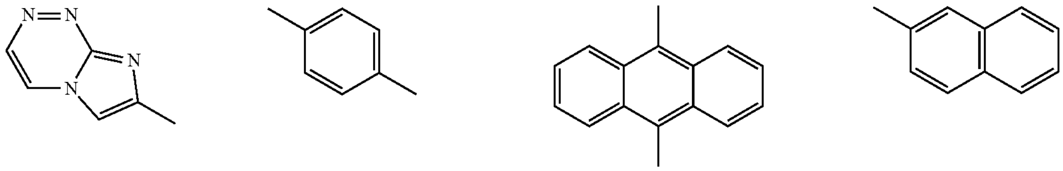
4 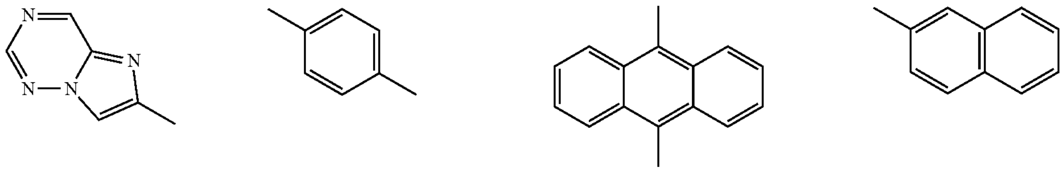
5 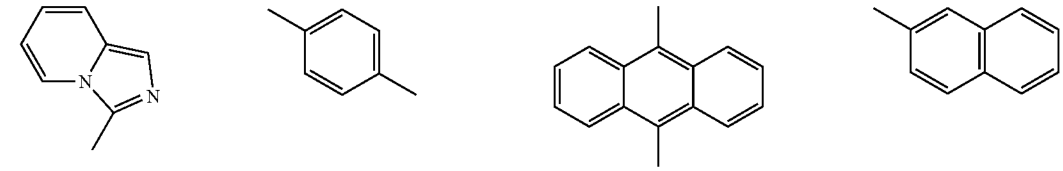
6 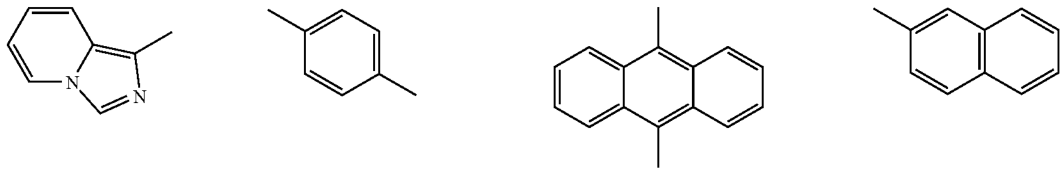
7 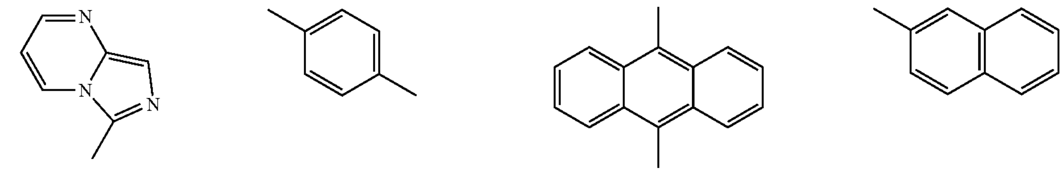
8 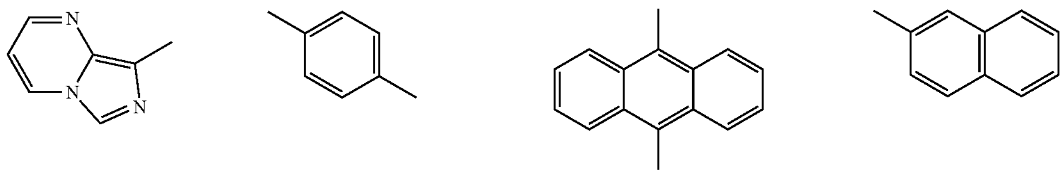

-continued
| | | | | |
|---|---|---|---|---|
| 9 | 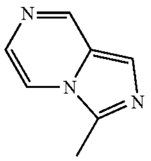 | 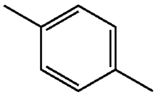 | 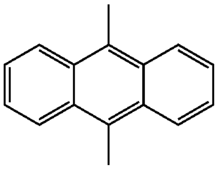 | 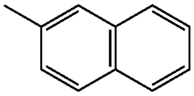 |
| 10 | 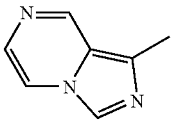 | 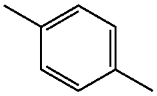 | 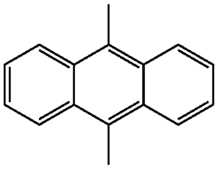 | 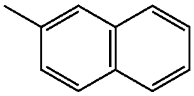 |
| 11 | 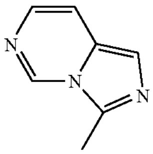 | 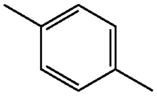 | 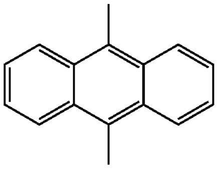 | 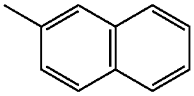 |
| 12 | 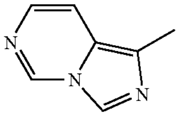 | 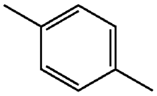 | 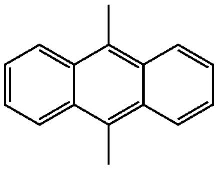 | 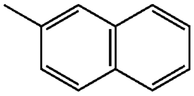 |
| 18-1 | 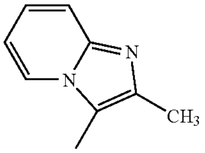 | 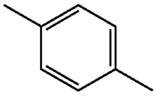 | 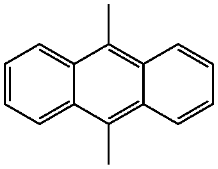 | 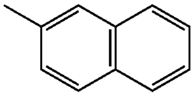 |
| 2 | 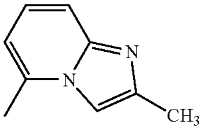 | 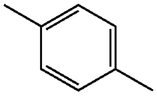 | 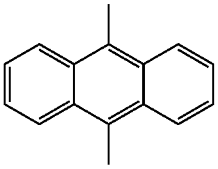 | 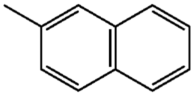 |
| 3 | 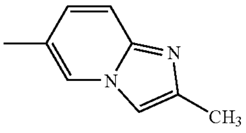 | 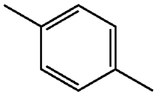 | 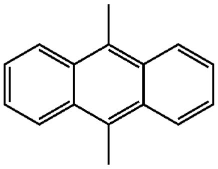 | 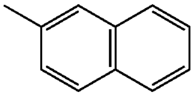 |
| 4 | 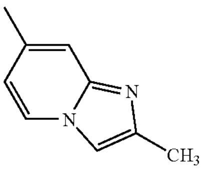 | 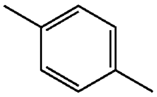 | 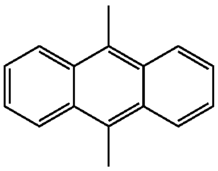 | 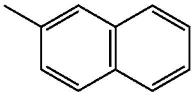 |

-continued
| | | | | |
|---|---|---|---|---|
| 5 | 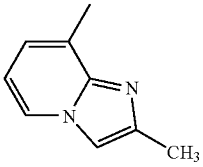 | 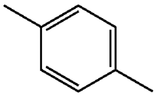 | 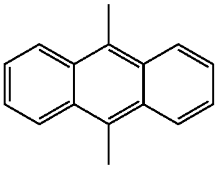 | 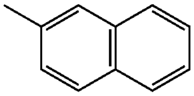 |
| 6 | 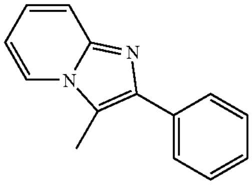 | 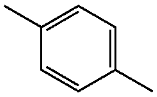 | 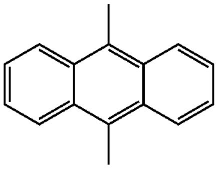 | 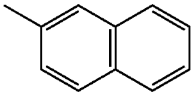 |
| 7 | 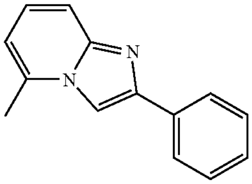 | 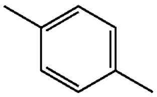 | 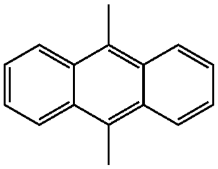 | 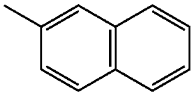 |
| 8 | 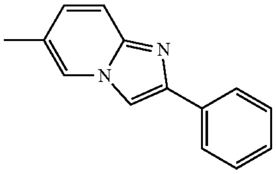 | 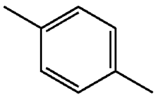 | 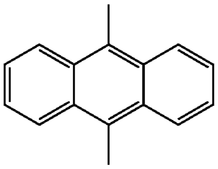 | 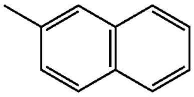 |
| 9 | 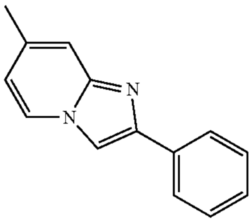 | 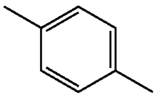 | 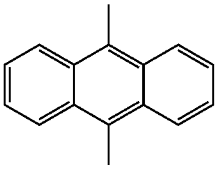 | 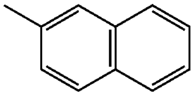 |
| 10 | 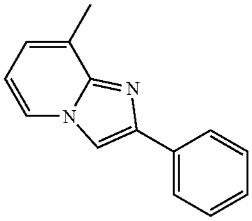 | 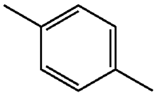 | 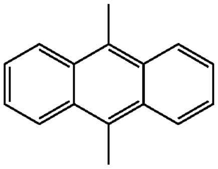 | 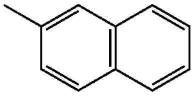 |
| 19-1 | 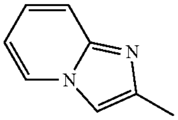 | 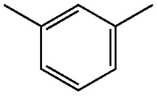 | 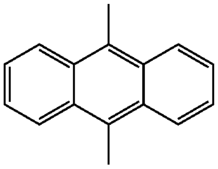 | 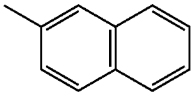 |
| 2 | 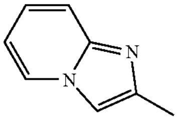 | 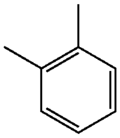 | 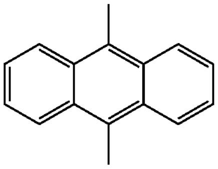 | 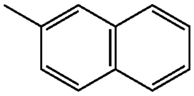 |

-continued
| | | | | |
|---|---|---|---|---|
| 3 | 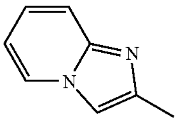 | 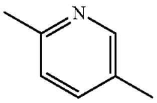 | 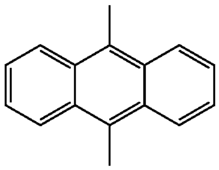 | 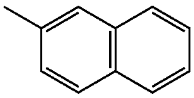 |
| 4 | 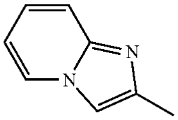 | 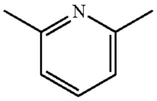 | 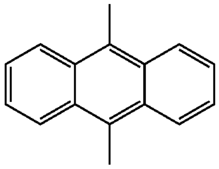 | 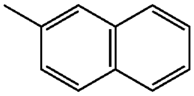 |
| 5 | 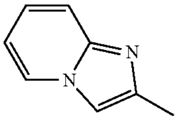 | 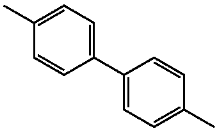 | 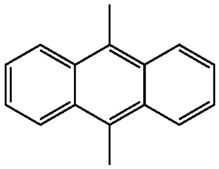 | 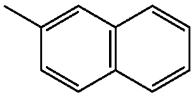 |
| 6 | 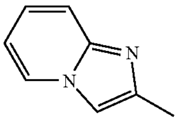 | 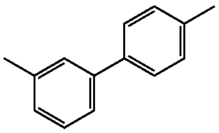 | 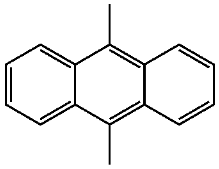 | 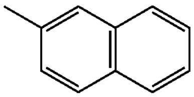 |
| 7 | 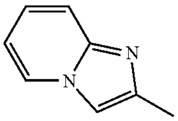 | 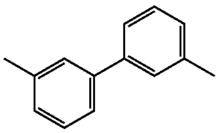 | 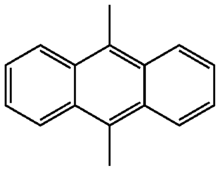 | 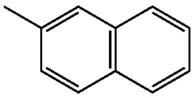 |
| 8 | 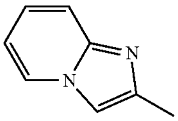 | 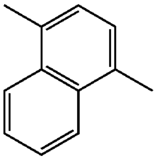 | 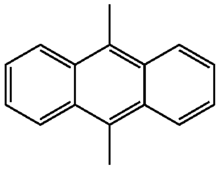 | 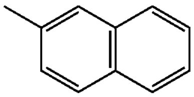 |
| 9 | 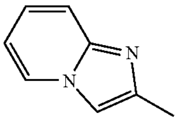 | 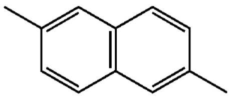 | 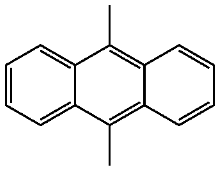 | 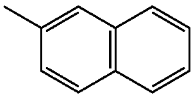 |
| 10 | 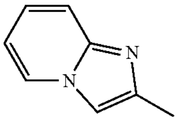 | 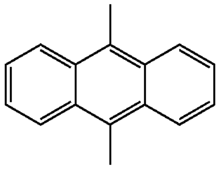 | 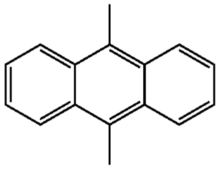 | 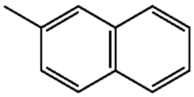 |

-continued
20-1 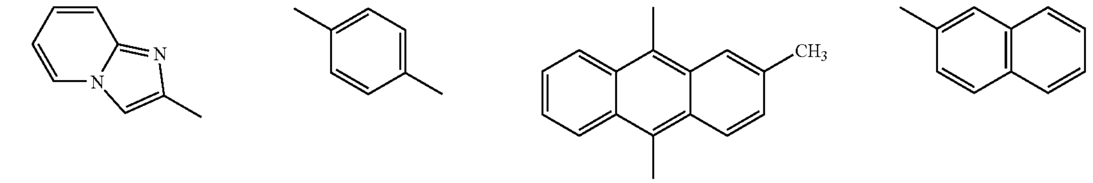
2 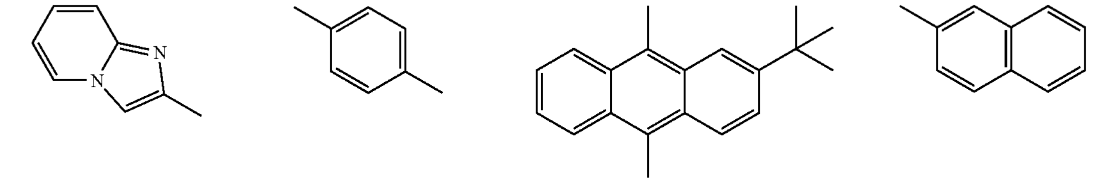
3 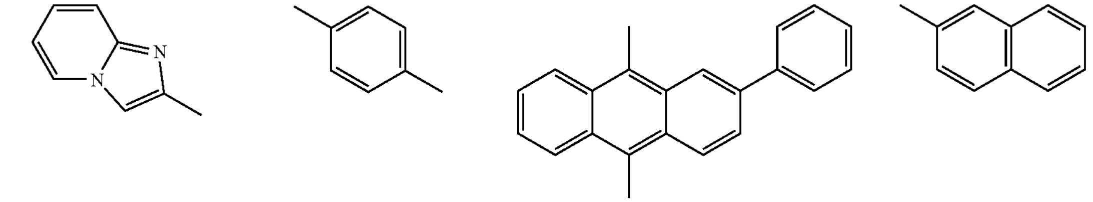
4 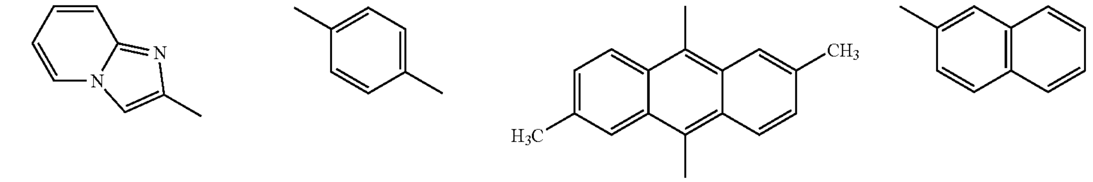
5 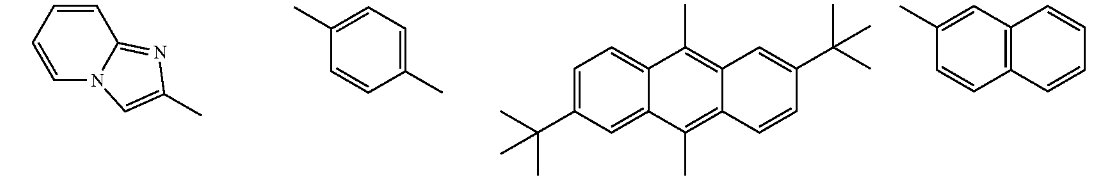
6 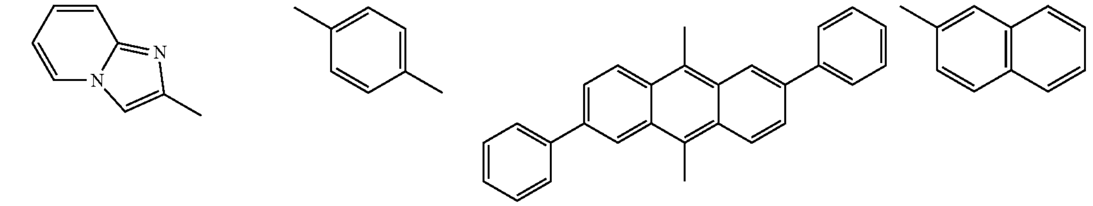
21-1 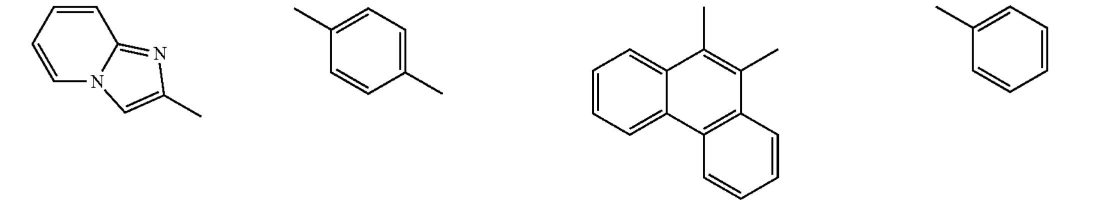
2 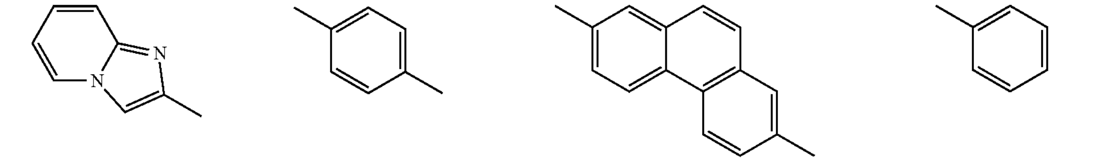

-continued
| | | | | |
|---|---|---|---|---|
| 3 | 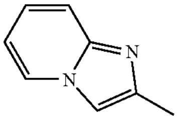 | 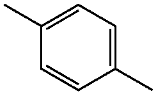 | 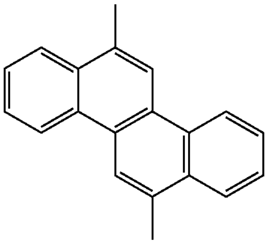 | 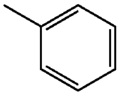 |
| 4 | 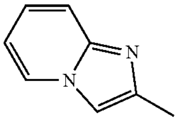 | 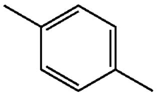 | 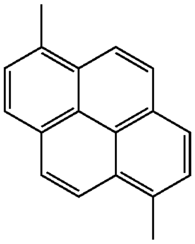 | 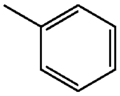 |
| 5 | 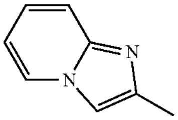 | 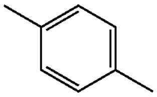 | 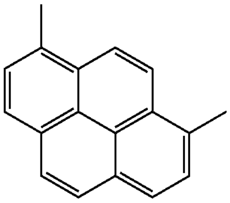 | 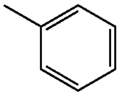 |
| 6 | 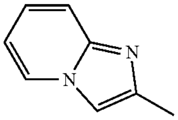 | 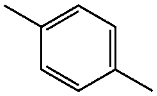 | 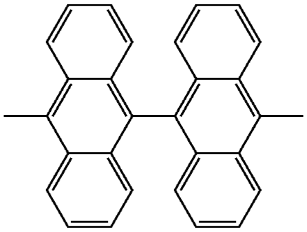 | 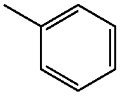 |
| 7 | 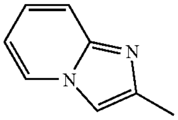 | 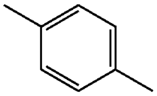 | 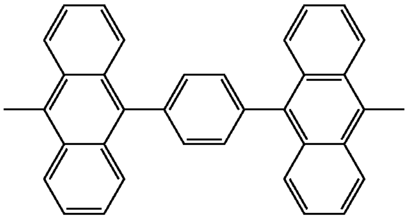 | 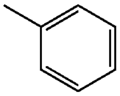 |
HAr—$Ar^1$—$Ar^2$
| | HAr | $Ar^1$ | $Ar^2$ |
|---|---|---|---|
| 22-1 | 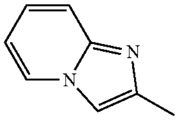 | 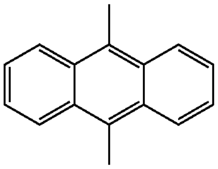 | 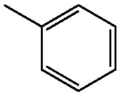 |

-continued
| | | | |
|---|---|---|---|
| 2 | 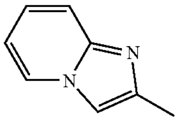 | 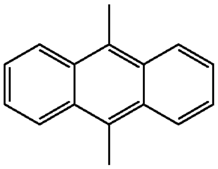 | 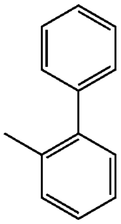 |
| 3 | 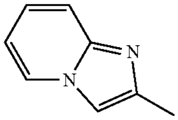 | 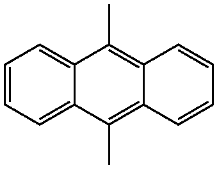 | 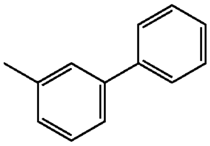 |
| 4 | 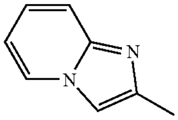 | 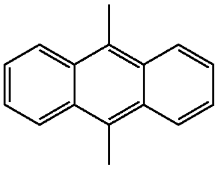 | 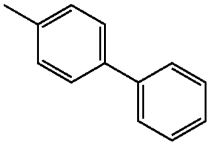 |
| 5 | 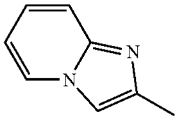 | 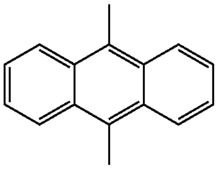 | 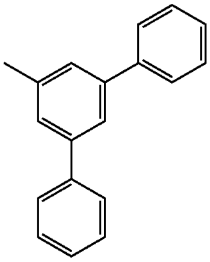 |
| 6 | 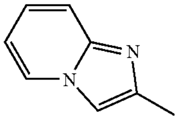 | 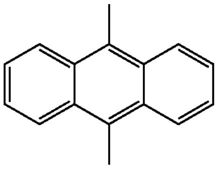 | 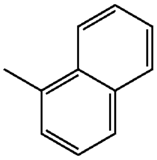 |
| 7 | 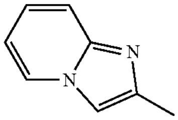 | 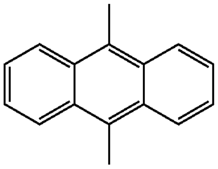 | 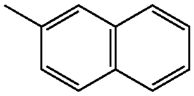 |
| 8 | 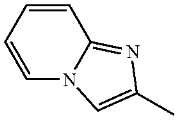 | 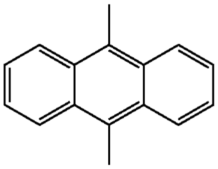 | 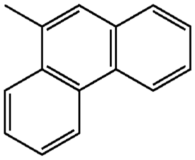 |
| 9 | 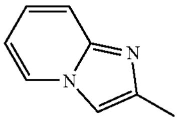 | 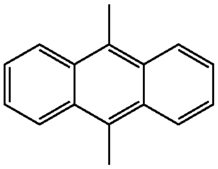 | 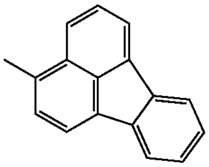 |

-continued
| | | | |
|---|---|---|---|
| 10 | 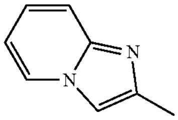 | 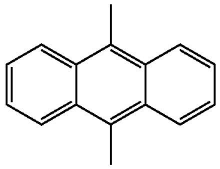 | 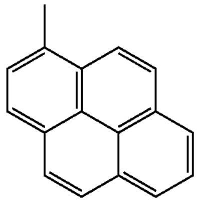 |
| 11 | 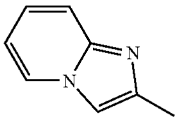 | 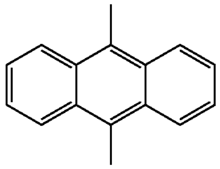 | 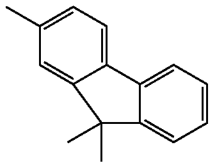 |
| 23-1 | 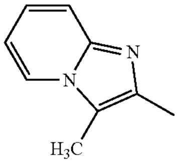 | 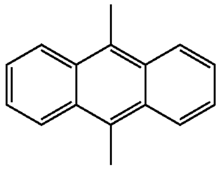 | 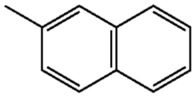 |
| 2 | 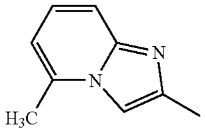 | 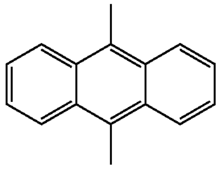 | 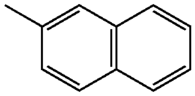 |
| 3 | 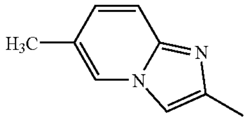 | 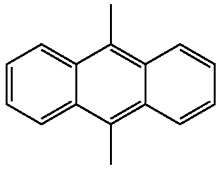 | 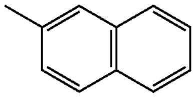 |
| 4 | 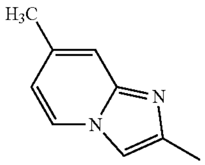 | 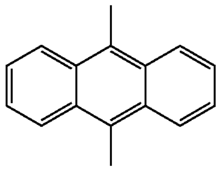 | 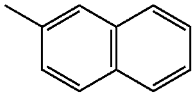 |
| 5 | 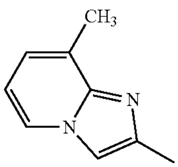 | 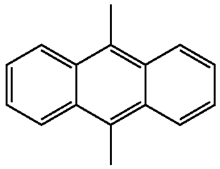 | 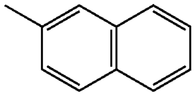 |
| 6 | 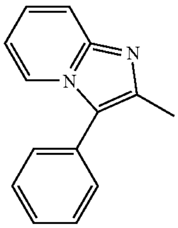 | 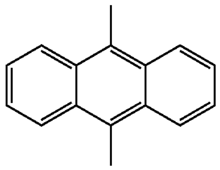 | 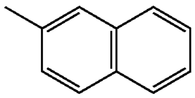 |

-continued
| | | | |
|---|---|---|---|
| 7 | 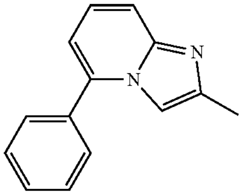 | 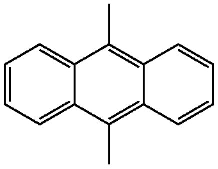 | 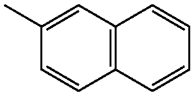 |
| 8 | 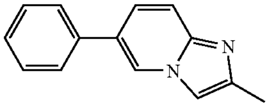 | 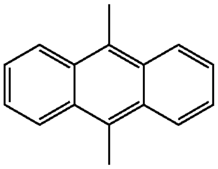 | 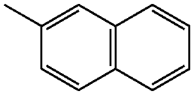 |
| 9 | 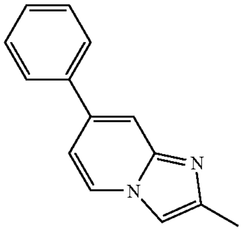 | 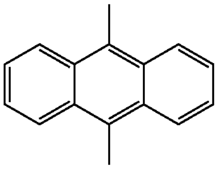 | 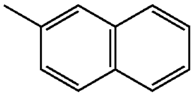 |
| 10 | 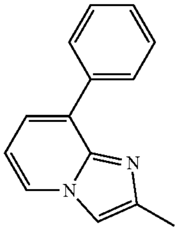 | 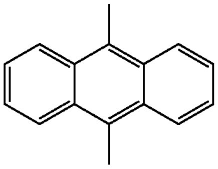 | 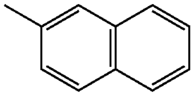 |
| 24-1 | 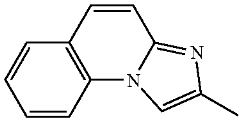 | 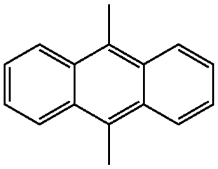 | 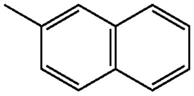 |
| 2 | 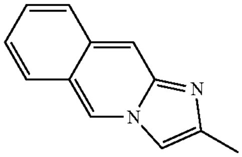 | 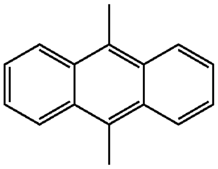 | 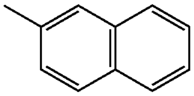 |
| 3 | 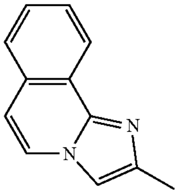 | 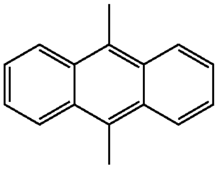 | 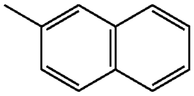 |
| 4 | 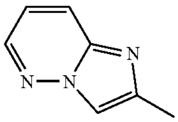 | 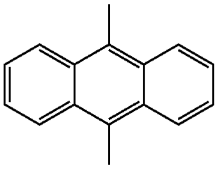 | 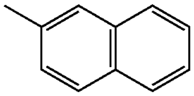 |

-continued
| | | | |
|---|---|---|---|
| 5 | 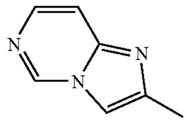 | 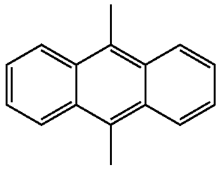 | 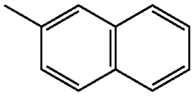 |
| 6 | 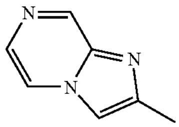 | 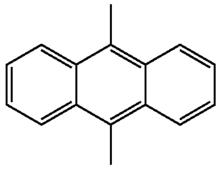 | 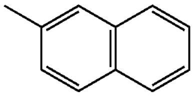 |
| 7 | 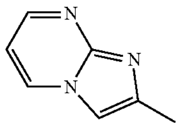 | 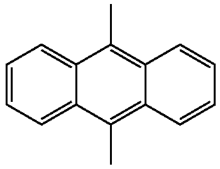 | 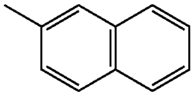 |
| 25-1 | 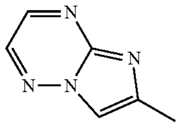 | 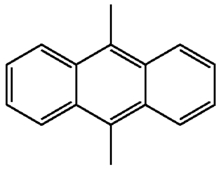 | 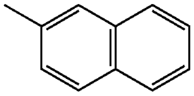 |
| 2 | 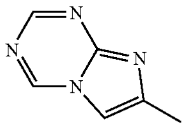 | 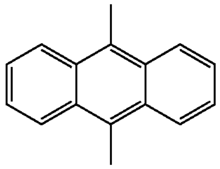 | 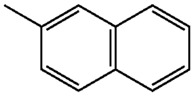 |
| 3 | 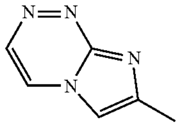 | 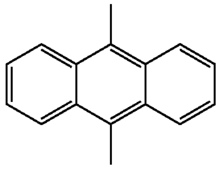 | 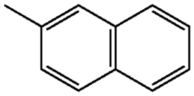 |
| 4 | 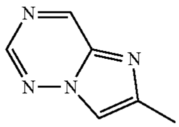 | 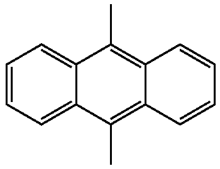 | 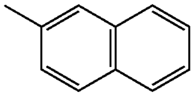 |
| 5 | 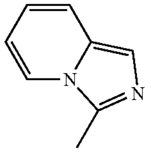 | 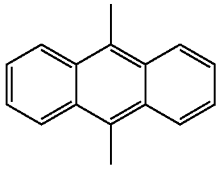 | 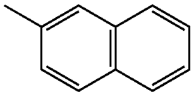 |

-continued
| | |
|---|---|
| 6 | 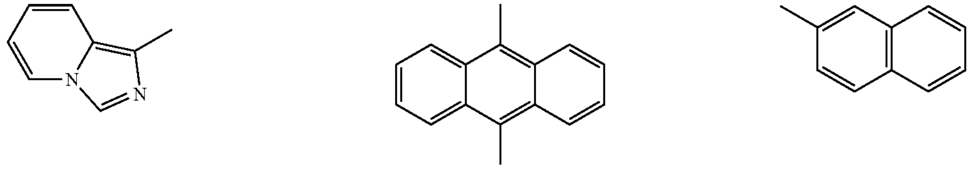 |
| 7 | 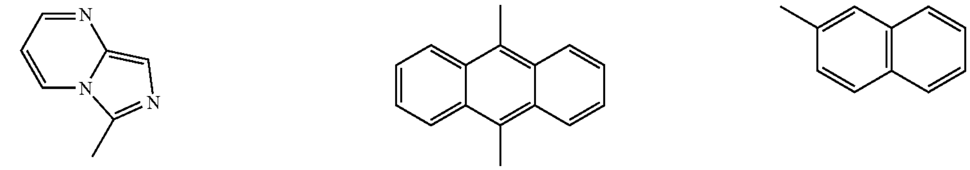 |
| 8 | 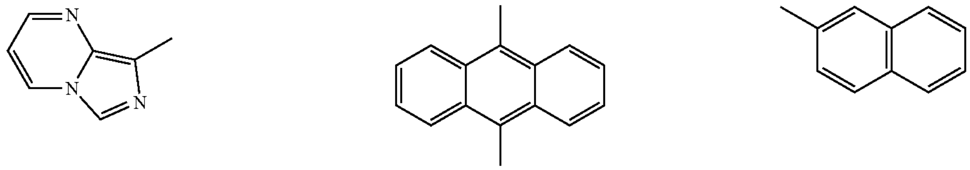 |
| 9 | 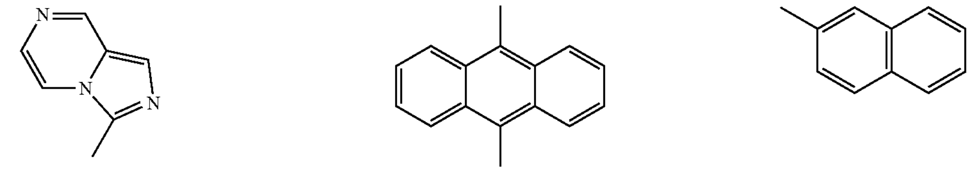 |
| 10 | 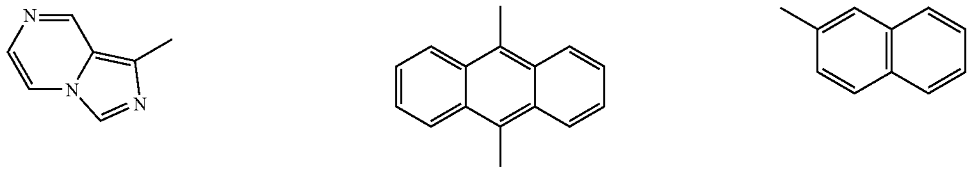 |
| 11 | 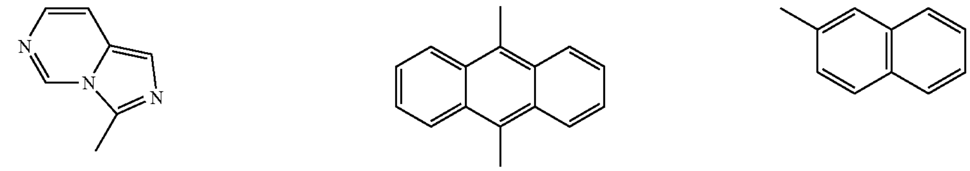 |
| 12 | 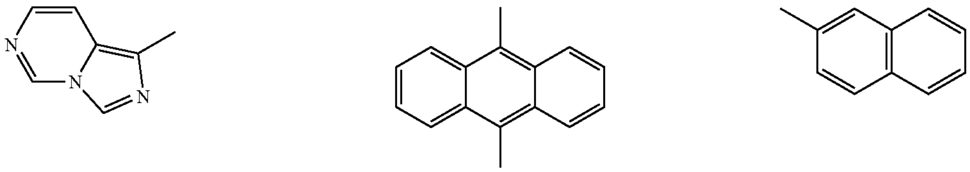 |
| 26-1 | 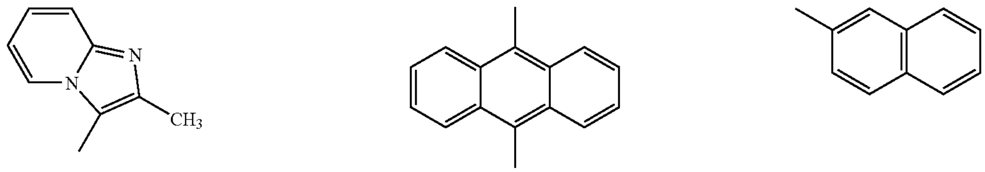 |
| 2 | 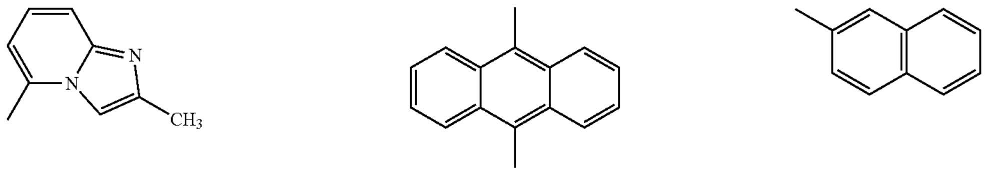 |

-continued
| | | | |
|---|---|---|---|
| 3 | 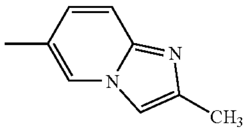 | 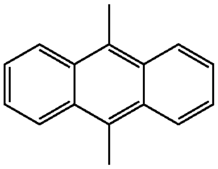 | 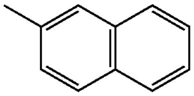 |
| 4 | 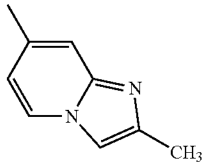 | 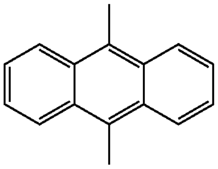 | 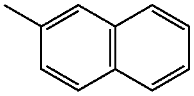 |
| 5 | 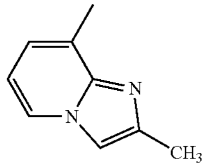 | 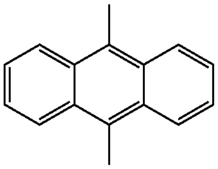 | 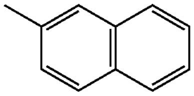 |
| 6 | 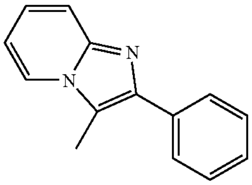 | 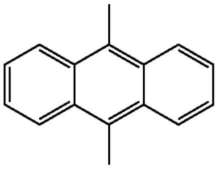 | 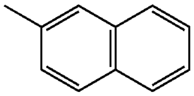 |
| 7 | 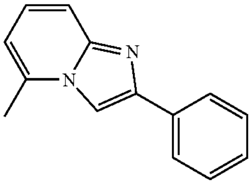 | 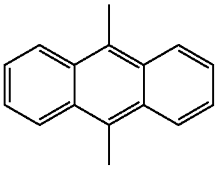 | 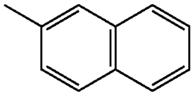 |
| 8 | 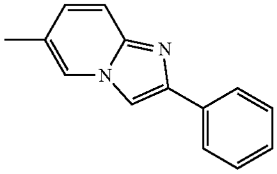 | 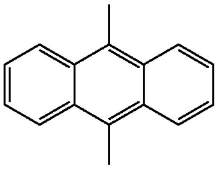 | 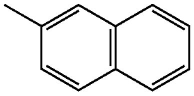 |
| 9 | 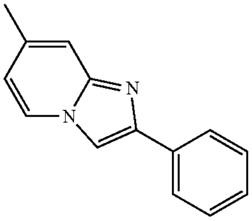 | 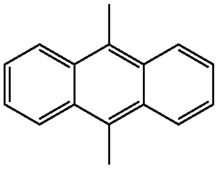 | 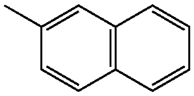 |
| 10 | 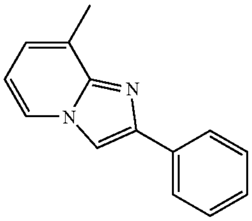 | 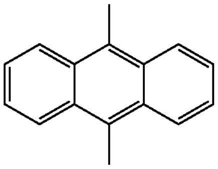 | 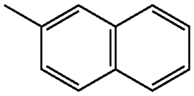 |

-continued
| | | | |
|---|---|---|---|
| 27-1 | 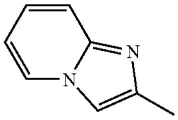 | 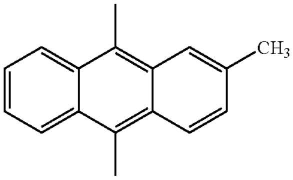 | 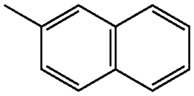 |
| 2 | 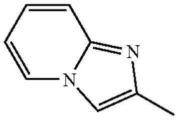 | 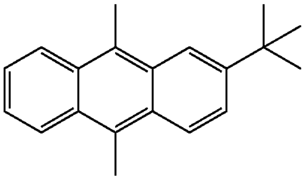 | 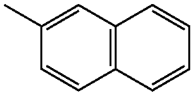 |
| 3 | 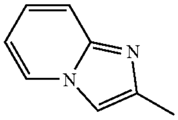 | 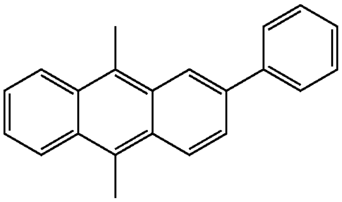 | 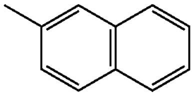 |
| 4 | 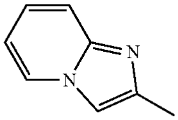 | 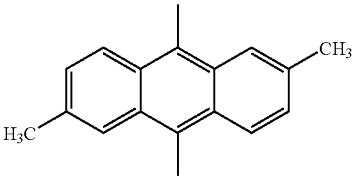 | 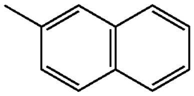 |
| 5 | 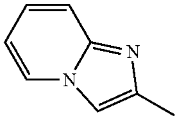 | 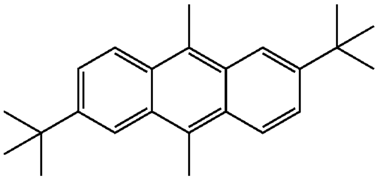 | 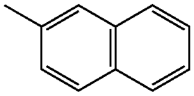 |
| 6 | 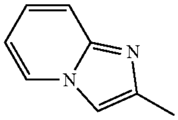 | 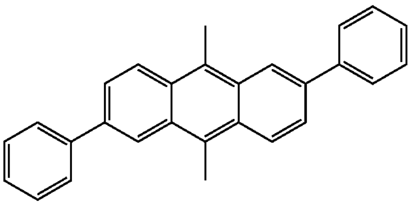 | 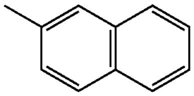 |
| 28-1 | 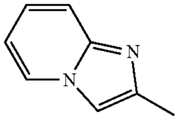 | 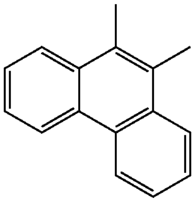 | 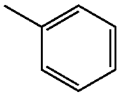 |
| 2 | 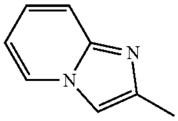 | 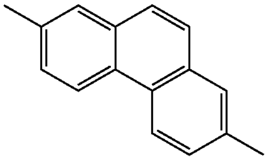 | 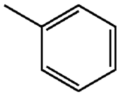 |

-continued

| | | | |
|---|---|---|---|
| 3 | 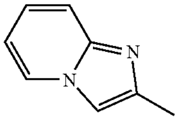 | 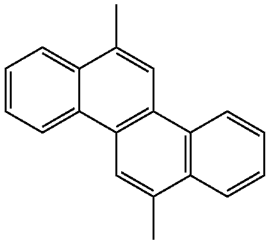 | 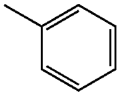 |
| 4 | 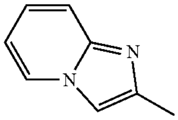 | 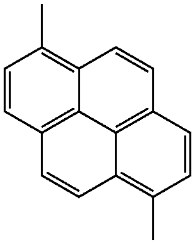 | 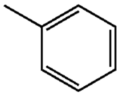 |
| 5 | 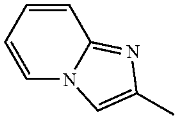 | 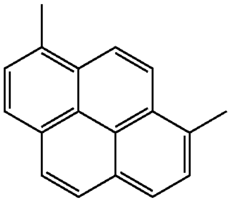 | 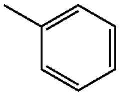 |
| 6 | 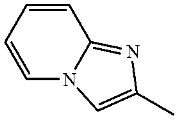 | 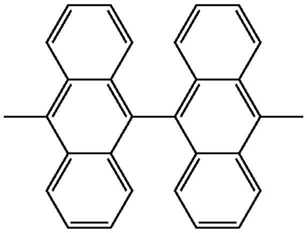 | 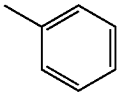 |
| 7 | 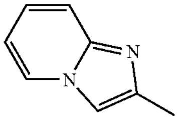 | 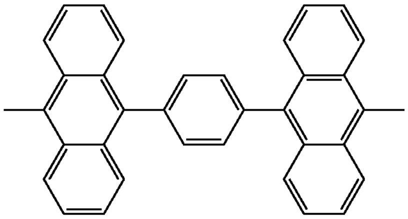 | 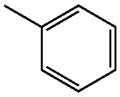 |

Among the above specific examples, Compounds (1-1), (1-3), (1-4), (1-10), (1-11), (2-3), (2-4), (3-3), (3-4), (3-10), (3-11), (4-3), (4-4), (5-11), (5-4), (5-18), (8-4), (9-11), (10-18), (13-11), (13-14), (13-15), (13-16), (14-1), (14-2), (14-6), (14-7), (14-9), (15-1), (15-3), (15-4), (15-5), (16-3), (19-1), (19-5) and (26-8) are particularly preferable.

Next, the derivatives of heterocyclic compound having nitrogen atom represented by general formulae (1') to (3') of the present invention will be explained below.

In general formula (1'), $A^1$ to $A^3$ each independently represents nitrogen atom or carbon atom.

In the above general formula (1'), $Ar^{1'}$ represents a substituted or unsubstituted aryl group having 6 to 60 nuclear carbon atoms (preferably having 6 to 40 nuclear carbon atoms) or a substituted or unsubstituted heteroaryl group having 3 to 60 nuclear carbon atoms (preferably having 3 to 40 nuclear carbon atoms).

Examples of the substituted or unsubstituted aryl group represented by $Ar^{1'}$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-chrysenyl group, 2-chrysenyl group, 6-chrysenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group, monovalent groups having the spirofluorene structure, perfluorophenyl group, perfluoronaphthyl group, perfluoroanthryl group, perfluorobiphenylyl group, monovalent groups having the 9-phenylanthancene structure, monovalent groups having the 9-(1'-naphthyl)anthracene structure, monovalent groups having the 9-(2'-naphthyl)anthracene structure, monovalent groups having the 6-phenylchrysene structure and monovalent groups having the 9-[4-(diphenylamino)phenyl]anthracene structure. Among these groups, phenyl group, naphthyl groups, biphenyl groups, terphenyl groups, 9-(10-phenyl)anthryl group, 9-[10-(1'-naphthyl)] anthryl group and 9-[10-(2'-naphthyl)] anthryl group are preferable.

Examples of the substituted or unsubstituted heteroaryl group represented by $Ar^{1'}$ include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group and triazolyl group. Among these groups, pyridyl group, quinolyl group and isoquinolyl group are preferable.

In general formula (1'), $Ar^{2'}$ represents hydrogen atom, a substituted or unsubstituted aryl group having 6 to 60 nuclear carbon atoms (preferably having 6 to 40 nuclear carbon atoms), a substituted or unsubstituted heteroaryl group having 3 to 60 nuclear carbon atoms (preferably having 3 to 40 nuclear carbon atoms), a substituted or unsubstituted alkyl group having 1 to 20 nuclear carbon atoms (preferably having 1 to 6 carbon atoms) or a substituted or unsubstituted alkoxyl group having 1 to 20 nuclear carbon atoms (preferably having 1 to 6 carbon atoms).

Examples of the substituted or unsubstituted aryl group represented by $Ar^{2'}$ include the groups described above as the examples of the substituted or unsubstituted aryl group represented by $Ar^{1'}$.

Examples of the substituted or unsubstituted heteroaryl group represented by $Ar^{2'}$ include the groups described above as the examples of the substituted or unsubstituted heteroaryl group represented by $Ar^{1'}$.

Examples of the substituted or unsubstituted alkyl group represented by $Ar^{2'}$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group. Among these groups, methyl group, ethyl group and t-butyl group are preferable.

In general formula (1'), the substituted or unsubstituted alkoxyl group represented by $Ar^{2'}$ is a group represented by —OY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group. Among these groups, methyl group, ethyl group and t-butyl group are preferable.

In general formula (1'), at least one of the groups represented by $Ar^{1'}$ and Ar2' is a substituted or unsubstituted condensed cyclic group having 10 to 60 nuclear carbon atoms or a substituted or unsubstituted condensed mono-heterocyclic group having 3 to 60 nuclear carbon atoms.

In general formula (1'), $L^1$ and $L^2$ each independently represent the single bond, a substituted or unsubstituted arylene group having 6 to 60 nuclear carbon atoms (preferably having 6 to 40 nuclear carbon atoms), a substituted or unsubstituted heteroarylene group having 3 to 60 nuclear carbon atoms (preferably having 3 to 40 nuclear carbon atoms) or a substituted or unsubstituted fluorenylene group.

Examples of the substituted or unsubstituted arylene group represented by $L^1$ or $L^2$ include divalent groups formed by removing hydrogen atom from the aryl groups described above as the examples of the substituted or unsubstituted aryl group represented by the above Ar1'.

Examples of the substituted or unsubstituted heteroarylene group represented by $L^1$ or $L^2$ include divalent groups formed by removing hydrogen atom from the heteroaryl groups described above as the examples of the substituted or unsubstituted heteroaryl group represented by the above $Ar^{1'}$.

In general formula (1'), it is preferable that $L^1$ and/or $L^2$ represent a group selected from the group consisting of

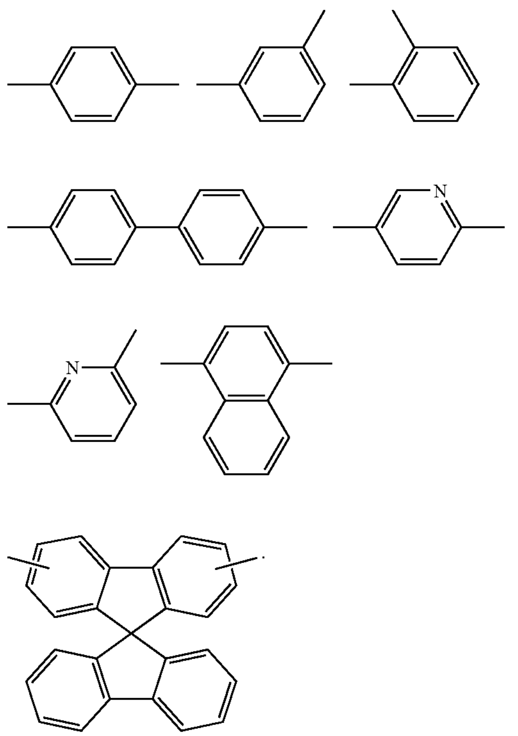

The above description is applied to the description below about general formulae (2') and (3').

It is preferable that, in general formula (1'), $Ar^{1'}$ represents a group represented by one of the following general formulae (4') to (13'). The above description is applied to the description below general formulae (2') and (3') below.

(4')

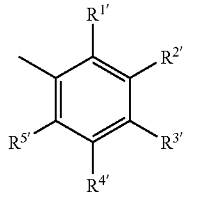

(5')

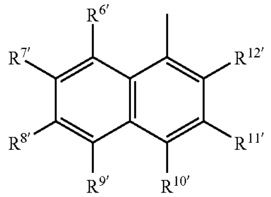

(6')

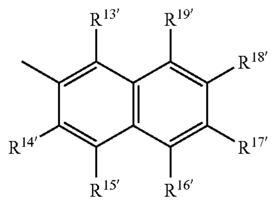

-continued (7')

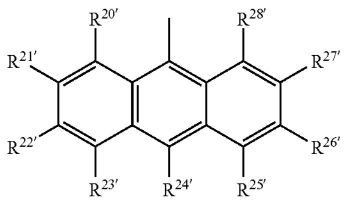

(8')

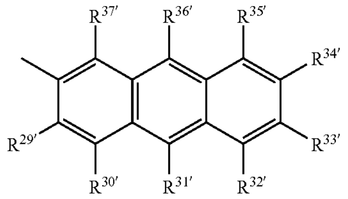

(9')

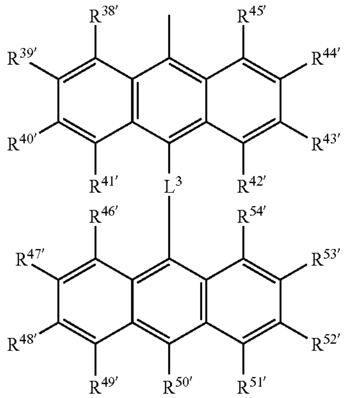

(10')

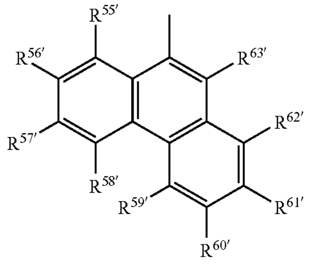

(11')

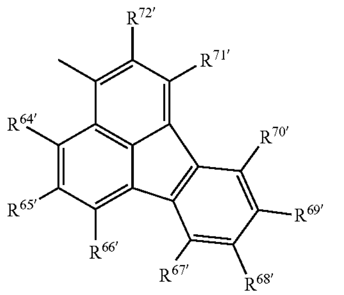

-continued (12')

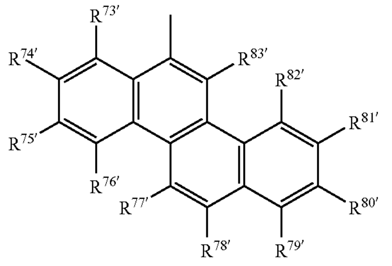

(13')

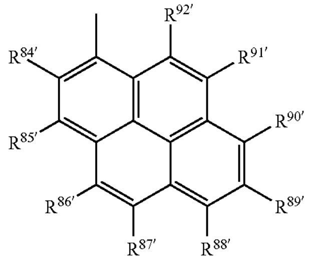

In the above formulae, $R^1$ to $R^{92'}$ each independently represent hydrogen atom, a halogen atom, a substituted or unsubstituted alkyl group having 1 to 20 carbon atoms, a substituted or unsubstituted alkoxyl 25 group having 1 to 20 carbon atoms, a substituted or unsubstituted aryloxyl group having 6 to 40 nuclear carbon atoms, a substituted or unsubstituted diarylamino group having 12 to 80 nuclear carbon atoms, a substituted or unsubstituted aryl group having 6 to 40 nuclear carbon atoms, a substituted or unsubstituted heteroaryl group having 3 to 40 nuclear carbon atoms or a substituted or unsubstituted diarylamino group having 18 to 120 nuclear carbon atoms, and $L^3$ represents the single bond or a group selected from the following groups:

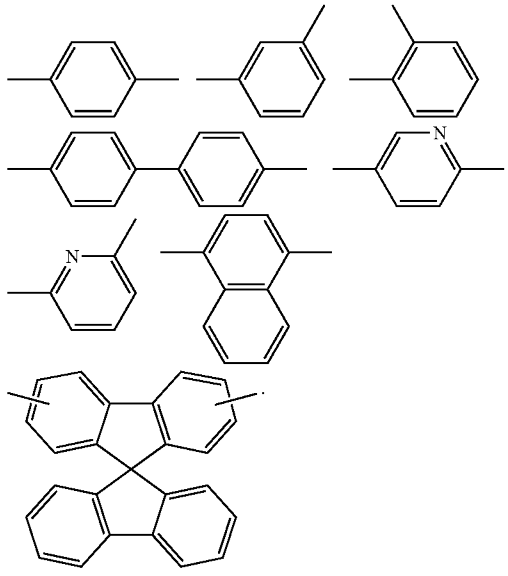

In general formula (1'), R represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms or a substituted or unsubstituted alkoxyl group having 1 to 20 carbon atoms.

Examples of the substituted or unsubstituted aryl group represented by R include the groups described above as the examples of the substituted or unsubstituted aryl group represented by the foregoing $Ar^{1'}$.

Examples of the substituted or unsubstituted heteroaryl group represented by R include the groups described above as the examples of the substituted or unsubstituted heteroaryl group represented by the foregoing $Ar^{1'}$.

Examples of the substituted or unsubstituted alkyl group represented by R include the groups described above as the examples of the substituted or unsubstituted alkyl group represented by the foregoing $Ar^{2'}$.

Examples of the substituted or unsubstituted alkoxyl group represented by R include the groups described above as the examples of the substituted or unsubstituted alkoxyl group represented by the foregoing $Ar^{2'}$.

In general formula (1'), n represents an integer of 0 to 5 and preferably 0 to 3. When n represents an integer of 2 or greater, the atoms or groups represented by a plurality of R may be the same with or different from each other, and the groups represented by the plurality of R which are adjacent to each other may be bonded to each other to form an alicyclic carbon ring or an aromatic carbon ring.

Examples of the alicyclic carbon ring include cyclic structures of cyclopentane and cyclohexane.

Examples of the aromatic carbon ring include aromatic structures of benzene, naphthalene, phenanthrene and anthracene.

In general formula (2'), $A^1$ to $A^3$ each independently represents the same as those described regarding with general formula (1').

In general formula (2'), $Ar^{1'}$ and $Ar^{2'}$ each independently represents the same as those described regarding with general formula (1'). At least one of the groups represented by $Ar^{1'}$ and $Ar^{2'}$ is a substituted or unsubstituted condensed cyclic group having 10 to 60 nuclear carbon atoms or a substituted or unsubstituted condensed mono-heterocyclic group having 3 to 60 nuclear carbon atoms.

In general formula (2'), $L^1$ and $L^2$ each independently represents the same as those described regarding with general formula (1').

In general formula (2'), R' is the same as R in general formula (1').

In general formula (3'), $A^1$ and $A^2$ each independently represents the same as those described regarding with general formula (1').

In general formula (3'), $Ar^{1'}$ and Ar2' each independently represents the same as those described regarding with general formula (1'). At least one of the groups represented by $Ar^{1'}$ and $Ar^{2'}$ is a substituted or unsubstituted condensed cyclic group having 10 to 60 nuclear carbon atoms or a substituted or unsubstituted condensed mono-heterocyclic group having 3 to 60 nuclear carbon atoms.

In general formula (3'), $L^1$ and $L^2$ each independently represents the same as those described regarding with general formula (1').

In general formula (3'), R' and R" each independently represents the same as R in general formula (1'). R' and R" may be the same or different from each other.

Specific examples of the derivative of heterocyclic compound having nitrogen atom represented by general formulae (1') to (3') of the present invention are as follows, however, the present invention is not limited to these typical compounds:

In the following tables, "\"represents single bond.
| | | | | |
|---|---|---|---|---|
| | 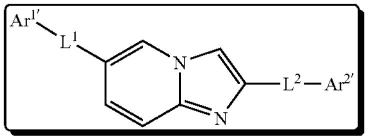 (Basic Backbone Structure) | | | |
| | $Ar^{1'}$ | $L^1$ | $L^2$ | $Ar^{2'}$ |
| 1-1' | 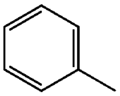 | 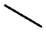 | 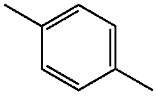 | 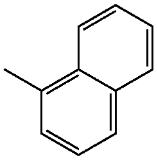 |
| 2' | 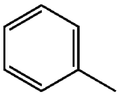 | 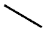 | 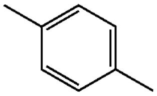 | 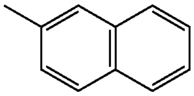 |
| 3' | 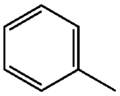 | 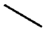 | 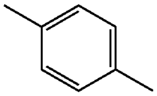 | 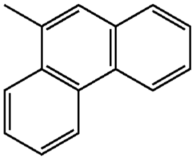 |
| 4' | 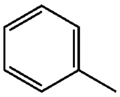 | 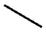 | 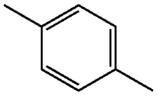 | 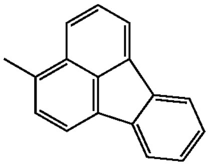 |
| 5' | 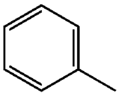 | 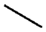 | 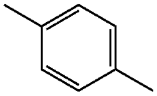 | 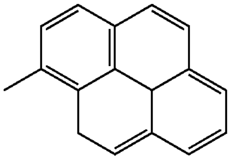 |
| 6' | 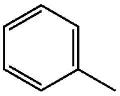 | 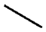 | 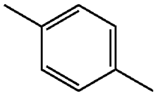 | 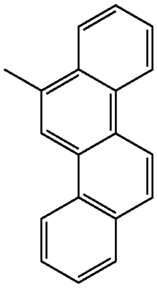 |

-continued
| | | | | |
|---|---|---|---|---|
| 7' | 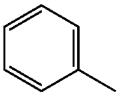 | 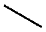 | 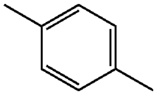 | 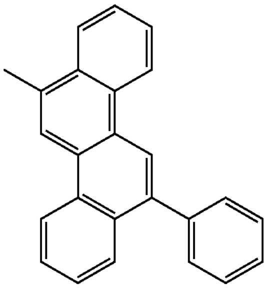 |
| 8' | 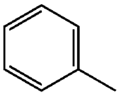 | 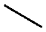 | 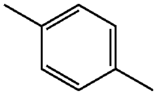 | 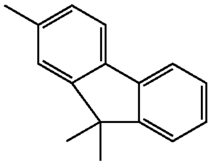 |
| 2-1' | 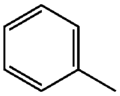 | 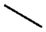 | 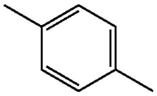 | 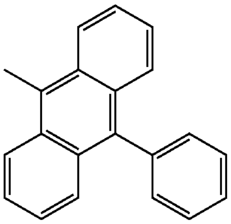 |
| 2' | 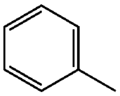 | 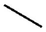 | 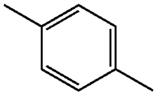 | 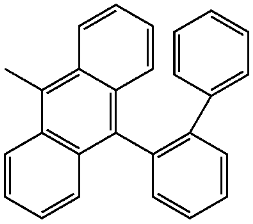 |
| 3' | 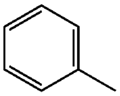 | 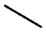 | 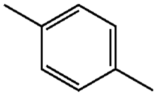 | 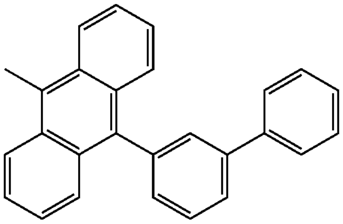 |
| 4' | 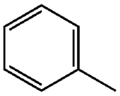 | 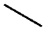 | 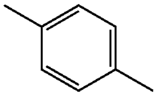 | 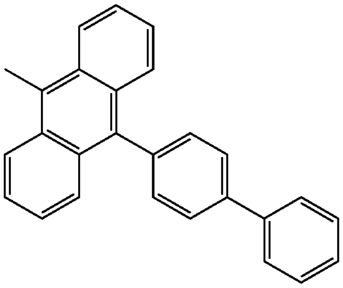 |

-continued
| | | | | |
|---|---|---|---|---|
| 5' | 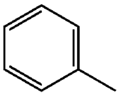 | 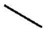 | 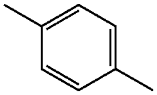 | 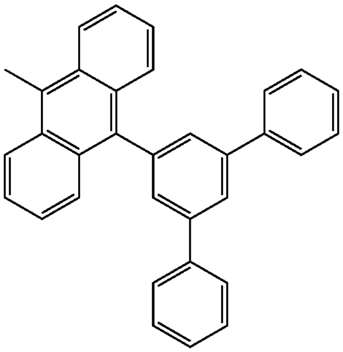 |
| 6' | 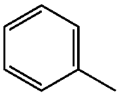 | 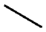 | 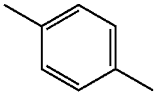 | 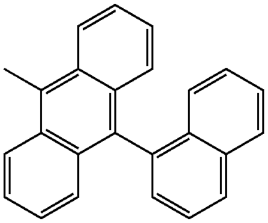 |
| 7' | 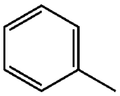 | 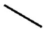 | 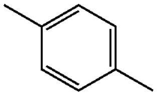 | 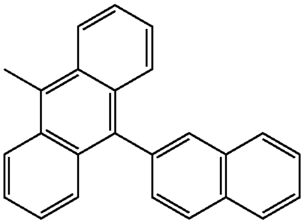 |
| 8' | 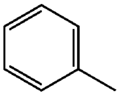 | 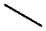 | 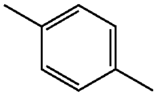 | 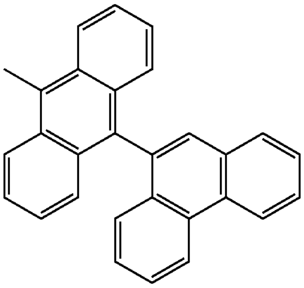 |
| 9' | 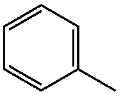 | 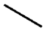 | 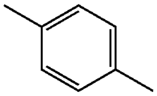 | 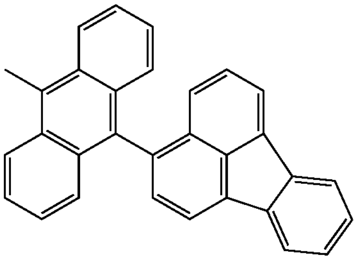 |
| 10' | 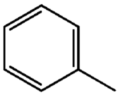 | 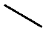 | 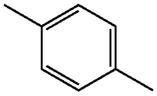 | 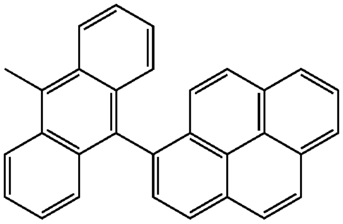 |

-continued
11'
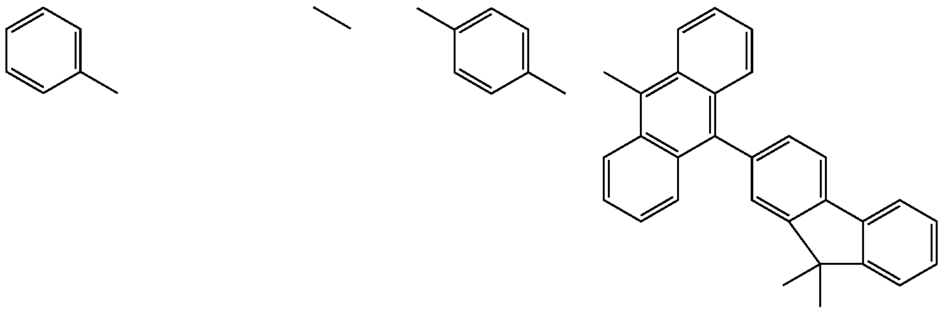
12'
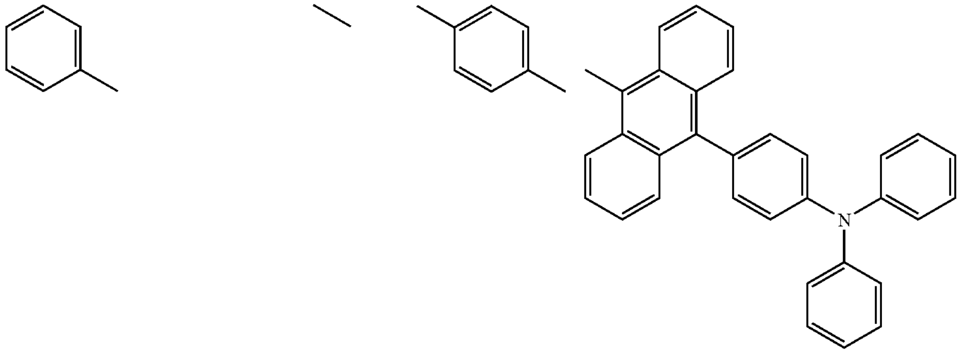
3-1'
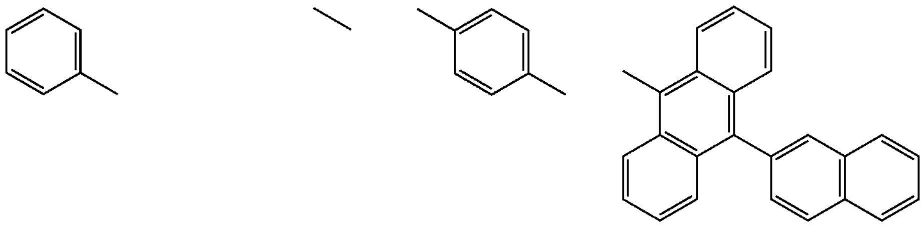
2'
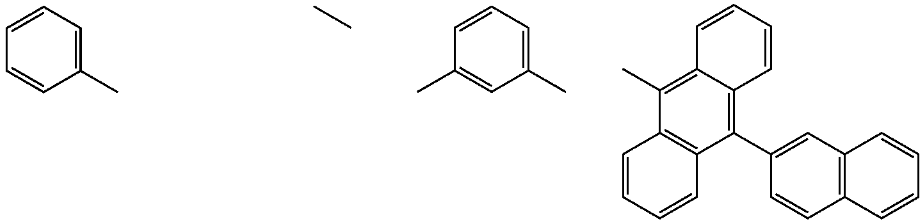
3'
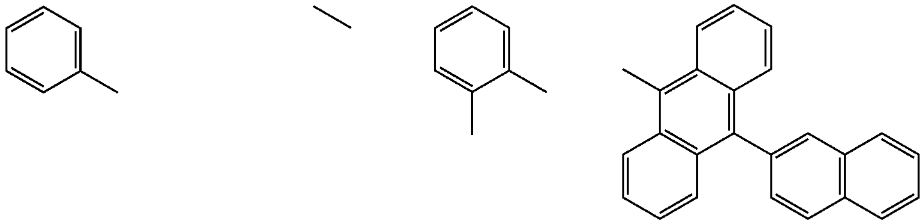

-continued
| | | | | |
|---|---|---|---|---|
| 4' | 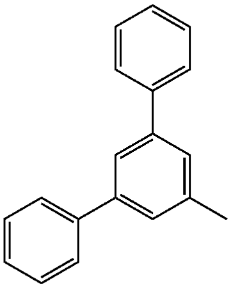 | 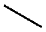 | 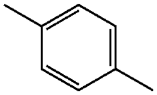 | 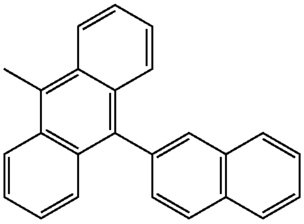 |
| 5' | 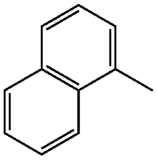 | 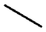 | 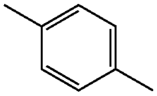 | 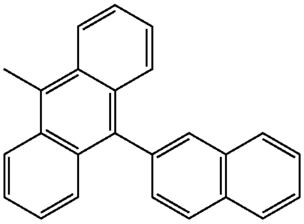 |
| 6' | 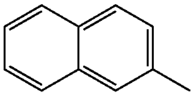 | 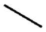 | 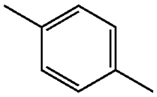 | 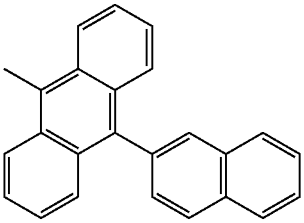 |
| 7' | 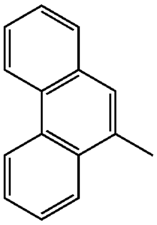 | 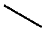 | 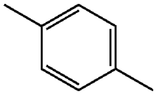 | 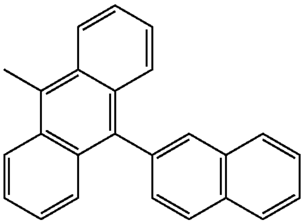 |
| 8' | 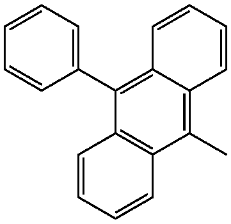 | 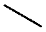 | 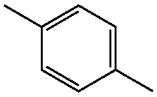 | 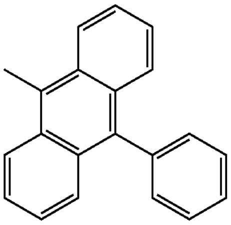 |
| 9' | 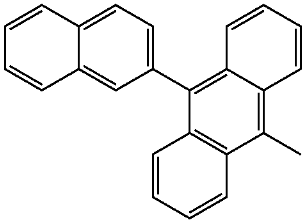 | 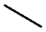 | 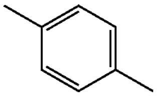 | 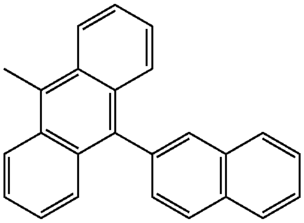 |
| 10' | 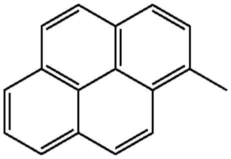 | 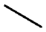 | 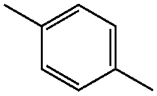 | 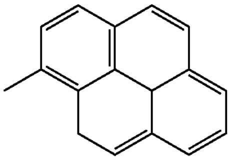 |

-continued
| | | | | |
|---|---|---|---|---|
| 4-1' | 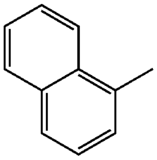 | 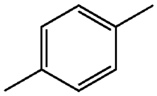 | 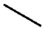 | 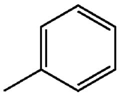 |
| 2' | 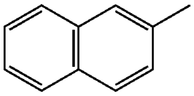 | 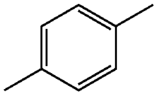 | 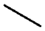 | 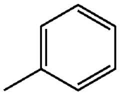 |
| 3' | 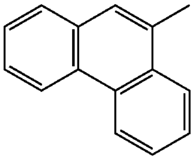 | 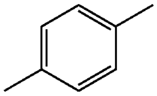 | 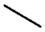 | 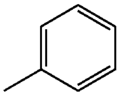 |
| 4' | 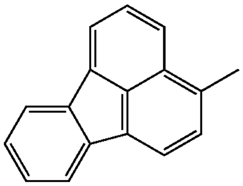 | 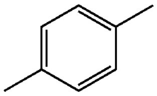 | 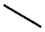 | 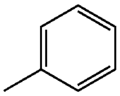 |
| 5' | 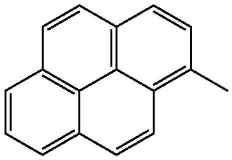 | 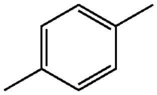 | 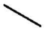 | 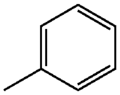 |
| 6' | 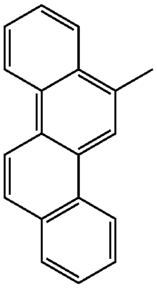 | 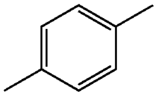 | 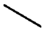 | 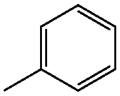 |
| 7' | 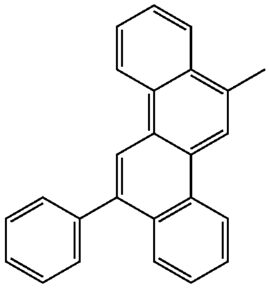 | 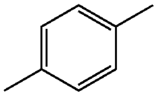 | 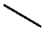 | 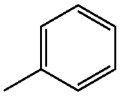 |
| 8' | 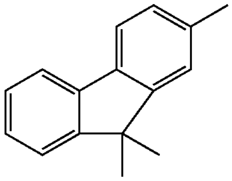 | 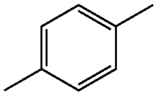 | 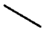 | 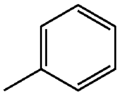 |

-continued
| | | | | |
|---|---|---|---|---|
| 5-1' | 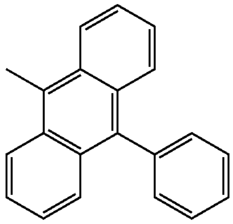 | 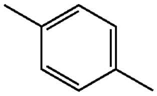 | 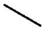 | 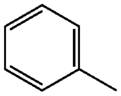 |
| 2' | 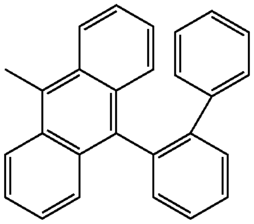 | 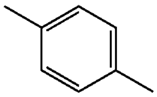 | 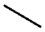 | 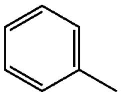 |
| 3' | 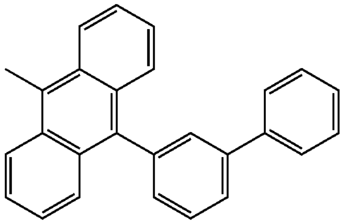 | 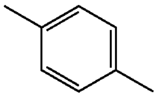 | 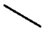 | 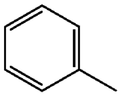 |
| 4' | 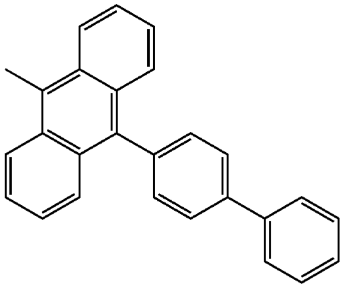 | 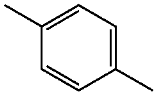 | 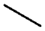 | 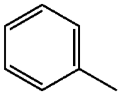 |
| 5' | 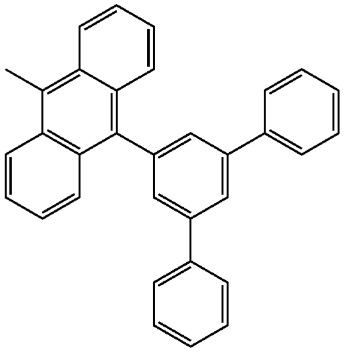 | 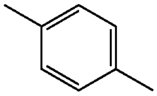 | 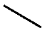 | 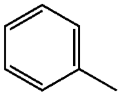 |
| 6' | 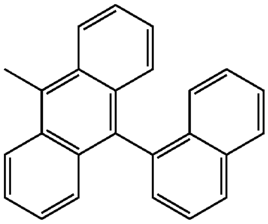 | 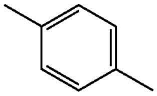 | 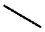 | 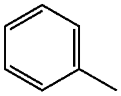 |

-continued
| | | | | |
|---|---|---|---|---|
| 7' | 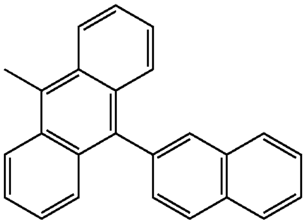 | 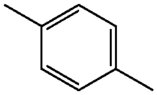 | 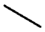 | 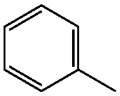 |
| 8' | 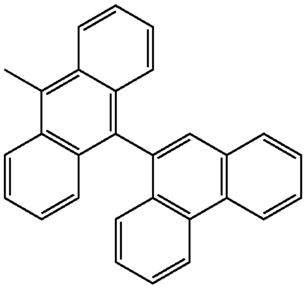 | 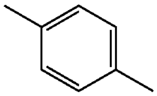 | 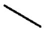 | 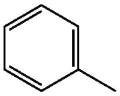 |
| 9' | 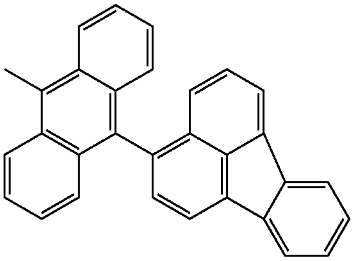 | 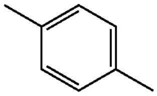 | 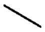 | 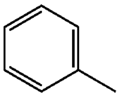 |
| 10' | 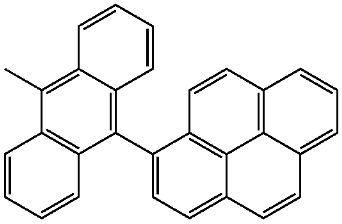 | 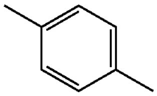 | 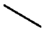 | 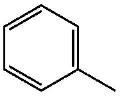 |
| 11' | 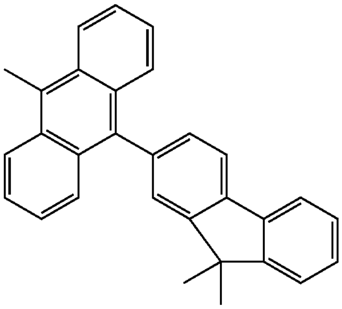 | 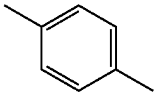 | 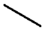 | 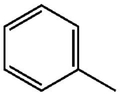 |

-continued
| | | | | |
|---|---|---|---|---|
| 12' | 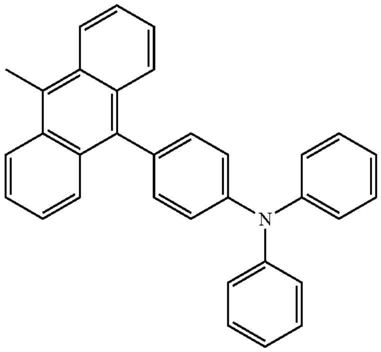 | 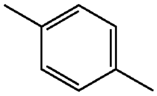 | 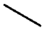 | 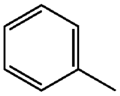 |
| 6-1' | 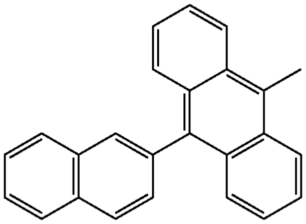 | 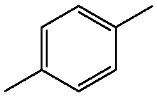 | 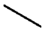 | 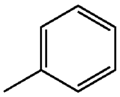 |
| 2' | 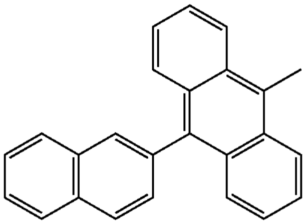 | 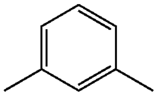 | 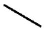 | 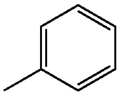 |
| 3' | 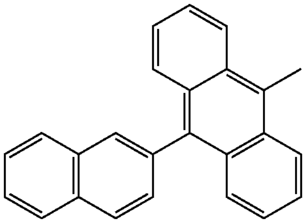 | 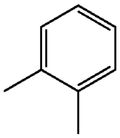 | 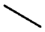 | 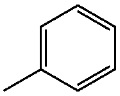 |
| 4' | 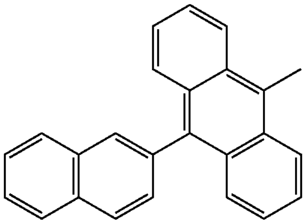 | 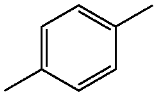 | 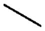 | 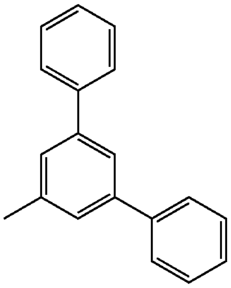 |
| 5' | 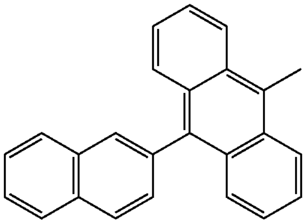 | 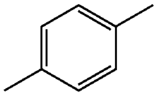 | 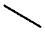 | 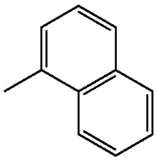 |

-continued
| | | | | |
|---|---|---|---|---|
| 6' | 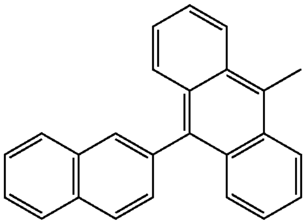 | 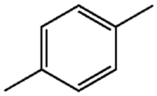 | 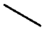 | 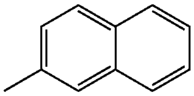 |
| 7' | 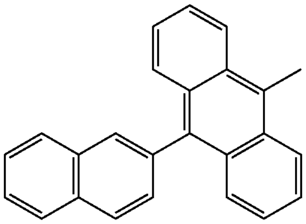 | 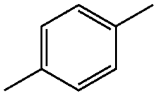 | 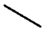 | 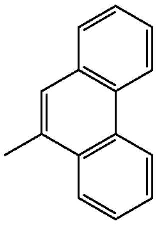 |
| 8' | 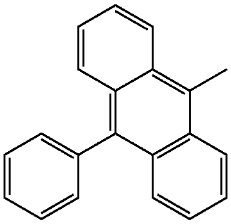 | 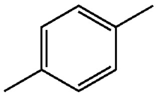 | 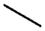 | 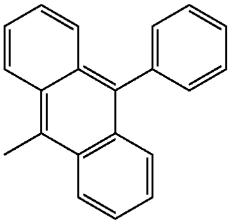 |
| 9' | 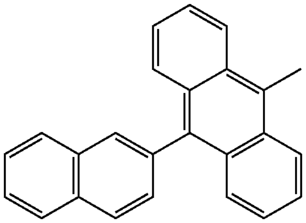 | 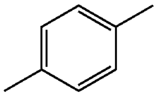 | 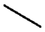 | 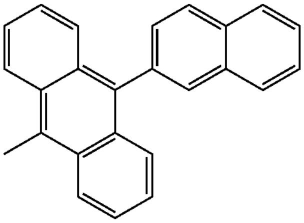 |
| 10' | 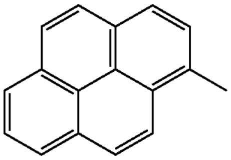 | 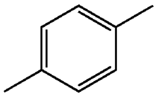 | 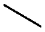 | 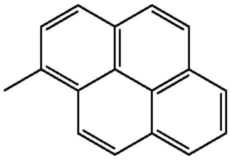 |
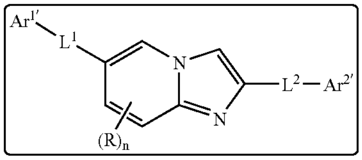
(Basic Backbone Structure)
| | $Ar^{1'}$ | $L^1$ | | $L^2$ | $Ar^{2'}$ |
|---|---|---|---|---|---|
| 7-1' | 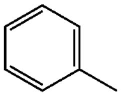 | 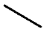 | 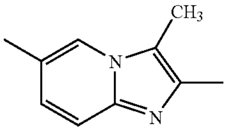 | 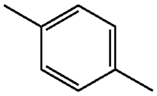 | 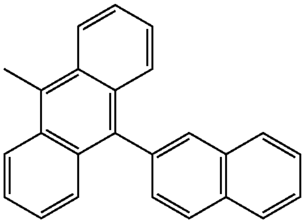 |

-continued
2' 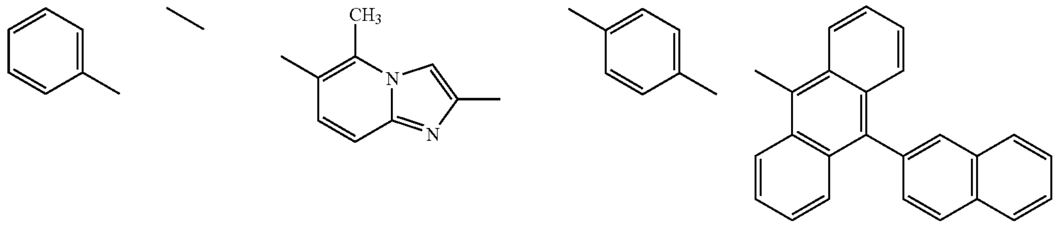
3' 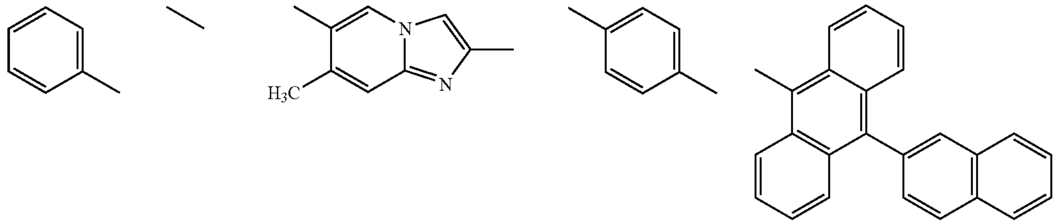
4' 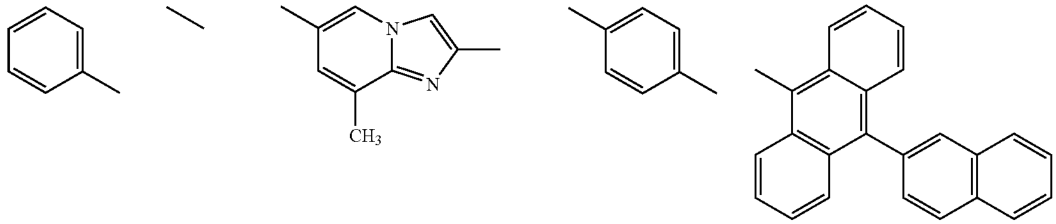
5' 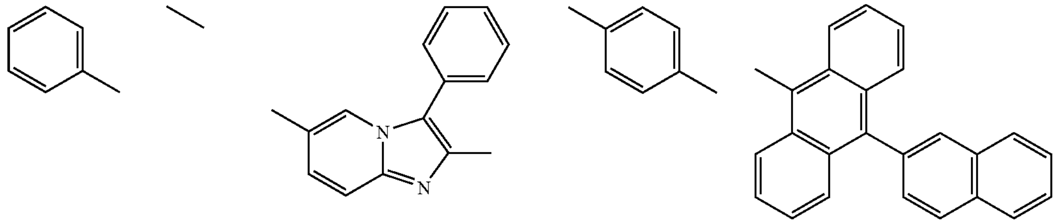
6' 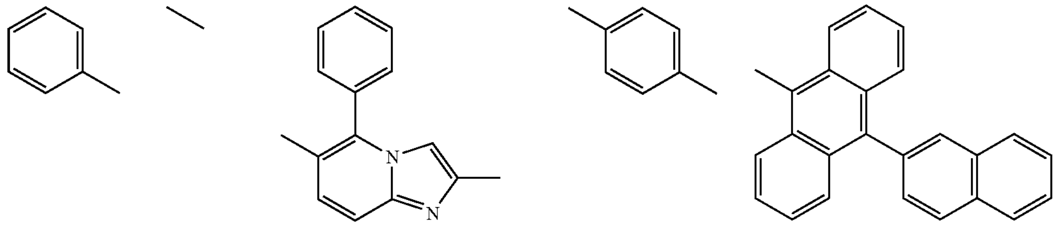
7' 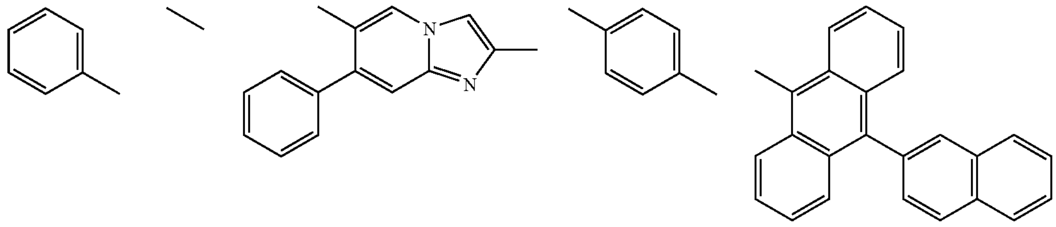

-continued
| | | | | | |
|---|---|---|---|---|---|
| 8' | 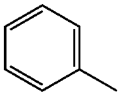 | 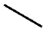 | 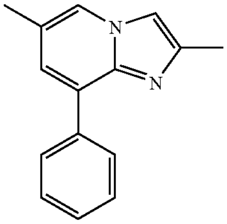 | 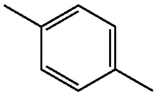 | 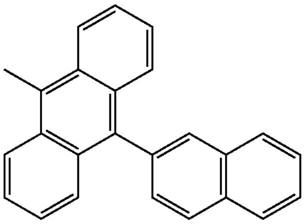 |
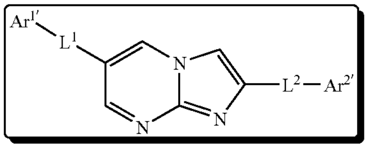
(Basic Backbone Structure)
| | Ar$^{1'}$ | L$^1$ | L$^2$ | Ar$^2$ |
|---|---|---|---|---|
| 8-1' | 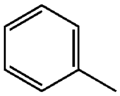 | 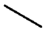 | 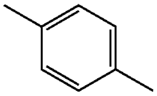 | 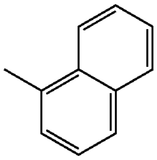 |
| 2' | 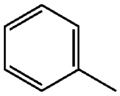 | 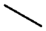 | 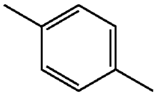 | 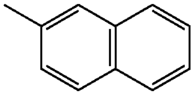 |
| 3' | 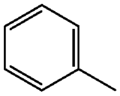 | 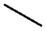 | 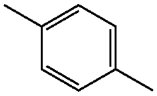 | 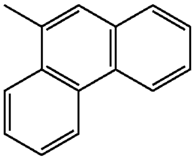 |
| 4' | 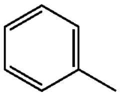 | 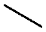 | 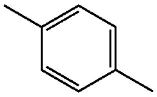 | 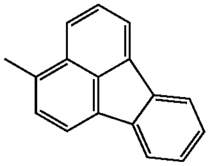 |
| 5' | 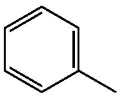 | 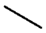 | 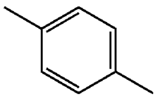 | 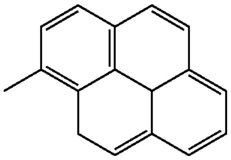 |
| 6' | 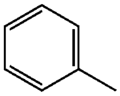 | 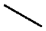 | 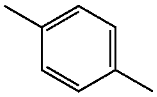 | 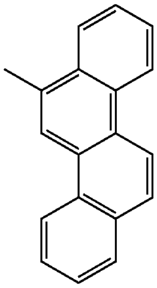 |

-continued
| | | | | |
|---|---|---|---|---|
| 7' | 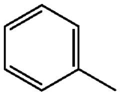 | 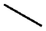 | 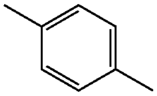 | 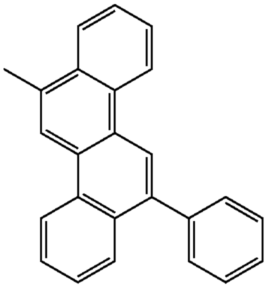 |
| 8' | 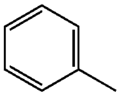 | 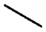 | 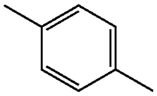 | 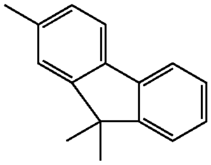 |
| 9-1' | 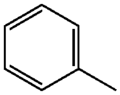 | 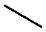 | 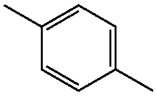 | 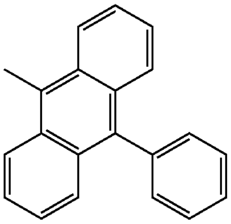 |
| 2' | 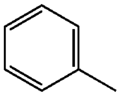 | 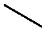 | 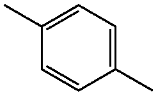 | 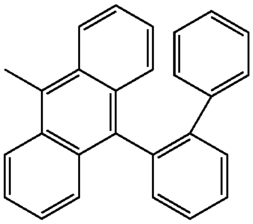 |
| 3' | 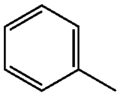 | 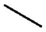 | 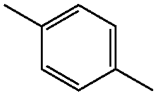 | 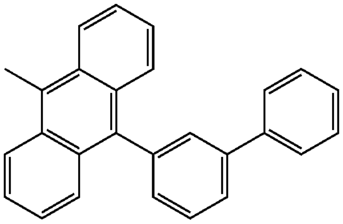 |
| 4' | 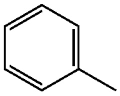 | 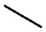 | 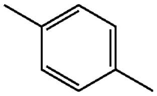 | 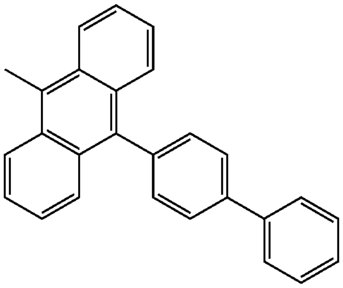 |

-continued
| | | | | |
|---|---|---|---|---|
| 5' | 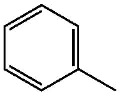 | 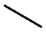 | 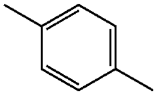 | 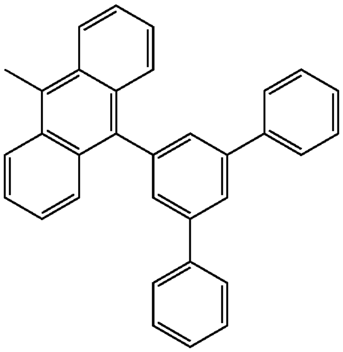 |
| 6' | 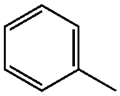 | 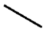 | 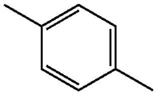 | 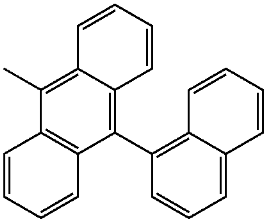 |
| 7' | 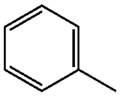 | 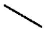 | 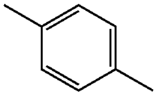 | 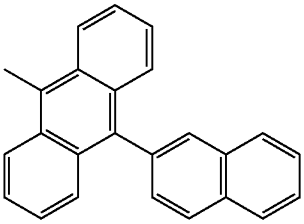 |
| 8' | 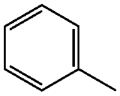 | 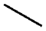 | 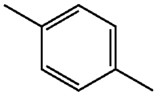 | 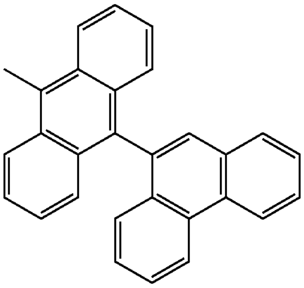 |
| 9' | 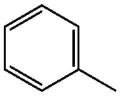 | 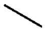 | 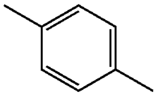 | 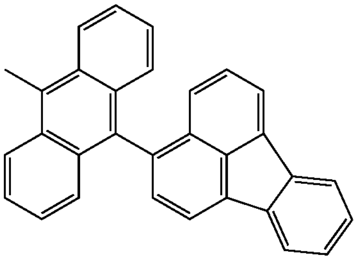 |
| 10' | 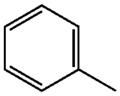 | 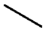 | 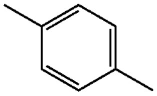 | 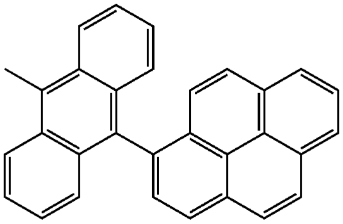 |

-continued
| | | | | |
|---|---|---|---|---|
| 11' | 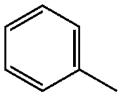 | 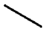 | 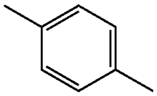 | 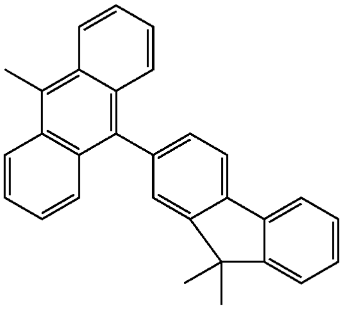 |
| 12' | 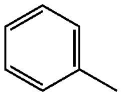 | 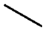 | 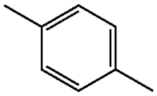 | 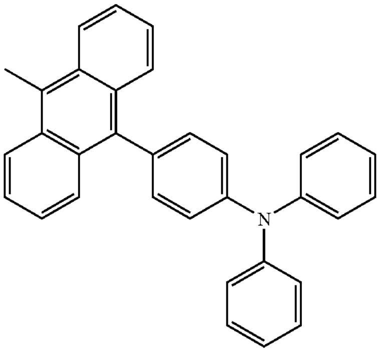 |
| 10-1' | 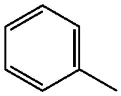 | 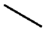 | 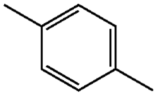 | 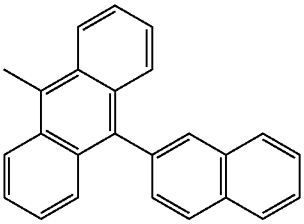 |
| 2' | 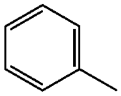 | 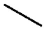 | 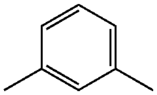 | 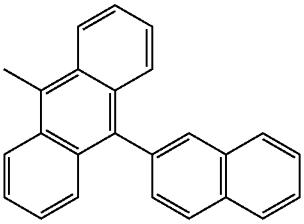 |
| 3' | 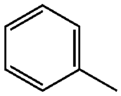 | 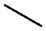 | 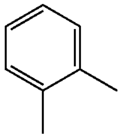 | 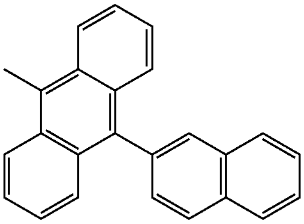 |

-continued
| | | | | |
|---|---|---|---|---|
| 4' | 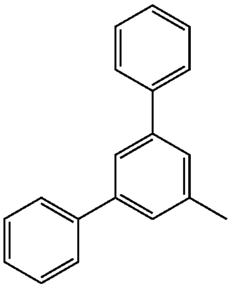 | 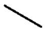 | 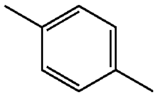 | 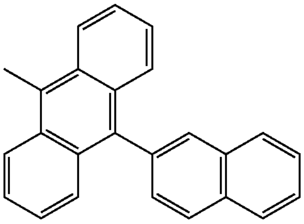 |
| 5' | 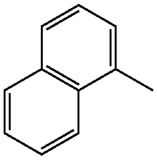 | 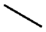 | 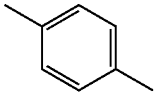 | 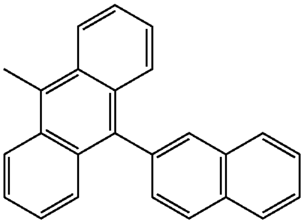 |
| 6' | 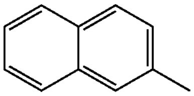 | 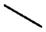 | 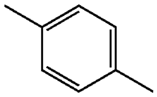 | 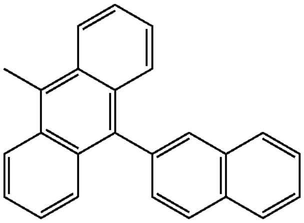 |
| 7' | 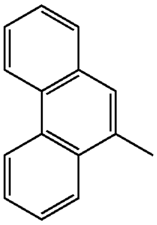 | 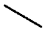 | 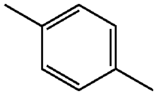 | 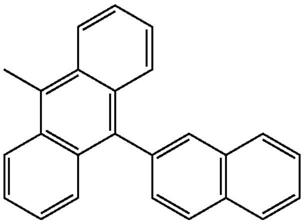 |
| 8' | 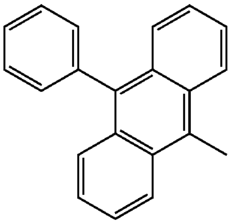 | 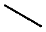 | 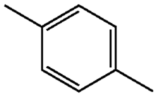 | 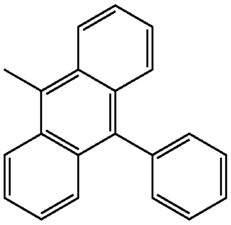 |
| 9' | 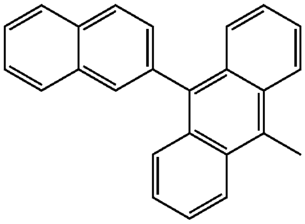 | 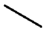 | 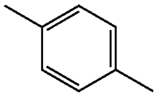 | 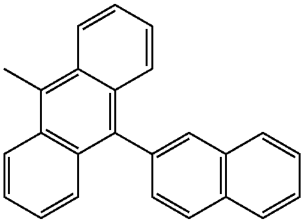 |
| 10' | 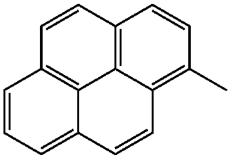 | 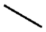 | 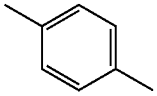 | 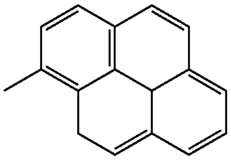 |

-continued
| | | | | |
|---|---|---|---|---|
| 11-1' | 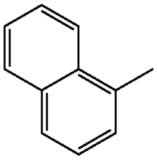 | 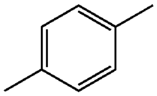 | 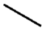 | 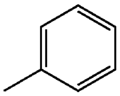 |
| 2' | 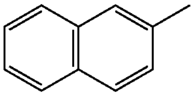 | 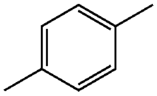 | 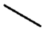 | 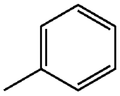 |
| 3' | 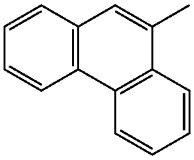 | 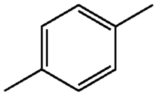 | 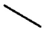 | 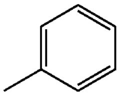 |
| 4' | 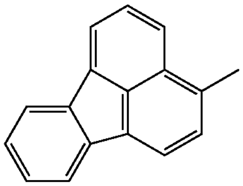 | 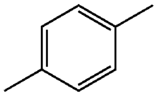 | 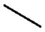 | 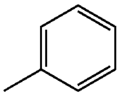 |
| 5' | 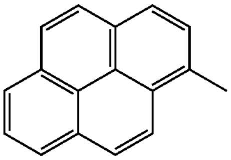 | 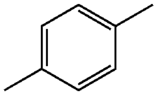 | 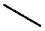 | 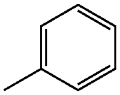 |
| 6' | 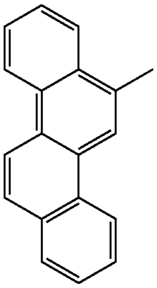 | 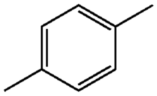 | 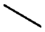 | 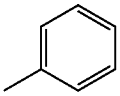 |
| 7' | 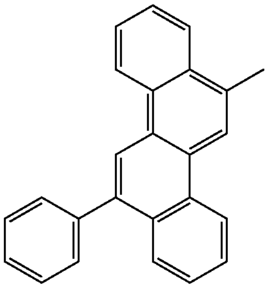 | 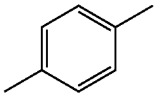 | 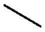 | 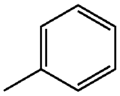 |
| 8' | 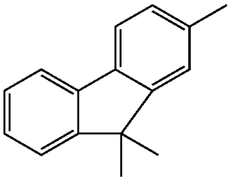 | 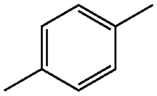 | 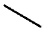 | 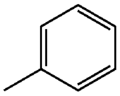 |

-continued
| | | | | |
|---|---|---|---|---|
| 12-1' | 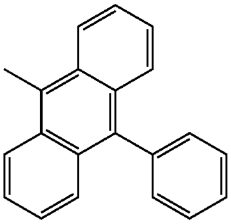 | 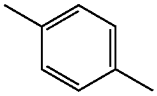 | 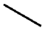 | 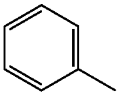 |
| 2' | 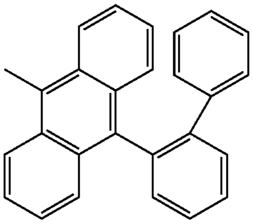 | 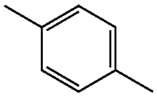 | 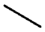 | 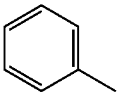 |
| 3' | 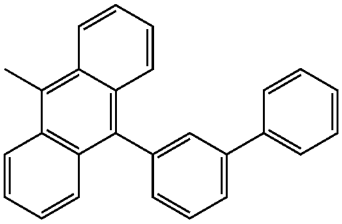 | 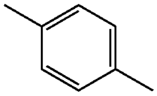 | 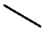 | 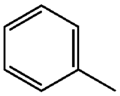 |
| 4' | 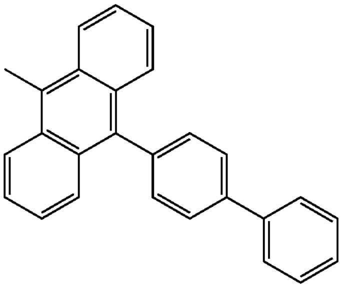 | 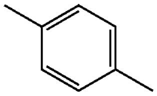 | 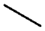 | 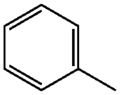 |
| 5' | 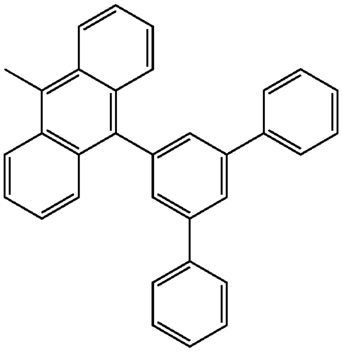 | 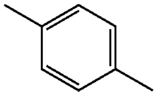 | 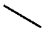 | 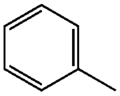 |
| 6' | 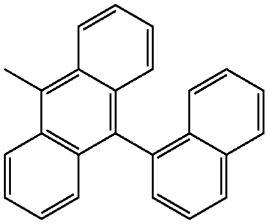 | 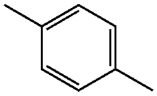 | 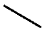 | 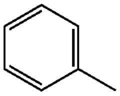 |

-continued
| | | | | |
|---|---|---|---|---|
| 7' | 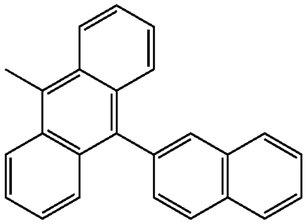 | 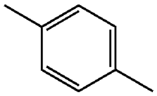 | 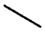 | 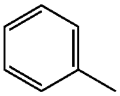 |
| 8' | 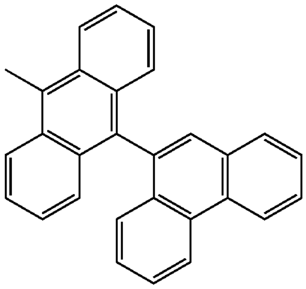 | 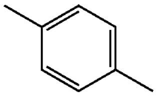 | 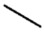 | 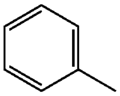 |
| 9' | 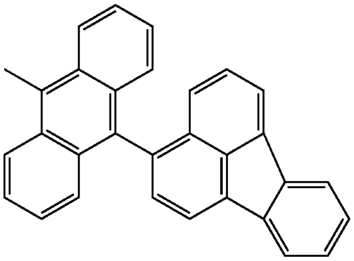 | 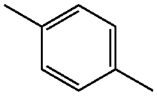 | 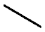 | 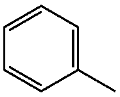 |
| 10' | 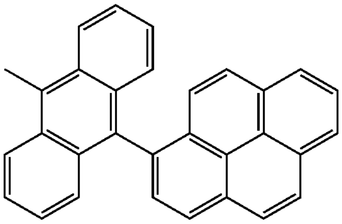 | 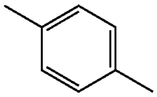 | 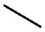 | 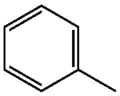 |
| 11' | 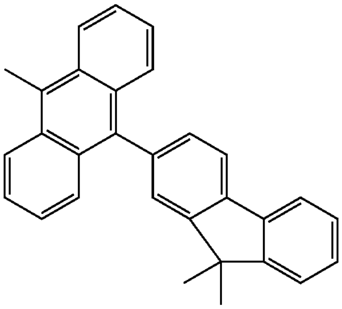 | 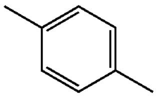 | 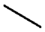 | 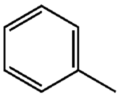 |

-continued
| | | | | |
|---|---|---|---|---|
| 12' | 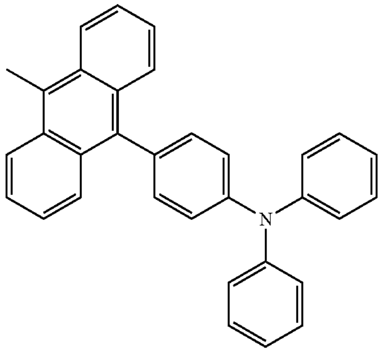 | 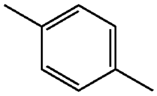 | 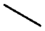 | 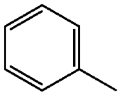 |
| 13-1' | 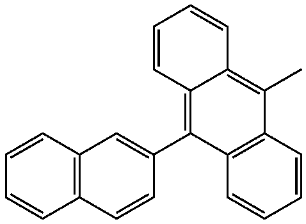 | 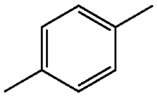 | 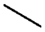 | 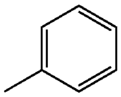 |
| 2' | 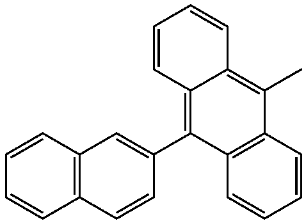 | 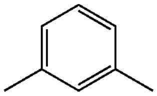 | 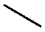 | 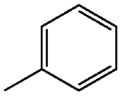 |
| 3' | 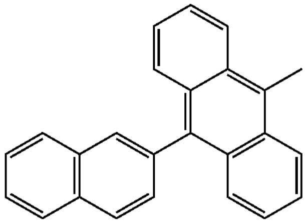 | 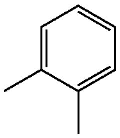 | 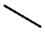 | 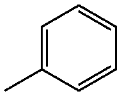 |
| 4' | 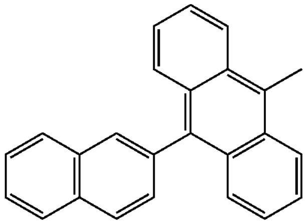 | 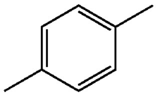 | 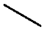 | 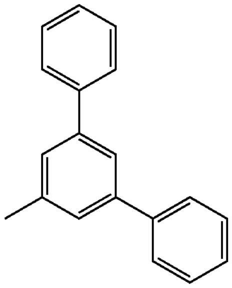 |
| 5' | 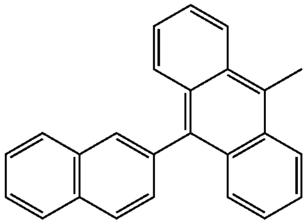 | 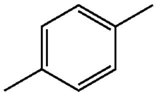 | 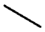 | 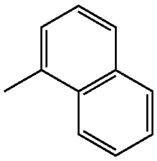 |

-continued
| | | | | |
|---|---|---|---|---|
| 6' | 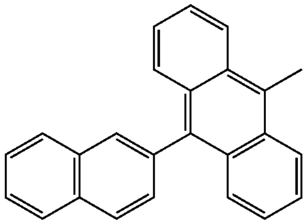 | 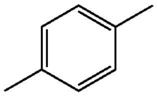 | 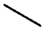 | 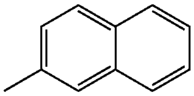 |
| 7' | 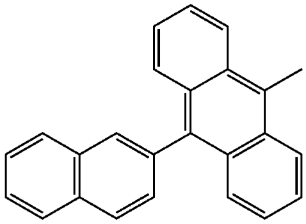 | 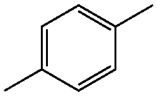 | 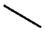 | 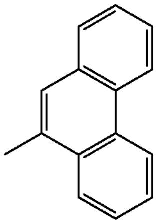 |
| 8' | 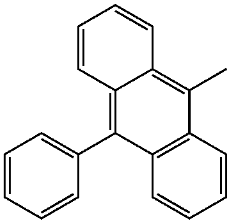 | 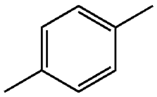 | 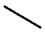 | 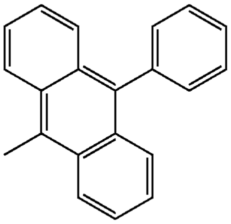 |
| 9' | 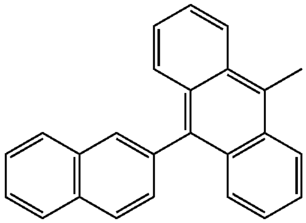 | 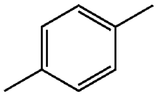 | 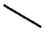 | 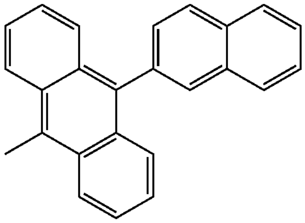 |
| 10' | 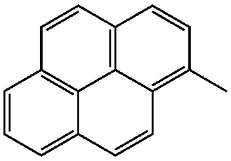 | 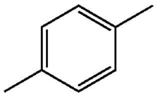 | 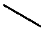 | 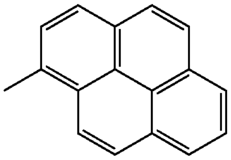 |
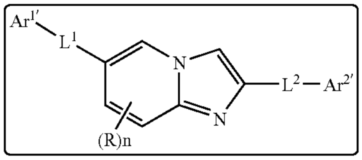
(Basic Backbone Structure)
| | $Ar^1$ | $L^1$ | | $L^2$ | $Ar^2$ |
|---|---|---|---|---|---|
| 14-1' | 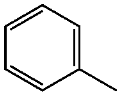 |  | 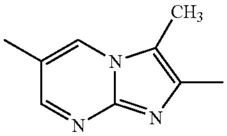 | 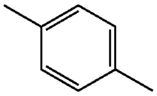 | 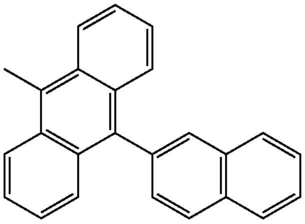 |

-continued

2'

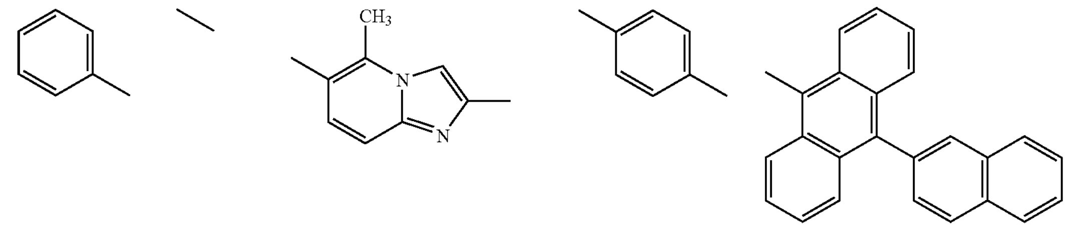

3'

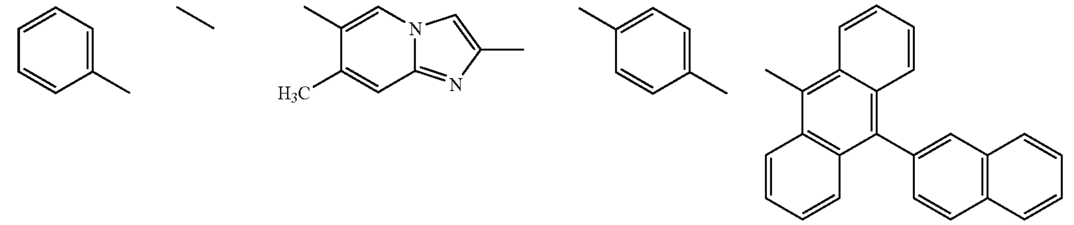

4'

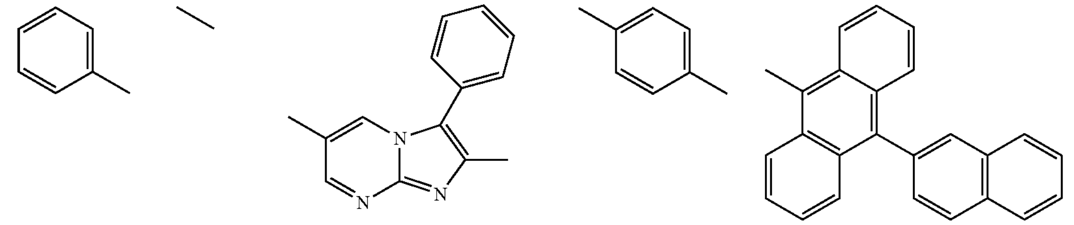

5'

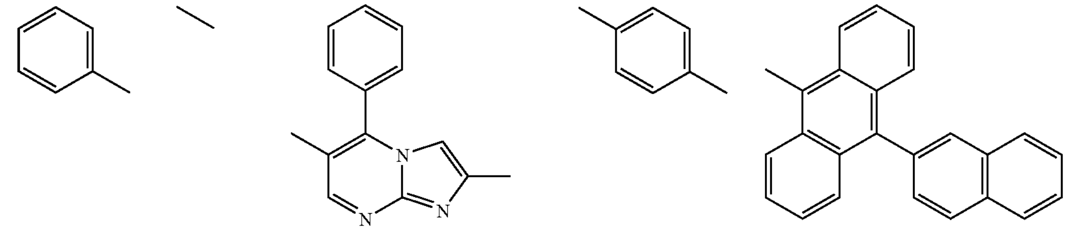

6'

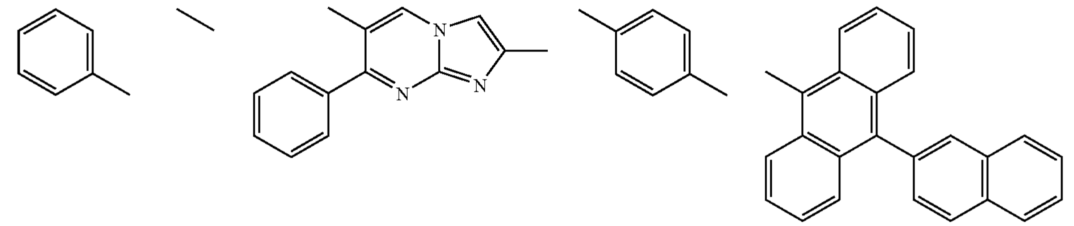

The derivative of heterocyclic compound having nitrogen atom represented by general formulae (1) and (1') to (3') of the present invention have excellent electron injecting capability or electron transporting capability and preferably employed as a material for the organic EL devices.

Employing the compound of the present invention as at least one layer among the organic compound layers of the organic EL devices enables to achieve elevation of luminance and current efficiency and also to achieve long term stability by improvement of an electrode adhesion resultantly making the EL device of long lifetime.

It is preferable that the compound of the present invention is employed to a light emitting zone, a light emitting layer and/or an electron transporting layer of the organic EL device. In particular, it is preferable that the compound of the present invention is employed as an electron injecting material and/or an electron transporting material. Further, it is preferable that a layer containing the electron injecting material and/or the electron transporting material comprises reductive dopant.

The light emitting zone means the whole area containing a luminescent material which emits light when an electric field is applied to the organic EL device. Currently, the organic EL device has, in general, a laminated structure of each thin film comprising materials having different function and role, and in many cases, only an organic thin film layer named as a light emitting layer comprises the luminescent material. In this case, the light emitting layer corresponds to the light emitting zone. Further, explanations about the light emitting layer, the electron transporting layer and the electron injecting material will be described below.

Following is a description regarding a device structure about the organic EL device of the present invention.

The organic EL device of the present invention comprises at least one of organic compound layers containing a light emitting layer sandwiched between a pair of electrodes, wherein the organic compound layers comprises at least one layer containing a derivative of heterocyclic compound having nitrogen atom represented by any one of general formulae (1) and (1') to (3') of the present invention.

Typical examples of the construction of the organic EL device of the present invention include:

(1) An anode/a light emitting layer/a cathode;

(2) An anode/a hole injecting layer/a light emitting layer/a cathode;

(3) An anode/a light emitting layer/an electron injecting layer/a cathode;

(4) An anode/a hole injecting layer/a light emitting layer/an electron injecting layer/a cathode;

(5) An anode/an organic semiconductor layer/a light emitting layer/a cathode;

(6) An anode/an organic semiconductor layer/an electron barrier layer/a light emitting layer/a cathode;

(7) An anode/an organic semiconductor layer/a light emitting layer/an adhesion improving layer/a cathode;

(8) An anode/a hole injecting layer/a hole transporting layer/a light emitting layer/an electron injecting layer/a cathode;

(9) An anode/an insulating layer/a light emitting layer/an insulating layer/a cathode;

(10) An anode/an inorganic semiconductor layer/an insulating layer/a light emitting layer/an insulating layer/a cathode;

(11) An anode/an organic semiconductor layer/an insulating layer/a light emitting layer/an insulating layer/a cathode;

(12) An anode/an insulating layer/a hole injecting layer/a hole transporting layer/a light emitting layer/an insulating layer/a cathode; and

(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to those shown above as the examples.

It is preferable for the organic EL device of the present invention to employ the compound of the present invention as a constituting material for the light emitting layer and/or the electron injecting layer. Although the hole injecting layer or the electron injecting layer is not always necessary for the device structure, an organic EL device having these layers has an advantage of improving light emitting property. Further, the hole injecting layer, the light emitting layer and the electron injecting layer may be mixedly sandwiched between a pair of electrodes. Furthermore, a mixed layer may be made with the use of a binder such as a high molecular compound in order that each constituting component exists stably.

An explanation about an organic EL device of anode/hole injecting layer/light emitting layer/electron injecting layer/cathode type example of the present invention will be described hereinunder. In general, the organic EL device is produced on a substrate which transmits light. The substrate which transmits light is the substrate which supports the organic EL device. As the substrate which transmits light, for example, glass sheet, synthetic resin sheet and quortzes are advantageously employed. It is preferable that the substrate which transmits light has a transmittance of light of 50% or greater in the visible region of 400 to 700 nm. It is also preferable that a flat and smooth substrate is employed.

As the anode, an electrode made of a material such as a metal, an alloy, a conductive compound and a mixture of these materials which has a great work function (4 eV or more) is preferable. Specific examples of the material for the anode include metals such as Au and conductive materials such as CuI, ITO (indium tin oxide), $SnO_2$, ZnO and In—Zn—O. The anode can be prepared by forming a thin film of the electrode material described above in accordance with a process such as the vapor deposition process and the sputtering process. When the light emitted from the light emitting layer is obtained through the anode, it is preferable that the anode has a transmittance of the emitted light greater than 10%. It is also preferable that the sheet resistivity of the anode is several hundred Ω/□ or smaller. The thickness of the anode is, in general, selected in the range of from 10 nm to 1 m and preferably in the range of from 10 to 200 nm although the preferable range may be different depending on the adopted material.

As the cathode, an electrode made of a material such as a metal, an alloy, a conductive compound and a mixture of these materials which has a small work function (4 eV or smaller) is employed. Specific examples of the material for the cathode include sodium, sodium-potassium alloys, magnesium, magnesium-silver alloys, lithium, magnesium/copper mixture, magnesium-indium alloys, $Al/Al_2O_3$, indium, aluminum-lithium alloys, etc. The cathode can be prepared by forming a thin film of the electrode material described above in accordance with a process such as the vapor deposition process and the sputtering process. It is also preferable that the sheet resistivity of the cathode is several hundred Ω/□ or smaller. The thickness of the cathode is, in general, selected in the range of from 10 nm to 500 nm and preferably in the range of from 50 to 200 nm. Additionally, it is convenient that either the anode or the cathode of the organic EL device is transparent or translucent in order to transmit light because an efficiency of light emission improves.

In the organic EL device of the present invention, it is preferable that a layer of a chalcogenide, a metal halide or a metal oxide (this layer may occasionally be referred to as a surface layer) is disposed on the surface of at least one of the pair of electrodes prepared as described above. Specifically, it is preferable that a layer of a chalcogenide (including an oxide) of a metal such as silicon and aluminum is disposed on the surface of the anode at the side of the light emitting layer, and a layer of a metal halide or a metal oxide is disposed on the surface of the cathode at the side of the light emitting layer. Due to the above layers, stability in driving can be improved.

Preferable examples of the chalcogenide include SiOx ($1 \leqq x \leqq 2$), AlOx ($1 \leqq x \leqq 1.5$), SiON and SiAlON. Preferable examples of the metal halide include LiF, $MgF_2$, $CaF_2$ and fluorides of rare earth metals. Preferable examples of the metal oxide include $Cs_2O$, $Li_2O$, MgO, SrO, BaO and CaO.

In the organic EL device of the present invention, it is preferable that a mixed region of an electron transfer compound and a reductive dopant or a mixed region of a hole transfer compound and an oxidizing dopant is disposed on the surface of at least one of the pair of electrodes prepared as described above. Due to the mixed region disposed as described above, the electron transfer compound is reduced to form an anion, and injection and transportation of electrons from the mixed region into the light emitting medium can be facilitated. The hole transfer compound is oxidized to form a cation, and injection and transportation of holes from the mixed region into the light emitting medium is facilitated. Preferable examples of the oxidizing dopant include various types of Lewis acid and acceptor compounds. Preferable examples of the reductive dopant include alkali metals, compounds of alkali metals, alkaline earth metals, rare earth metals and compounds of these metals.

In the organic EL device of the present invention, the light emitting layer has the following functions:

(1) The injecting function: the function of injecting holes from the anode or the hole injecting layer and injecting electrons from the cathode or the electron injecting layer when an electric field is applied;

(2) The transporting function: the function of transporting injected charges (electrons and holes) by the force of the electric field; and (3) The light emitting function: the function of providing the field for recombination of electrons and holes and leading the recombination to the emission of light.

It is preferable to employ the foregoing compound of the present invention as the light emitting material composing the light emitting layer in the organic EL device of the present invention. In the case where the compound of the present invention is employed as the light emitting material, the compound may be used alone or in combination with any of publicly known light emitting materials. In the case where the compound of the present invention is employed for other than the light emitting layer, the light emitting material in the light emitting layer is not particularly restricted but may be selectively employed in option from among the conventional well known light emitting materials. For example, polycyclic condensed aromatics, fluorescent whitening agents such as benzoxazole base, benzothiazole base, benzimidazole base or so, and compounds having favorable thin film formation property such as metal chelated oxanoid compound, distyrylbenzene-based compound and so on are employed as the light emitting material. Examples of the polycyclic condensed aromatics include condensed ring light emitting substances containing anthracene, naphthalene, phenanthrene, pyrene, chrysene and perylene backbone structure, other condensed ring light emitting substances containing about 8 condensed rings, etc. Specifically, 1,1,4,4-tetraphenyl-1,3-butadiene, 4,4'-(2, 2-diphenyl vinyl) biphenyl and so on are employable as the light emitting material. The light emitting layer may be composed of single layer comprising one or more kind of these light emitting materials or may be laminated with a light emitting layer comprising another kind of compound.

As the process for forming the light emitting layer, a well known process such as the vapor deposition process, the spin coating process and the LB process can be employed. It is particularly preferable that the light emitting layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in the aggregation structure and higher order structures and functional differences caused by these structural differences.

As disclosed in Japanese Unexamined Patent Application Laid-Open No. Shou 57(1982)-51781, the light emitting layer can also be formed by dissolving a binder such as a resin and the material compounds into a solvent to prepare a solution, followed by forming a thin film from the prepared solution in accordance with the spin coating process or the like.

A hole injecting layer in the organic EL device of the present invention consists of a hole transfer compound, and is capable of transferring hole which is injected from the anode to the light emitting layer. By intervening the hole injecting layer between the anode and the light emitting layer, large numbers of holes are injected into the light emitting layer even though a relatively lower electric field is applied. Moreover, because electrons injected into the light emitting layer from the cathode or the electron injecting layer are, with the influence of an electronic barrier existing on interfacial area between the light emitting layer and the hole injecting layer, a superior organic EL device with favorable light emitting property such as improving an efficiency of light emission can be obtained.

The hole transfer compound used for such a hole injecting layer which is deployed between the two electrodes is capable of transferring holes adequately into the light emitting layer when the holes are injected from the anode. A compound which exhibits, for example, a mobility of holes of at least $10^{-6}$ $cm^2/V$. second under application of an electric field of from $10^4$ to $10^6$ V/cm is preferable as the hole transfer compound. With regard to the hole transfer compound, it is not particularly specified as long as it has the above favorable light emitting property. Namely, any compound may be selectively employed as the hole transfer compound from among compounds such as used in custom as charge injection and charge transport material of holes among a light conducting material or publicly known as the hole injecting layer of the organic EL device.

Examples of the above hole transfer compound include copper phthalocyanine, N,N,N',N' -tetraphenyl-4,4'-diaminophenyl, N,N'-diphenyl-N,N'-di(3-methylphenyl)-4,4'-diaminobiphenyl (TPDA), 2,2-bis (4-di-p-tolylaminophenyl) propane, 1,1-bis (4-di-p-tolylaminophenyl) cyclohexane, N,N,N',N'-tetra-p-tolyl-4,4'-diaminobiphenyl, etc. Further, crystals of inorganic semiconductor such as Si, SiC or CdS and amorphous material may be also employed as the hole transfer compound. The hole injecting layer may be composed of single layer comprising one or more kind of these hole injecting materials or may be laminated with a hole injecting layer comprising another kind of compound.

To form the hole injecting layer or the hole transporting layer, a thin film may be formed from the material for the hole injecting layer or the hole transporting layer, respectively, in accordance with a well known process such as the vacuum vapor deposition process, the spin coating process, the casting process and the LB process. Although the thickness of the hole injecting layer and the hole transporting layer is not particularly limited, the thickness is usually from 5 nm to 5 μm.

An electron injecting layer in the organic EL device of the present invention consists of an electron transfer material, and is capable of transferring electron which is injected from the cathode to the light emitting layer. In the organic EL device of the present invention, it is preferable to employ the foregoing compound of the present invention as the electron injecting material.

In the case where the compound of the present invention is employed for other than the electron injecting layer, the electron injecting material is not particularly restricted but may be selectively employed in option from among the conventional well known electron injecting material compounds. The reductive dopant used in the present invention is defined as a compound which is added to the interfacial region between the electron injecting layer and the cathode and enhances the effect of electron injection. In the present invention, an organic EL device containing a reductive dopant among the compound of the present invention is preferable. The reductive dopant is defined as the substance capable of reducing an electron transporting compound. Therefore, various substances with some extent of reductive property are employable as the reductive dopant. Examples of the reductive dopant include at least one compound selected from alkali metals, alkali metal complexes, alkali metal compounds, alkaline earth metals, alkaline earth metal complexes, alkaline earth metal compounds, rare earth metals, rare earth metal complexes and rare earth metal compounds.

Examples of the alkali metal include Na (the work function: 2.36 eV), K (the work function: 2.28 eV), Rb (the work function: 2.16 eV) and Cs (the work function: 1.95 eV).

Examples of the alkaline earth metal include Ca (the work function: 2.9 eV), Sr (the work function: 2.0 to 2.5 eV) and Ba (the work function: 2.52 eV).

Examples of the rare earth metal include Sc, Y, Eu, Tb, Ce, etc.

Examples of the alkali metal compound described above include alkali metal oxides such as $Li_2O$, $Cs_2O$, NaO, etc., and alkali metal halides such as LiF, NaF, KF, LiCl, KCl, NaCl, etc.

Examples of the alkaline earth metal oxide include CaO, BaO, SrO, BeO, etc.

Examples of the alkaline earth metal halide include fluorides such as $CaF_2$, $BaF_2$, $SrF_2$, $MgF_2$ and $BeF_2$, or halides except the fluorides.

Preferable reductive dopant has a work function of 2.9 eV or smaller. Specific examples of preferable reductive dopant include at least one kind or more of the alkaline metal selected from a group consisting of Na (the work function: 2.36 eV), K (the work function: 2.28 eV), Rb (the work function: 2.16 eV) and Cs (the work function: 1.95 eV). Further, the examples include at least one kind or more of the alkaline earth metal selected from a group consisting of Ca (the work function: 2.9 eV), Sr (the work function: 2.0-2.5 eV) and Ba (the work function: 2.52 eV). Among these, more preferable reductive dopants include at least one kind or more selected from the group consisting of K, Rb and Cs, the latter Rb or Cs being farther more preferable and the last Cs being the most preferable. These alkaline metals have particularly high reducing capability, and only an addition of relatively small amount of them into an electron injection zone enables to achieve both improvement of luminance and lifetime extension of the organic EL device. Further, a combination of two or more kinds of the alkaline metals is also preferable as the reductive dopant having the work function of 2.9 eV or smaller. In particular, a combination including Cs, for example, combinations of Cs and Na, Cs and K, Cs and Rb or Cs, Na and K are preferable. Containing Cs in combination enables to reveal reducing capability effectively, and the addition into the electron injection zone achieves both improvement of luminance and lifetime extension of the organic EL device. Also, aside from the alkali metals, even an employment of at least one or more kinds of metal compound selected from the group consisting of alkali metal chalcogenide, alkaline earth metal chalcogenide, halide of alkali metal and halide of alkaline earth metal also achieves similar effects. Still further, an employment of alkali metal organic complexes or alkaline earth metal organic complexes also achieves similar effects.

In the organic EL device of the present invention, an electron injecting layer comprising electric insulating material, semiconductor and inorganic compound may be disposed between the cathode and the organic layer. The disposition of the electron injecting layer enables to effectively prevent a leak of electric current and to improve the electron injection property. It is preferable that at least one metal compound selected from the group consisting of alkali metal chalcogenides, alkaline earth metal chalcogenides, alkali metal halides and alkaline earth metal halides is used as the insulating material. It is preferable that the electron transporting layer is constituted with the above alkali metal chalcogenide since the electron injecting property can be improved. Preferable examples of the alkali metal chalcogenide include $Li_2O$, LiO, $Na_2S$, $Na_2Se$ and NaO. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as $CaF_2$, $BaF_2$, $SrF_2$, $MgF_2$ and $BeF_2$and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound constituting the electron injection layer is in the form of a fine crystalline or amorphous insulating thin film. When the electron injection layer is constituted with the above inorganic compound, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

The electron injecting layer in the organic EL device of the present invention can be formed in accordance with the publicly known thin-film formation method such as the vacuum vapor deposition process, the spin coating process, the casting process or the LB process employing the compound of the present invention or other electron injection material. Although the thickness of the electron injecting layer is not particularly limited, the thickness is usually from 5 nm to 5 μm. The electron injecting layer may be composed of single layer comprising one or more kind of these electron injecting materials or may be laminated with an electron injecting layer comprising another kind of compound. Furthermore, inorganic hole injection materials such as p type-Si and p type-SiC, inorganic electron injection materials such as n type α-Si and n type α-SiC are employed as the electron injection material for composing electron injecting layer. Specific examples of the above electron injection material correspond to inorganic semiconductors disclosed in International Patent Publication No. WO 90/05998, etc.

Following is a description regarding a preparing method about the organic EL device of the present invention. An explanation about an organic EL device of anode/hole injecting layer/light emitting layer/electron injecting layer/cathode type example of the present invention will be described as a preferred embodiment hereinunder. First, a thin film consisting of a desired electrode substance, for example, a substance for the anode is formed over a suitable substrate so as to finally achieve a film thickness of 1 μm or thinner, preferably within a range from 10 nm to 200 nm in accordance with a vapor deposition method, a sputtering method, etc. Then, the hole injecting layer, the light emitting layer and the electron injecting layer which are all EL device composing elements are made by successively forming thin films consisting of each composing material into multi layers. With regard to a thin film formation process to be used, there are the spin coating process, the casting process or the vapor deposition process as the foregoing description. A vacuum vapor deposition process is preferable because a uniform film can be easily obtained and the possibility of formation of pin holes is small. In the case where the vacuum vapor deposition process is adopted as the thin film formation process, the vapor deposition condition is different according to the kind of the compound employed, a crystal structure or an association structure each as an object of molecular pile membrane. However, it is generally preferable to appropriately select among port heat temperature of 50 to 400 ° C., vacuum of $10^{-6}$ to $10^{-3}$ Pa, vapor deposition rate of 0.01 to 50 nm/second, substrate temperature of −50 to 300 ° C., and film thickness of 5 nm to 5 u m respectively. After forming the above layers, a thin film consisting of a cathode substance is formed thereupon into a film thickness of 1 μm or thinner, preferably within a range from 50 to 200 nm, in accordance with, for example, the vapor deposition process or the sputtering process, thereby making cathode and resultantly obtaining a desired organic EL device. Additionally, in preparation of the organic EL device, reversing the formation order, a formation in order of the cathode, the electron injecting layer, the light emitting layer, the hole injecting (transporting) layer and the anode may be applicable.

In the above production of the organic EL device, it is preferable that the above layers from the anode to the cathode are formed successively while the production system is kept in a vacuum after being evacuated.

Further, a preparation of an organic EL device of the anode/the light emitting layer/the cathode type wherein a hole injecting layer, a light emitting layer and an electron injecting layer as coexisting sandwiched between a pair of electrode is as the following: For example, forming a thin film consisting of anode substance over a suitable substrate, making a light emitting layer (or, a light emission area) by applying or dip coating a solution comprising a hole injection material, a light emitting material, electron injection material and a binder such as polyvinylcarbazole, polycarbonate, polyacrylate, polyester and polyether or so and, thereupon, forming a film consisting of cathode substance. After further vacuum vapor deposition of device materials which correspond to the light emitting layer or the electron injecting layer over the formed light emitting layer, the film consisting of cathode substance may be formed thereupon.

The organic EL device which can be produced as described above emits light when a direct voltage of 3 to 50 V is applied in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any, type of wave shape can be employed.

Employing the derivative of heterocyclic compound having nitrogen atom of the present invention for the organic compound layer, particularly for the electron injecting layer, adhesion between the organic compound layer containing the compound of the present invention and the electrode (particularly, cathode) in the organic EL device of a the present invention is improved.

The organic EL device of the present invention prepared as the foregoing description achieves high brightness and excellent efficiency of light emission.

The present invention will be described more specifically with reference to examples and synthesis examples in the following. However, the present invention is not limited to the examples.

SYNTHESIS EXAMPLE 1

Synthesis of Compound (1-1)

(1) Synthesis of 3-anthracen-9-yl-1-phenyl-propenone

Twenty five grams (0.12 mol) of anthracene-9-aldehyde was dissolved in 800 milliliter of ethanol. The resultant solution was mixed with 15 g (0.12 mol) of acetophenone and 23 g (0.12 mol) of a 28% sodium methoxide methanol solution, and stirred at room temperature for 4 hours. After completion of the reaction, the precipitated solids were separated by filtration and washed with methanol, thereby obtaining 34.0 g of 3-anthracen-9-yl-1-phenyl-propenone (yield: 91%).

(2) Synthesis of 4-anthracene-9-yl-2,6-diphenyl-pyrimidine

Twenty grams (65 mmol) of 3-anthracen-9-yl-1-phenyl-propenone obtained in the above step (1) was dissolved in 200 milliliter of ethanol. The resultant solution was mixed with 10 g (65 mmol) of benzamidine hydrochloride and 5.4 g (0.13 mol) of sodium hydroxide, and the resultant suspension was refluxed under heating for 25 hours. After completion of the reaction, the solution was cooled down to room temperature, then, precipitated crystals were separated by filtration and washed with water and methanol, thereby obtaining 19.1 g of 4-anthracen-9-yl-2,6-diphenyl-pyrimidine (yield: 72%).

(3) Synthesis of 4-(10-bromo-anthracen-9-yl)-2,6-diphenyl-pyrimidine

Dissolving 19 g (47 mmol) of 4-anthracen-9-yl-2,6-diphenyl-pyrimidine obtained in the foregoing step (2) into 200 milliliter of N,N-dimethylformamide, and adding 9.2 g (52 mmol) of N-bromosuccinimide, stirred at room temperature for 8 hours. After completion of the reaction, precipitated solids were separated by filtration and washed with water and methanol, thereby obtaining 14.9 g of 4-(10-bromo-anthracen-9-yl)-2,6-diphenyl-pyrimidine (yield: 66%).

(4) Synthesis of 2,4-diphenyl-6-(10-phenyl-anthracen-9-yl)-pyrimidine (Compound 1-1)

Two grams (4.1 mmol) of 4-(10-bromo-anthracen-9-yl)-2,6-diphenyl-pyrimidine obtained in the above step (3), 0.60 g (4.9 mmol) of phenylboronic acid and 0.10 g of tetrakis (triphenylphosphine) palladium into 20 milliliter of 1,2-dimethoxyethane, and adding 8 milliliter of 2.OM sodium carbonate aqueous solution, the resultant suspension was refluxed under heating for 7 hours. After completion of the reaction, the precipitated solids were dissolved into the dichloro-methane, washed with water and dried with anhydrous sodium sulfate. The solvent was removed by distillation and the resultant substance was washed with methanol thereby obtaining 1.8 g of yellowish white solids (yield: 91%). As a result of mass spectrum (MS) analysis, the yellowish white solids were identified as the aimed substance (Compound 1-1), and it was recognized that m/e=484 for molecular weight of 484.19.

SYNTHESIS EXAMPLE 2

Synthesis of 4-(10-naphthalen-1-yl-anthracene-9-yl)-2,6-diphenyl-pyrimidine (Compound 1-3)

Conducting the same procedure as the foregoing Synthesis Example 1 except that corresponding boronic acid was used instead of phenylboronic acid, an aimed substance (Compound 1-3) was obtained (yield: 86%).

In accordance with mass spectrum (MS) analysis, it was recognized that m/e=534 for molecular weight of 534.21.

SYNTHESIS EXAMPLE 3

Synthesis of 4-(10-naphthalen-2-yl-anthracene-9-yl)-2,6-diphenyl-pyrimidine (Compound 1-4)

Conducting the same procedure as the foregoing Synthesis Example 1 except that corresponding boronic acid was used instead of phenylboronic acid, an aimed substance (Compound 1-4) was obtained (yield: 99%).

In accordance with mass spectrum (MS) analysis, it was recognized that m/e=534 for molecular weight of 534.21.

SYNTHESIS EXAMPLE 4

Synthesis of Compound (1-10)

(1) Synthesis of 3-anthracene-9-yl-1-naphthalen-1-yl-propenon

Ten grams (48 mmol) of anthracene-9-aldehyde was dissolved in 300 milliliter of ethanol. The resultant solution was mixed with 8.3 g (49 mmol) of 1-acetylnaphthalene and 9.4 g (49 mmol) of 28% sodium methoxide methanol solution, and stirred at room temperature for 4 hours. After completion of reaction, precipitated solids were separated by filtration and washed with methanol, thereby obtaining 16.6 g of 3-anthracen-9-yl-1-naphthalen-1-yl-propenon (yield: 95%).

(2) Synthesis of 4-anthracene-9-yl-6-naphthalen-1-yl-2-phenyl-pyrimidine

Ten grams (28 mmol) of 3-anthracen-9-yl-1-phenyl-propenone obtained in the above step (1) was dissolved in 100 milliliter of ethanol. The resultant solution was mixed with 4.4 g (28 mmol) of benzamidine hydrochloride and 2.3 g (57 mmol) of sodium hydroxide, and the resultant suspension was refluxed under heating for 25 hours. After completion of the reaction, the solution was cooled down to room temperature, then, precipitated crystals were separated by filtration and washed with water and methanol, thereby obtaining 8.5 g of 4-anthracen-9-yl-6-naphthalen-1-yl-phenylpyrimidine (yield: 67%).

(3) Synthesis of 4-(10-bromo-anthracen-9-yl)-6-naphthalen-1-yl-2-phenyl-pyrimidine Dissolving 8.5 g (19 mmol) of 4-anthracen-9-yl-6-naphthalen-1-yl-phenyl-pyrimidine obtained in the foregoing step (2) into 100 milliliter of N,N-dimethylformamide, and adding 3.6 g (20 mmol) of N-bromosuccinimide, stirred at room temperature for 8 hours. After completion of the reaction, precipitated solids were separated by filtration and washed with water and methanol, thereby obtaining 7.2 g of 4-(10-bromo-anthracen-9-yl)-6-naphthalen-1-yl-phenyl-pyrimidine (yield: 73%).

(4) Synthesis of 4-naphthalene-1-yl-6-(10-naphthalen-1-yl-anthracene-9-yl)-2-phenyl-pyrimidine (Compound 1-10)

Two point two grams (4.1 mmol) of 4-(10-bromo-anthracen-9-yl)-6-naphthalen-1-yl-phenyl-pyrimidine obtained in the above step (3), 0.85 g (5.1 mmol) of naphthaleneboronic acid and 0.11 g of tetrakis (triphenylphosphine) palladium into 20 milliliter of 1,2-dimethoxyethane, and adding 8 milliliter of 2.0M sodium carbonate aqueous solution, the resultant suspension was refluxed under heating for 8 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.33 g of yellowish white solid (yield: 97%). As a result of mass spectrum (MS) analysis, the yellowish white solids were identified as the aimed substance (Compound 1-10), and it was recognized that m/e 584 for molecular weight of 584.23.

SYNTHESIS EXAMPLE 5

Synthesis of 4-naphthalen-1-yl-6-(10-naphthalen-2-yl-anthracene-9-yl)-2-phenyl-pyrimidine (Compound 1-11)

Conducting the same procedure as the foregoing Synthesis Example 4 except that corresponding boronic acid was used instead of 1-naphthalene boronic acid, an aimed substance (Compound 1-11) was obtained (yield: 97%).

In accordance with mass spectrum (MS) analysis, it was recognized that m/e=584 for molecular weight of 584.23.

SYNTHESIS EXAMPLE 6

Synthesis of Compound (2-4)

(1) Synthesis of 3-(4-bromo-phenyl)-1-phenyl-propenone

Fifteen grams (81 mmol) of 4-bromobenzaldehyde was dissolved in 300 milliliter of ethanol. The resultant solution was mixed with 10 g (83 mmol) of acetophenone and 15 g (81 mmol) of a 28% sodium methoxide methanol solution, and stirred at room temperature for 7 hours. After completion of reaction, precipitated solids were separated by filtration and washed with methanol, thereby obtaining 19.4 g of 3-(4-bromo-phenyl)-1-phenyl-propenone (yield: 83%).

(2) Synthesis of 4-(4-bromo-phenyl)-2,6-diphenyl-pyrimidine

Nineteen grams (67 mmol) of 3-(4-bromo-phenyl)-1-phenyl-propenon obtained in the above step (1) was dissolved in 150 milliliter of ethanol. The resultant solution was mixed with 10.6 g (69 mmol) of benzamidine hydrochloride and 5.5 g (138 mmol) of sodium hydroxide, and the resultant suspension was refluxed under heating for 12 hours. After completion of the reaction, the solution was cooled down to room temperature, then, precipitated crystals were separated by filtration and washed with water and methanol, thereby obtaining 15.9 g of 4-(4-bromo-phenyl)-2,6-diphenyl-pyrimidine (yield: 61%).

(3) Synthesis of 4-[4-(10-naphthalen-2-yl-anthracen-9-yl)-phenyl]-2,6-diphenyl-pyrimidine (Compound 2-4)

One point eight grams (4.6 mmol) of 4-(4-bromo-phenyl)-2,6-diphenyl-pyrimidine obtained in the above step (2), 1.6 g (4.6 mmol) of 10-naphthalen-2-yl-anthrathene-9-boronic acid and 0.11 g of tetrakis (triphenylphosphine) palladium into 20 milliliter of 1,2-dimethoxyethane, and adding 7 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.1 g of yellowish white solid (yield: 74%). As a result of mass spectrum (MS) analysis, the yellowish white solids were identified as the aimed substance (Compound 2-4), and it was recognized that m/e=610 for molecular weight of 610.24.

SYNTHESIS EXAMPLE 7

Synthesis of Compound (3-3)

(1) Synthesis of a 3-anthracen-9-yl-1-pyridine-2-yl-propenon

Ten grams (48 mmol) of anthracene-9-aldehyde was dissolved in 300 milliliter of ethanol. The resultant solution was mixed with 5.9 g (49 mmol) of 2-acetylpyridine and 9.4 g (49 mmol) of 28% sodium methoxide methanol solution, and stirred at room temperature for 4 hours. After completion of reaction, precipitated solids were separated by filtration and washed with methanol, thereby obtaining 14.2 g of 3-anthracen-9-yl-1-pyridine-2-yl-propenon (yield: 95%).

(2) Synthesis of 4-anthracen-9-yl-2-phenyl-6-pyridine-2-yl-pyrimidine

Ten grams (32 mmol) of 3-anthracen-9-yl-1-pyridine-2-yl-propenon obtained in the above step (1) was dissolved in 100 milliliter of ethanol. The resultant solution was mixed with 5.1 g (33 mmol) of benzamidine hydrochloride and 2.6 g (65 mmol) of sodium hydroxide, and the resultant suspension was refluxed under heating for 25 hours. After completion of the reaction, the solution was cooled down to room temperature, then, precipitated crystals were separated by filtration and washed with water and methanol, thereby obtaining 12.4 g of 4-anthracen-9-yl-2-phenyl-6-pyridine-2-yl-pyrimidine (yield: 94%).

(3) Synthesis of 4-(10-bromo-anthracen-9-yl)-2-phenyl-6-pyridine-2-yl-pyrimidine Dissolving 12 g (30 mmol) of 4-anthracen-9-yl-2-phenyl-6-pyridine-2-yl-pyrimidine obtained in the foregoing step (2) into 100 milliliter of N,N-dimethylformamide, and adding 5.9 g (33 mmol) of N-bromosuccinimide, stirred at room temperature for 8 hours. After completion of the reaction, precipitated solids were separated by filtration and washed with water and methanol, thereby obtaining 10.8 g of 4-(10-bromo-anthracen-9-yl)-2-phenyl-6-pyridine-2-yl-pyrimidine (yield: 73%).

(4) Synthesis of 4-(10-naphthalen-1-yl-anthracen-9-yl)-2-phenyl-6-pyridine-2-yl-pyrimidine (Compound 3-3)

Two point two grams (4.5 mmol) of 4-(10-bromo-anthracen-9-yl)-2-phenyl-6-pyridine-2-yl-pyrimidine obtained in the above step (2), 0.88 g (5.1 mmol) of 1-naphthaleneboronic acid and 0.11 g of tetrakis (triphenylphosphine) palladium into 20 milliliter of 1,2-dimethoxyethane, and adding 8 milliliter of 2.OM sodium carbonate aqueous solution, the resultant suspension was refluxed under heating for 8 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.5 g of yellowish white solid (yield: 99%). As a result of mass spectrum (MS) analysis, the yellowish white solids were identified as the aimed substance (Compound 3-3), and it was recognized that m/e=535 for molecular weight of 535.20.

SYNTHESIS EXAMPLE 8

Synthesis of 4-(10-naphthalen-2-yl-anthracene-9-yl)-2-phenyl-6-pyridine-2-yl-pyrimidine (Compound 3-4)

Conducting the same procedure as the foregoing Synthesis Example 7 except that corresponding boronic acid was used instead of 1-naphthaleneboronic acid, an aimed substance (Compound 3-4) was obtained (yield: 92%/o).

In accordance with mass spectrum (MS) analysis, it was recognized that m/e=535 for molecular weight of 535.20.

SYNTHESIS EXAMPLE 9

Synthesis of 4'-(10-naphthalen-2-yl-anthracene-9-yl)-[2,2';6',2"] terpyridine (Compound 5-4)

Two grams (5.7 mmol) of 4'-chloro-[2,2';6',2"] terpyridine, 2.0 g (5.7 mmol) of 10-naphthalen-2-yl-anthrathene-9-boronic acid and 0.14 g of tetrakis (triphenylphosphine) palladium into 20 milliliter of 1,2-dimethoxyethane, and adding 9 milliliter of 2.0M sodium carbonate aqueous solution, the resultant suspension was refluxed under heating for 7 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.33 g of yellowish white solid (yield: 84%). As a result of mass spectrum (MS) analysis, the yellowish white solids were identified as the aimed substance (Compound 5-4), and it was recognized that m/e=535 for molecular weight of 535.20.

SYNTHESIS EXAMPLE 10

Synthesis of Compound (6-18)

(1) Synthesis of 6-(4-bromo-phenyl)-3-phenyl-[1,2,4] triazine

Dissolving 5.0 g (18 mmol) of 2,4'-dibromoacetophenone and 4.9 g (36 mmol) of benzoylhydrazine into 20 milliliter of acetic acid, adding 1.5 g of sodium acetate, the resultant suspension was refluxed under heating for 10 hours. After completion of the reaction, adding water and an extraction was carried out using dichloro-methane. After the reaction fluid was separated into two layers, the organic layer was washed with a solution of sodium chloride and dried with anhydrous sodium sulfate. The solvent was removed by distillation and the resultant substance was washed with methanol, thereby obtaining 1.6 g of 6-(4-bromo-phenyl)-3-phenyl-[1,2,4] triazine (yield: 29%).

(2) Synthesis of 6-[4-(10-naphthalen-2-yl-anthracen-9-yl)-phenyl]-3-phenyl-[1,2,4] triazine (Compound 6-18)

One point six grams (5.1 mmol) of 6-(4-bromo-phenyl)-3-phenyl-[1,2,4] triadine obtained in the above step (1), 1.8 g (5.2 mmol) of 10-naphthalen-2-yl-anthrathene-9-boronic acid and 0.10 g of tetrakis (triphenylphosphine) palladium into 20 milliliter of 1,2-dimethoxyethane, and adding 10 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 1.17 g of yellowish white solid (yield: 43%). As a result of mass spectrum (MS) analysis, the yellowish white solids were identified as the aimed substance (Compound 6-18), and it was recognized that m/e=535 for molecular weight of 535.20.

SYNTHESIS EXAMPLE 11

Synthesis of Compound (8-4)

(1) Synthesis of 2-(4-bromo-phenyl)-quinoxaline

Ten grams (36 mmol) of 2,4'-dibromo acetophenone and 4.0 g (37 mmol) of 1,2-phenylenediamine were refluxed under heating among 20 milliliter of ethanol for 3.5 hours. After completion of the reaction, resultant crystals were separated with filtration, washed with ethanol, thereby obtaining 4.2 g of 2-(4-bromo-phenyl)-quinoxaline (yield: 41%).

(2) Synthesis of 2-(4-anthracen-9-yl-phenyl)-quinoxaline

Two grams (7.0 mmol) of 4-(4-bromo-phenyl)-quinoxaline obtained in the above step (1), 1.7 g (7.7 mmol) of 9-anthratheneboronic acid and 0.16 g of tetrakis (triphenylphosphine) palladium into 20 milliliter of 1,2-dimethoxyethane, and adding 12 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.37 g of 2-(4-anthracen-9-yl-phenyl)-quinoxaline (yield: 88%).

(3) Synthesis of 2-[4-(10-bromo-anthracen-9-yl)-phenyl]-quinoxaline

Dissolving 2.2 g (6.2 mmol) of 2-(4-anthracen-9-yl-phenyl) quinoxaline obtained in the foregoing step (2) into 20 milliliter of N,N-dimethylformamide, and adding 1.2 g (6.7 mmol) of N-bromosuccinimide, stirred at room temperature for 8 hours. After completion of the reaction, precipitated solids were separated by filtration and washed with water and methanol, thereby obtaining 14.9 g of 2-[4-(10-bromo-anthracen-9-yl)-phenyl]-quinoxaline (yield: 78%).

(4) Synthesis of 2-[4-(10-naphthalen-2-yl-anthracen-9-yl)-phenyl]-quinoxaline (Compound 8-4)

Two point two grams (4.8 mmol) of 2-[4-(10-bromo-anthracen-9-yl)-phenyl]-quinoxaline obtained in the above step (3), 0.98 g (5.7 mmol) of 2-naphthaleneboronic acid and 0.11 g of tetrakis (triphenylphosphine) palladium into 20 milliliter of 1,2-dimethoxyethane, and adding 8 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.4 g of yellowish white solid (yield: 99%). As a result of mass spectrum (MS) analysis, the yellowish white solids were identified as the aimed substance (Compound 8-4), and it was recognized that m/e=508 for molecular weight of 508.19.

SYNTHESIS EXAMPLE 12

Synthesis of Compound (10-18)

(1) Synthesis of 2-(4-bromo-phenyl)-4-phenyl-quinoline

Dissolving 5.0 g (25 mmol) of 4-bromoacetophenone and 5.0 g (25 mmol) of 2-aminobenzophenon into 50 milliliter of ethanol, adding 3.1 g of sodium hydroxide, the resultant suspension was refluxed under heating for 7 hours. After completion of the reaction, separation with filtration was carried out and resultant crystals were washed with water and ethanol, thereby obtaining 5.56 g of 2-(4-bromo-phenyl)-quinoline (yield: 61%).

(2) Synthesis of 2-[4-(10-naphthalen-2-yl-anthracen-9-yl)-phenyl]-4-phenyl-quinoline (Compound 10-18)

Two grams (5.6 mmol) of 2-(4-bromo-phenyl)-4-phenyl-quinoline obtained in the above step (1), 2.0 g (5.7 mmol) of 10-naphthalen-2-yl-anthrathene-9-boronic acid and 0.10 g of tetrakis (triphenylphosphine) palladium into 20 milliliter of 1,2-dimethoxyethane, and adding 8 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.07 g of yellowish white solid (yield: 64%). As a result of mass spectrum (MS) analysis, the yellowish white solids were identified as the aimed substance (Compound 10-18), and it was recognized that m/e=583 for molecular weight of 583.23.

SYNTHESIS EXAMPLE 13

Synthesis of Compound (14-7)

(1) Synthesis of 2-(4-bromo-phenyl)-imidazo [1,2-a] pyridine

Dissolving 15 g (54 mmol) of 4-bromoacetophenone and 5.2 g (55 mmol) of 2-aminopyridine into 100 milliliter of ethanol, adding 7.0 g of sodium hydroxide, the resultant suspension was refluxed under heating for 6 hours. After completion of the reaction, resultant crystals were separated with filtration, washed with water and ethanol, thereby obtaining 12.5 g of 2-(4-bromo-phenyl)-imidazo [1,2-a] pyridine (yield: 85%).

(2) Synthesis of 2-[4-(10-naphthalen-2-yl-anthracen-9-yl)-phenyl]-imidazo [1,2-a] pyridine (Compound 14-7)

One point five grams (5.5 mmol) of 2-(4-bromo-phenyl)-imidazo [1,2-a] pyridine obtained in the above step (1), 2.0 g (5.78 mmol) of 10-naphthalen-2-yl-anthrathene-9-boronic acid and 0.13 g of tetrakis (triphenylphosphine) palladium into 30 milliliter of 1,2-dimethoxyethane, and adding 8.6 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 1.2 g of yellowish white solid (yield: 45%). As a result of mass spectrum (MS) analysis, the yellowish white solids were identified as the aimed substance (Compound 14-7), and it was recognized that m/e=496 for molecular weight of 496.19.

SYNTHESIS EXAMPLE 14

Synthesis of 9-(10-naphthalen-2-yl-anthracen-9-yl)-acridine (Compound 13-4)

One point three grams (6.1 mmol) of 9-chloro-acridine, 2.0 g (5.7 mmol) of 10-naphthalen-2-yl-anthrathene-9-boronic acid and 0.10 g of tetrakis (triphenylphosphine) palladium into 20 milliliter of 1,2-dimethoxyethane, and adding 8 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 2.16 g of yellowish white solid (yield: 74%). As a result of mass spectrum (MS) analysis, the yellowish white solids were identified as the aimed substance (Compound 13-4), and it was recognized that m/e=481 for molecular weight of 481.18.

SYNTHESIS EXAMPLE 15

Synthesis of 9-[4-(10-naphthalen-2-yl-anthracene-9-yl)-phenyl]-acridine (Compound 13-11)

One point six grams (4.8 mmol) of 4-(4-bromo-phenyl)-acridine, 1.6 g (4.6 mmol) of 10-naphthalen-2-yl-anthrathene-9-boronic acid and 0.11 g of tetrakis (triphenylphosphine) palladium into 20 milliliter of 1,2-dimethoxyethane, and adding 7 milliliter of 2.0M sodium carbonate aqueous solution, the resultant suspension was refluxed under heating for 6 hours. After completion of the reaction, the precipitated solids were dissolved into the dichloro-methane, washed with water and dried with anhydrous sodium sulfate. The solvent was removed by distillation and the resultant substance was washed with methanol thereby obtaining 1.98 g of yellowish white solid (yield: 74%). As a result of mass spectrum (MS) analysis, the yellowish white solids were identified as the aimed substance (Compound 13-11), and it was recognized that m/e=557 for molecular weight of 557.21.

SYNTHESIS EXAMPLE 16

Synthesis of 2-[4-(10-phenylanthracen-9-yl)-phenyl]-imidazo [1,2-a] pyridine (Compound 14-1)

The same procedure as step (2) in Synthesis Example 13 was conducted except that 10-phenyl anthracene-9-boronic acid was used instead of 10-naphthalen-2-yl-anthracene-9-boronic acid, thereby obtaining 3.4 g of yellowish white solids (yield: 78%). As a result of mass spectrum (MS) analysis, the yellowish white solids were identified as the aimed substance (Compound 14-1), and it was recognized that m/e=446 for molecular weight of 446.18.

SYNTHESIS EXAMPLE 17

Synthesis of 2-[4-(10-biphenyl-2-yl-anthracene-9-yl)-phenyl]-imidazo[1,2-a]pyridine (Compound 14-2)

The same procedure as step in Synthesis Example 13 (2) was conducted except that 10-biphenyl-2-yl-anthracene-9-boronic acid was used instead of 10-naphthalen-2-yl-anthracene-9-boronic acid, thereby obtaining 3.4 g of yellowish white solids (yield: 81%). As a result of mass spectrum (MS) analysis, the yellowish white solids were identified as the aimed substance (Compound 14-2), and it was recognized that m/e=522 for molecular weight of 522.21.

SYNTHESIS EXAMPLE 18

Synthesis of 2-[4-(10-naphthalen-1-yl-anthracene-9-yl)-phenyl]-imidazo [1,2-a] pyridine (Compound 14-6)

The same procedure as step in Synthesis Example 13 (2) was conducted except that 10-naphthalen-1-yl-anthracene-9-boronic acid was used instead of 10-naphthalen-2-yl-anthracene-9-boronic acid, thereby obtaining 2.6 g of yellowish white solids (yield: 72%). As a result of mass spectrum (MS) analysis, the yellowish white solids were identified as the aimed substance (Compound 14-6), and it was recognized that m/e=496 for molecular weight of 496.19.

SYNTHESIS EXAMPLE 19

Synthesis of Compound (14-5)

(1) Synthesis of 2-[4-(10-bromo-anthracen-9-yl)-phenyl]-imidazo [1,2-a]pyridine

Dissolving 20 g (81 mmol) of 4'-iodo acetophenone into 200 milliliter of acetic acid, and adding 12.8 g (81 mmol) of bromine while cooling with ice, stirred at the temperature of 15° C. for 3 hours. After the color of bromine disappeared, adding water and separating the precipitated solids by filtration, thereby obtained 27 g of crude 2-bromo-4'-iodo acetophenone.

Dissolving 27 g (83 mmol) of crude 2-bromo-4'-iodo acetophenone thus obtained and 8.0 g (85 mmol) of 2-aminopyridine into 200 milliliter of ethanol, adding 10 g of sodium hydrogen carbonate, the resultant suspension was refluxed under heating for 6 hours. After completion of the reaction, separation with filtration was carried out and resultant crystals were washed with water and ethanol, thereby obtaining 21 g of 2-(4-iodophenyl)-imidazo [1,2-a] pyridine (yield: 82%).

Ten point six grams (33 mmol) of 2-(4-iodophenyl)-imidazo [1,2-a] pyridine, 10 g (33 mmol) of 10-bromoanthracene-9-boronic acid and 0.77 g of tetrakis (triphenylphosphine) palladium were dissolved into 100 milliliter of 1,2-dimethoxyethane, and adding 50 milliliter of 2.0M sodium carbonate aqueous solution, the resultant suspension was refluxed under heating for 7 hours. After completion of the reaction, separation with filtration was carried out and resultant crystals were washed with water and methanol, thereby obtaining 11.7 g of 2-[4-(10-bromo-anthracene-9-yl)-phenyl]-imidazo [1,2-a] pyridine (yield: 78%).

(2) Synthesis of 2-[4-(10-[1,1';3',1"]terphenyl-5'-yl-anthracen-9-yl)-phenyl]-imidazo [1,2-a] pyridine (Compound 14-5)

Two point five grams (5.5 mmol) of 2-[4-(10-bromo-anthracen-9-yl)-phenyl]-imidazo [1,2-a] pyridine, 1.6 g (5.8 mmol) of [1,1';3',1"] terphenyl-5'-boronic acid and 0.13 g of tetrakis (triphenylphosphine) palladium were dissolved into 20 milliliter of 1,2-dimethoxyethane, and adding 9 milliliter of 2.0M sodium carbonate aqueous solution, the resultant suspension was refluxed under heating for 8 hours. After completion of the reaction, separation with filtration was carried out and resultant crystals were washed with water and methanol, thereby obtaining 2.4 g of yellowish white solids (yield: 71%). As a result of mass spectrum (MS) analysis, the yellowish white solids were identified as the aimed substance, and it was recognized that m/e=598 for molecular weight of 598.24.

SYNTHESIS EXAMPLE 20

Synthesis of 2-[4-(10-phenanthrene-9-yl-anthracen-9-yl)-phenyl]-imidazo [1,2-a] pyridine (Compound 14-8)

Almost the same procedure as Synthesis Example 19 was carried out except that 9-phenanthrene boronic acid was used instead of [1,1';3',1"] terphenyl-5'-boronic acid, resultantly obtaining 2.4 g of yellowish white solids (yield: 78%). As a result of mass spectrum (MS) analysis, the yellowish white solids were identified as the aimed substance (Compound 14-8), and it was recognized that m/e=446 for molecular weight of 446.18.

SYNTHESIS EXAMPLE 21

Synthesis of 2-[4-(10-fluoranthene-3-yl-anthracen-9-yl)-phenyl]-imidazo [1,2-a] pyridine (Compound 14-9)

Almost the same procedure as Synthesis Example 19 was carried out except that 3-fluoranthene boronic acid was used instead of [1,1';3',1"] terphenyl-5'-boronic acid, resultantly obtaining 2.5 g of yellowish white solids (yield: 93%). As a result of mass spectrum (MS) analysis, the yellowish white solids were identified as the aimed substance (Compound 14-9), and it was recognized that m/e=570 for molecular weight of 570.21.

SYNTHESIS EXAMPLE 22

Synthesis of Compound (15-1)

(1) Synthesis of 2-(4-bromo-phenyl)-3-methyl-imidazo [1,2-a] pyridine

Dissolving 5.0 g (23 mmol) of 4'-bromopropiophenon into 50 milliliter of acetic acid, and adding 3.7 g (23 mmol) of bromine while cooling with ice, stirred at the temperature of 10° C. for 3 hours. After the color of bromine disappeared, adding water and an extraction was carried out using dichloro-methane. Washing the organic layer with water, it was dried with the use of sodium sulfate. The solvent was removed by distillation and the resultant crystals were washed with hexane thereby obtaining 4.3 g of 2,4'-dibromopropiophenon (yield: 63%).

Dissolving 4.3 g (16 mmol) of 2,4'-dibromopropiophenon obtained and 1.4 g (15 mmol) of 2-aminopyridine into 50 milliliter of ethanol, adding 1.9 g of sodium hydrogen carbonate, the resultant suspension was refluxed under heating for 6 hours. After completion of the reaction, adding water and an extraction was carried out using dichloro-methane. Washing the organic layer with water, it was dried with the use of sodium sulfate. The solvent was removed by distillation and the resultant syrup was refined by silica gel column chromatography thereby obtaining 1.6 g of 2-(4-bromo-phenyl)-3-methyl-imidazo [1,2-a] pyridine (yield: 37%).

(2) Synthesis of 2-[4-(10-naphthalen-2-yl-anthracen-9-yl)-phenyl]-3-methyl-imidazo [1,2-a] pyridine (Compound 15-1)

Almost the same procedure as step (2) in Synthesis Example 13 was carried out except that 2-(4-bromo-phenyl)-3-methyl-imidazo [1,2-a] pyridine was used instead of 2-(4-bromo-phenyl)-imidazo [1,2-a] pyridine, resultantly obtaining 1.9 g of yellowish white solids (yield: 70%). As a result of mass spectrum (MS) analysis, the yellowish white solids were identified as the aimed substance (Compound 15-1), and it was recognized that m/e=510 for molecular weight of 510.23.

SYNTHESIS EXAMPLE 23

Synthesis of Compound (15-3)

(1) Synthesis of 2-(4-bromo-phenyl)-6-methyl-imidazo [1,2-a] pyridine

Dissolving 5 g (18 mmol) of 2,4'-dibromo acetophenone and 2.0 g (19 mmol) of 2-amino-5-picoline into 30 milliliter of ethanol, adding 2.9 g of sodium hydrogen carbonate, the resultant suspension was refluxed under heating for 6 hours. After completion of the reaction, separation with filtration was carried out and resultant crystals were washed with water and ethanol, thereby obtaining 4.2 g of 2-(4-bromo-phenyl)-6-methyl-imidazo [1,2-a] pyridine (yield: 81%).

(2) Synthesis of 2-[4-(10-naphthalen-2-yl-anthracen-9-yl)-phenyl]-6-methyl-imidazo [1,2-a] pyridine (Compound 15-3)

Almost the same procedure as step (2) in Synthesis Example 13 was carried out except that 2-(4-bromo-phenyl)-6-methyl-imidazo [1,2-a] pyridine was used instead of 2-(4-bromo-phenyl)-imidazo [1,2-a] pyridine, resultantly obtaining 1.6 g of yellowish white solids (yield: 55%). As a result of mass spectrum (MS) analysis, the yellowish white solids were identified as the aimed substance (Compound 15-3), and it was recognized that m/e=510 for molecular weight of 510.23.

SYNTHESIS EXAMPLE 24

Synthesis of Compound (15-4)

(1) Synthesis of 2-(4-bromo-phenyl)-7-methyl-imidazo [1,2-a] pyridine

Almost the same procedure as step (1) in Synthesis Example 23 was carried out except that 2-amino-4-picoline was used instead of 2-amino-5-picoline, resultantly obtaining 2.8 g of 2-(4-bromo-phenyl)-7-methyl-imidazo [1,2-a] pyridine (yield: 54%).

(2) Synthesis of 2-[4-(10-naphthalen-2-yl-anthracen-9-yl)-phenyl]-7-methyl-imidazo [1,2-a] pyridine (Compound 15-4)

Almost the same procedure as step (2) in Synthesis Example 13 was carried out except that 2-(4-bromo-phenyl)-7-methyl-imidazo [1,2-a] pyridine was used instead of 2-(4-bromo-phenyl)-imidazo [1,2-a] pyridine, resultantly obtaining 1.6 g of yellowish white solids (yield: 57%). As a result of mass spectrum (MS) analysis, the yellowish white solids were identified as the aimed substance (Compound 15-4), and it was recognized that m/e=510 for molecular weight of 510.21.

SYNTHESIS EXAMPLE 25

Synthesis of Compound (15-5)

(1) Synthesis of 2-(4-bromo-phenyl)-8-methyl-imidazo [1,2-a] pyridine

Almost the same procedure as step (1) in Synthesis Example 23 was carried out except that 2-amino-3-picoline was used instead of 2-amino-5-picoline, resultantly obtaining 3.5 g of 2-(4-bromo-phenyl)-8-methyl-imidazo [1,2-a] pyridine (yield: 68%).

(2) Synthesis of 2-[4-(10-naphthalen-2-yl-anthracen-9-yl)-phenyl]-8-methyl-imidazo [1,2-a] pyridine (Compound 15-5)

Almost the same procedure as step (2) in Synthesis Example 13 was carried out except that 2-(4-bromo-phenyl)-8-methyl-imidazo [1,2-a] pyridine was used instead of 2-(4-bromo-phenyl)-imidazo [1,2-a] pyridine, resultantly obtaining 1.8 g of yellowish white solids (yield: 64%). As a result of mass spectrum (MS) analysis, the yellowish white solids were identified as the aimed substance (Compound 15-5), and it was recognized that m/e=510 for molecular weight of 510.21.

SYNTHESIS EXAMPLE 26

Synthesis of Compound (16-3)

(1) Synthesis of 2-(4-bromo-phenyl)-imidazo [2,1-a] isoquinoline

Almost the same procedure as step (1) in Synthesis Example 23 was carried out except that 1-aminoisoquinoline was used instead of 2-amino-5-picoline, resultantly obtaining 5.1 g of 2-(4-bromo-phenyl)-imidazo [2,1-a] isoquinoline (yield: 88%).

(2) Synthesis of 2-[4-(10-naphthalen-2-yl-anthracen-9-yl)-phenyl]-imidazo [2,1-a] isoquinoline (Compound 16-3)

Almost the same procedure as step (2) in Synthesis Example 13 was carried out except that 2-(4-bromo-phenyl)-imidazo [2,1-a] isoquinoline was used instead of 2-(4-bromo-phenyl)-imidazo [1,2-a] pyridine, resultantly obtaining 2.2 g of yellowish white solids (yield: 72%). As a result of mass spectrum (MS) analysis, the yellowish white solids were identified as the aimed substance (Compound 16-3), and it was recognized that m/e=546 for molecular weight of 546.21.

SYNTHESIS EXAMPLE 27

Synthesis of Compound (16-7)

(1) Synthesis of 2-(4-bromo-phenyl)-imidazo [1,2-a] pyrimidine

Almost the same procedure as step (1) in Synthesis Example 23 was carried out except that 2-aminopyrimidine was used instead of 2-amino-5-picoline, resultantly obtaining 4.1 g of 2-(4-bromo-phenyl)-imidazo [1,2-a] pyrimidine (yield: 83%).

(2) Synthesis of 2-[4-(10-naphthalen-2-yl-anthracen-9-yl)-phenyl]-imidazo [1,2-a] pyrimidine (Compound 16-7)

Almost the same procedure as step (2) in Synthesis Example 13 was carried out except that 2-(4-bromo-phenyl)-imidazo [1,2-a] pyridine was used instead of 2-(4-bromo-phenyl)-imidazo [1,2-a] pyridine, resultantly obtaining 1.7 g of yellowish white solids (yield: 62%). As a result of mass spectrum (MS) analysis, the yellowish white solids were identified as the aimed substance (Compound 16-7), and it was recognized that m/e=497 for molecular weight of 497.19.

SYNTHESIS EXAMPLE 28

Synthesis of Compound (19-1)

(1) Synthesis of 2-(3-bromo-phenyl)-imidazo [1,2-a] pyridine

Dissolving 10 g (50 mmol) of 3'-bromoacetophenone into 20 milliliter of acetic acid and adding 7.0 g (44 mmol) of bromine at the temperature of about 5 to 10° C., stirred at the temperature of about 5 to 10° C. for 4 hours until the color of bromine disappeared. After completion of the reaction, adding water and an extraction was carried out using dichloromethane. Further, washing with water, dried with the use of sodium sulfate. The solvent was removed by distillation and the resultant crude 2,3'-dibromo acetophenone was dissolved into 30 milliliter of ethanol, adding 5.0 g (53 mmol) of 2-aminopyridine and 7.0 g of sodium hydrogen carbonate, the resultant suspension was refluxed under heating for 8 hours. After completion of the reaction, separation with filtration was carried out and resultant crystals were washed with water and methanol, thereby obtaining 3.5 g of 2-(3-bromo-phenyl)-imidazo [1,2-a] pyridine (yield: 26%).

(2) Synthesis of 2-[3-(10-naphthalen-2-yl-anthracen-9-yl)-phenyl]-imidazo [1,2-a] pyridine (Compound 19-1)

Almost the same procedure as step (2) in Synthesis Example 13 was carried out except that 2-(3-bromo-phenyl)-imidazo [1,2-a] pyridine was used instead of 2-(4-bromo-phenyl)-imidazo [1,2-a] pyridine, resultantly obtaining 3.3 g of yellowish white solids (yield: 91%). As a result of mass spectrum (MS) analysis, the yellowish white solids were identified as the aimed substance (Compound 19-1), and it was recognized that m/e=496 for molecular weight of 496.19.

SYNTHESIS EXAMPLE 29

Synthesis of Compound (19-5)

(1) Synthesis of 2-(4'-bromo-biphenyl-4-yl)-imidazo [1,2-a] pyridine

Four point three grams (32 mmol) of aluminum chloride was placed into 30 milliliter of 1,2-dichloroethane and a solution made by dissolving 2.0 g (25 mmol) of acetyl chloride, subsequently 5.0 g (21 mmol) of 4-bromo biphenyl into 20 milliliter of 1,2-dichloroethane was added while cooling with ice. The mixed solution was stirred as it is while cooling with ice for 4 hours. After completion of the reaction, adding water and an extraction was carried out using dichloro-methane. Further, washing with water, dried with the use of sodium sulfate. Removing the solvent by distillation, 5.9 g of crude 1-(4'-bromo-biphenyl-4-yl)-ethanone was obtained.

Dissolving 1-(4'-bromo-biphenyl-4-yl)-ethanone into 20 milliliter of acetic acid and 10 milliliter of tetrachloromethane and adding 3.0 g (19 mmol) of bromine at the temperature of about 5° C., the resultant suspension was stirred at the temperature of about 5 to 10° C. for 3 hours. Then, it was left standing through the night. After completion of the reaction, adding water and an extraction was carried out using dichloro-methane. Further, washing with water, dried with the use of sodium sulfate. The solvent was removed by distillation and white crystals of 2-bromo-1-(4'-bromo-biphenyl-4-yl)-ethanone were obtained in an amount of 6.7 g (yield: 89%).

Dissolving 6.7 g (19 mmol) of 2-bromo-1-(4'-bromo-biphenyl-4-yl)-ethanone into 50 milliliter of ethanol, adding 2.1 g (22 mmol) of 2-aminopyridine and 5.0 g of sodium hydrogen carbonate, the resultant suspension was refluxed under heating for 7 hours. After completion of the reaction, separation with filtration was carried out and resultant crystals were washed with water and methanol, thereby obtaining yellow crystals of 2-(4'-bromo-biphenyl-4-yl)-imidazo [1,2-a] pyridine in an amount of 5.5 g (yield: 84%).

(2) Synthesis of 2-[4'-(10-naphthalen-2-yl-anthracen-9-yl)-biphenyl-4-yl]-imidazo [1,2-a] pyridine (Compound 19-5)

Almost the same procedure as step (2) in Synthesis Example 13 was carried out except that 2-(4'-bromo-biphenyl-4-yl)-imidazo [1,2-a] pyridine was used instead of 2-(4-bromo-phenyl)-imidazo [1,2-a] pyridine, resultantly obtaining 2.6 g of yellowish white solids (yield: 63%). As a result of mass spectrum (MS) analysis, the yellowish white solids were identified as the aimed substance (Compound 19-5), and it was recognized that m/e=572 for molecular weight of 572.23.

SYNTHESIS EXAMPLE 30

Synthesis of Compound (26-8)

(1) Synthesis of 6 bromo-2-phenyl-imidazo [1,2-a] pyridine

Dissolving 5.8 g (29 mmol) of phenacyl bromide and 5.0 g (29 mmol) of 2-amino-5-bromopyridine into 50 milliliter of ethanol, adding 3.6 g of sodium hydrogen carbonate, the resultant suspension was refluxed under heating for 6 hours. After completion of the reaction, separation with filtration was carried out and resultant crystals were washed with water and ethanol, thereby obtaining 6.4 g of 6-bromo-2-phenyl-imidazo [1,2-a] pyridine (yield: 81%).

(2) 6-(10-naphthalen-2-yl-anthracen-9-yl)-2-phenyl-imidazo [1,2-a] pyridine (Compound 26-8)

Dissolving 2.0 g (7.3 mmol) of 6-bromo-2-phenyl-imidazo [1,2-a] pyridine, 2.5 g (11 mmol) of 10-naphthalen-2-yl-anthracene-9-boronic acid and 0.17 g of tetrakis (triphenylphosphine) palladium into 20 milliliter of 1,2-dimethoxyethane, adding 11 milliliter of 2.0M sodium carbonate aqueous solution, the resultant suspension was refluxed under heating for 7 hours. After completion of the reaction, separation with filtration was carried out and resultant crystal were washed with water and methanol, thereby obtaining 2.7 g of yellowish white solids (yield: 75%). As a result of mass spectrum (MS) analysis, the yellowish white solids were identified as the aimed substance, and it was recognized that m/e=496 for molecular weight of 496.19.

SYNTHESIS EXAMPLE 31

Synthesis of Compound (2-7')

(1) Synthesis of 2-(4-bromo-phenyl)-6-phenyl-imidazo [1,2-a] pyridine

Dissolving 5.0 g (29 mmol) of 2-amino-5-bromopyridine, 3.6 g (30 mmol) of phenylboronic acid and 0.67 g of tetrakis (triphenylphosphine) palladium into 90 milliliter of 1,2-dimethoxyethane, adding 45 milliliter of 2.0M sodium carbonate aqueous solution, the resultant suspension was refluxed under heating for 6 hours. After completion of the reaction, the resultant solution was further dissolved into ethyl acetate, filtering the solution, washing with water, dried with the use of sodium sulfate. Removing the solvent by distillation, 4.0 g of crude 5-phenyl-2-amino-pyridine was obtained.

Dissolving crude 5-phenyl-2-amino-pyridine obtained and 6.5 g (23 mmol) of 2,4'-dibromo acetophenone into 50 milliliter of ethanol, adding 3.7 g of sodium hydrogen carbonate, the resultant suspension was refluxed under heating for 6 hours. After completion of the reaction, separation with filtration was carried out and resultant crystals were washed with water and methanol, thereby obtaining 3.1 g of 2-(4-bromo-phenyl)-6-phenyl-imidazo [1,2-a] pyridine (yield: 31%).

(2) Synthesis of 2-[4-(10-naphthalen-2-yl-anthracen-9-yl)-phenyl]-6-phenyl-imidazo [1,2-a] pyridine (Compound 2-7')

Dissolving 4.0 g (11 mmol) of 2-(4-bromo-phenyl)-6-phenyl-imidazo [1,2-a] pyridine, 4.0 g (11 mmol) of 10-naphthalen-2-yl-anthracene-9-boronic acid and 0.27 g of tetrakis (triphenylphosphine) palladium into 40 milliliter of 1,2-dimethoxyethane, adding 18 milliliter of 2.0M sodium carbonate aqueous solution, the resultant suspension was refluxed under heating for 7 hours. After completion of the reaction, separation with filtration was carried out and resultant crystals were washed with water and methanol, thereby obtaining 4.9 g of yellowish white solids (yield: 76%). As a result of mass spectrum (MS) analysis, it was recognized that m/e=572 for molecular weight of 572.23 and the yellowish white solids were identified as the aimed substance.

SYNTHESIS EXAMPLE 32

Synthesis of Compound (3-3')

(1) Synthesis of 2-(4-bromo-phenyl)-6-biphenyl-2-yl-imidazo [1,2-a] pyridine

Almost the same procedure as step (1) in Synthesis Example 31 was carried out except that 2-biphenyl boronic acid was used instead of phenylboronic acid, resultantly obtaining 4.0 g of 2-(4-bromo-phenyl)-6-biphenyl-2-yl-imidazo [1,2-a] pyridine (yield: 54%).

(2) Synthesis of 2-[4-(10-naphthalen-2-yl-anthracen-9-yl)-phenyl]-6-biphenyl-2-yl-imidazo [1,2-a] pyridine (Compound 3-3')

Almost the same procedure as step (2) in Synthesis Example 31 was carried out except that 2-(4-bromo-phenyl)-6-biphenyl-2-yl-imidazo [1,2-a] pyridine was used instead of 2-(4-bromo-phenyl)-6-phenyl-imidazo [1,2-a] pyridine, resultantly obtaining 3.7 g of yellowish white solids (yield: 91%). As a result of mass spectrum (MS) analysis, it was recognized that m/e=648 for molecular weight of 648.26 and the yellowish white solids were identified as the aimed substance.

SYNTHESIS EXAMPLE 33

Synthesis of Compound (3-4')

(1) Synthesis of 2-(4-bromo-phenyl)-6-[1,1';3',1"] terphenyl-5'-yl-imidazo [1,2-a] pyridine Almost the same procedure as step (1) in Synthesis Example 31 was carried out except that [1,1';3',1"] terphenyl boronic acid was used instead of phenylboronic acid, resultantly obtaining 6.3 g of 2-(4-bromo-phenyl)-6-[1,1';3',1"] terphenyl-5'-yl-imidazo [1,2-a] pyridine (yield: 73%).

(2) Synthesis of 2-[4-(10-naphthalen-2-yl-anthracen-9-yl)-phenyl]-6-[1,1';3',1"] terphenyl-5'-yl-imidazo [1,2-a] pyridine (Compound 3-4 ')

Almost the same procedure as step (2) in Synthesis Example 31 was carried out except that 2-(4-bromo-phenyl)-6-[1,1';3',1"] terphenyl-5'-yl-imidazo [1,2-a] pyridine was used instead of 2-(4-bromo-phenyl)-6-phenyl-imidazo [1,2-a] pyridine, resultantly obtaining 2.8 g of yellowish white solids (yield: 69%). As a result of mass spectrum (MS) analysis, it was recognized that m/e=724 for molecular weight of 724.29 and the yellowish white solids were identified as the aimed substance.

SYNTHESIS EXAMPLE 34

Synthesis of Compound (3-5')

(1) Synthesis of 2-(4-bromo-phenyl)-6-naphthalen-1-yl-imidazo [1,2-a] pyridine

Almost the same procedure as step (1) in Synthesis Example 31 was carried out except that 1-naphthalene boronic acid was used instead of phenylboronic acid, resultantly obtaining 9.2 g of 2-(4-bromo-phenyl)-6-naphthalen-1-yl-imidazo [1,2-a] pyridine (yield: 80%).

(2) Synthesis of 2-[4-(10-naphthalen-2-yl-anthracen-9-yl)-phenyl]-6-naphthalen-1-yl-imidazo [1,2-a] pyridine (Compound 3-5')

Almost the same procedure as step (2) in Synthesis Example 31 was carried out except that 2-(4-bromo-phenyl)-6-naphthalen-1-yl-imidazo [1,2-a] pyridine was used instead of 2-(4-bromo-phenyl)-6-phenyl-imidazo [1,2-a] pyridine, resultantly obtaining 4.3 g of yellowish white solids (yield: 90%). As a result of mass spectrum (MS) analysis, it was recognized that m/e=622 for molecular weight of 622.24 and the yellowish white solids were identified as the aimed substance.

SYNTHESIS EXAMPLE 35

Synthesis of Compound (3-6')

(1) Synthesis of 2-(4-bromo-phenyl)-6-naphthalen-2-yl-imidazo [1,2-a] pyridine

Almost the same procedure as step (1) in Synthesis Example 31 was carried out except that 2-naphthalene boronic acid was used instead of phenylboronic acid, resultantly obtaining 9.9 g of 2-(4-bromo-phenyl)-6-naphthalen-1-yl-imidazo [1,2-a] pyridine (yield: 86%).

(2) Synthesis of 2-[4-(10-naphthalen-2-yl-anthracen-9-yl)-phenyl]-6-naphthalen-2-yl-imidazo [1,2-a] pyridine (Compound 3-6')

Almost the same procedure as step (2) in Synthesis Example 31 was carried out except that 2-(4-bromo-phenyl)-6-naphthalen-2-yl-imidazo [1,2-a] pyridine was used instead of 2-(4-bromo-phenyl)-6-phenyl-imidazo [1,2-a] pyridine, resultantly obtaining 3.6 g of yellowish white solids (yield: 83%). As a result of mass spectrum (MS) analysis, it was recognized that m/e=622 for molecular weight of 622.24 and the yellowish white solids were identified as the aimed substance.

SYNTHESIS EXAMPLE 36

Synthesis of Compound (3-7')

(1) Synthesis of 2-(4-bromo-phenyl)-6-phenanthrene-9-yl-imidazo [1,2-a] pyridine Almost the same procedure as step (1) in Synthesis Example 31 was carried out except that 9-phenantharene boronic acid was used instead of phenylboronic acid, resultantly obtaining 7.3 g of 2-(4-bromo-phenyl)-6-naphthalene-9-yl-imidazo [1,2-a] pyridine (yield: 95%).

(2) Synthesis of 2-[4-(10-naphthalen-2-yl-anthracen-9-yl)-phenyl]-6-phenanthrene-9-yl-imidazo [1,2-a] pyridine (Compound 3-7')

Almost the same procedure as step (2) in Synthesis Example 31 was carried out except that 2-(4-bromo-phenyl)-6-phenanthrene-9-yl-imidazo [1,2-a] pyridine was used instead of 2-(4-bromo-phenyl)-6-phenyl-imidazo [1,2-a] pyridine, resultantly obtaining 2.7 g of yellowish white solids (yield: 73%). As a result of mass spectrum (MS) analysis, it was recognized that m/e=672 for molecular weight of 672.26 and the yellowish white solids were identified as the aimed substance.

SYNTHESIS EXAMPLE 37

Synthesis of Compound (7-8')

(1) Synthesis of 2-(4-bromo-phenyl)-6,8-diphenyl-imidazo [1,2-a] pyridine

Dissolving 5.0 g (20 mmol) of 2-amino-3,5-dibromo pyridine, 5.0 g (41 mmol) of phenylboronic acid and 0.92 g of tetrakis (triphenylphosphine) palladium into 130 milliliter of 1,2-dimethoxyethane, adding 62 milliliter of 2.0M sodium carbonate aqueous solution, the resultant suspension was refluxed under heating for 6 hours. After completion of the reaction, the resultant solution was further dissolved into ethyl acetate, filtering the solution, washing with water, dried with the use of sodium sulfate. Removing the solvent by distillation, 8.9 g of crude 3,5-diphenyl-2-amino-pyridine was obtained.

Dissolving crude 3,5-diphenyl-2-amino-pyridine obtained and 5.5 g (20 mmol) of 2,4'-dibromo acetophenone into 80 milliliter of ethanol, adding 3.0 g of sodium hydrogen carbonate, the resultant suspension was refluxed under heating for 7 hours. After completion of the reaction, separation with filtration was carried out and resultant crystals were washed with water and methanol, thereby obtaining 6.9 g of 2-(4-bromo-phenyl)-6-phenyl-imidazo [1,2-a] pyridine (yield: 82%).

(2) Synthesis of 2-[4-(10-naphthalen-2-yl-anthracen-9-yl)-phenyl]-6,8-diphenyl-imidazo [1,2-a] pyridine (Compound 7-8')

Almost the same procedure as step (2) in Synthesis Example 31 was carried out except that 2-(4-bromo-phenyl)-6,8-diphenyl-imidazo [1,2-a] pyridine was used instead of 2-(4-bromo-phenyl)-6-phenyl-imidazo [1,2-a] pyridine, resultantly obtaining 3.2 g of yellowish white solids (yield: 86%). As a result of mass spectrum (MS) analysis, it was recognized that m/e=648 for molecular weight of 648.26 and the yellowish white solids were identified as the aimed substance.

SYNTHESIS EXAMPLE 38

Synthesis of Compound (9-7')

(1) Synthesis of 2-(4-bromo-phenyl)-6-phenyl-imidazo [1,2-a] pyrimidine

Dissolving 5.5 g (32 mmol) of 2-amino-5-bromopyridine, 4.3 g (32 mmol) of phenylboronic acid and 0.80 g of tetrakis (triphenylphosphine) palladium into 100 milliliter of 1,2-dimethoxyethane, adding 50 milliliter of 2.0M sodium carbonate aqueous solution, the resultant suspension was refluxed under heating for 8 hours. After completion of the reaction and after filtration of the solution, washing the organic layer with water, dried it with the use of sodium sulfate. Removing the solvent by distillation, 6.2 g of crude 5-phenyl-2-amino-pyridine was obtained.

Dissolving crude 5-phenyl-2-amino-pyridine obtained and 8.0 g (29 mmol) of 2,4'-dibromo acetophenone into 100 milliliter of ethanol, adding 3.7 g of sodium hydrogen carbonate, the resultant suspension was refluxed under heating for 3 hours. After completion of the reaction, separation with filtration was carried out and resultant crystals were washed with water and methanol, thereby obtaining 5.4 g of 2-(4-bromo-phenyl)-6-phenyl-imidazo [1,2-a] pyridine (yield: 49%).

(2) Synthesis of 2-[4-(10-naphthalen-2-yl-anthracen-9-yl)-phenyl]-6-phenyl-imidazo [1,2-a] pyrimidine (Compound 9-7')

Dissolving 3.0 g (8.6 mmol) of 2-(4-bromo-phenyl)-6-phenyl-imidazo [1,2-a] pyridine, 3.0 g (8.6 mmol) of 10-naphthalen-2-yl-anthracene-9-boronic acid and 0.20 g of tetrakis (triphenylphosphine) palladium into 30 milliliter of 1,2-dimethoxyethane, adding 13 milliliter of 2.0M sodium carbonate aqueous solution, the resultant suspension was refluxed under heating for 7 hours. After completion of the reaction, separation with filtration was carried out and resultant crystals were washed with water, methanol and toluene, thereby obtaining 3.0 9 g of yellowish white solids (yield: 62%). As a result of mass spectrum (MS) analysis, it was recognized that m/e=573 for molecular weight of 573.22 and the yellowish white solids were identified as the aimed substance.

EXAMPLE 1

Preparation of the Organic EL Device Employing the Compound of the Present Invention in an Electron Injecting Layer A glass substrate (manufactured by GEOMATEC Company) with a dimension of 25 mm×75 mm and 1.1 mm in thickness having an ITO transparent electrode was cleaned by application of ultrasonic wave in isopropyl alcohol for 5 minutes and then by exposure to ozone generated by ultraviolet light for 30 minutes. The glass substrate having the transparent electrode line which had been cleaned was adhered to a substrate holder of a vacuum vapor deposition apparatus. On the surface of the cleaned substrate at the side having the transparent electrode line, a film of N,N'-bis (N,N'-diphenyl-4-aminophenyl)-N,N-diphenyl-4,4'-diamino-1,1'-biphenyl (referred to as a "film of TPD232", hereinafter) having a thickness of 60 nm was formed in accordance with the resistance heating deposition method in a manner such that the formed film covered the transparent electrode. The formed film of TPD232 worked as the hole injecting layer. Subsequent to the film-forming of the film of TPD232, a film of 4,4'-bis [N-(1-naphthyl)-N-phenylamino] biphenyl (referred to as a "film of NPD", hereinunder) having a thickness of 20 nm was formed over the film of TPD232 in accordance with the resistance heating deposition method. The formed film of NPD worked as the second hole injecting layer (or hole transporting layer). Over the formed film of NPD, 4',4"-bis(2,2-diphenylvinyl)-9,10-biphenylanthracene (referred to as “DPVDPAN”, hereinafter) having a thickness of 40 nm was further formed in accordance with the resistance heating deposition method. The formed film of DPVDPAN worked as the light emitting layer. Subsequent to the film-forming of the film of DPVDPAN, a film of Compound (1-3) of the present invention having a thickness of 10 nm was formed over the film of DPVDPAN in accordance with the resistance heating deposition method. The formed film of the compound (1-3) worked as the electron injecting layer. Thereafter, Li (the source of lithium: produced by SAES GETTERS Company) was binary vapor deposited and Compound (1-3):Li film having a thickness of 10 nm was formed as the electron injecting layer (or, the cathode) with the film-forming rate of 1.6 Å/second: 1 Å/minute. On the formed compound (1-3): Li film, metallic aluminum having the film thickness of 130 nm was vapor deposited to form a metal cathode and an organic EL device was prepared.

EXAMPLES 2 to 15

Organic EL devices were prepared in similar manners as Example 1 except that compounds described in Table 1 were employed instead of Compound (1-3).

COMPARATIVE EXAMPLE 1

An organic EL device was prepared in a similar manner as Example 1 except that Alq (aluminum complex of 8-hydroxyquinoline) was employed instead of Compound (1-3).

Evaluation of the Organic EL Device

The organic EL devices prepared in Examples 1 to 15 and in Comparative Example 1 were subjected to measurements of luminance and current efficiency while applying DC voltages described in Table 1 below. The evaluated results are shown in Table 1.

TABLE 1

| | Compound in electron injecting layer | Voltage (V) | Current Density ($mA/cm^2$) | Luminance (nit) | Current efficiency (cd/A) |
|---|---|---|---|---|---|
| Ex. 1 | Compound 1-3 | 7.5 | 3.09 | 119 | 3.85 |
| Ex. 2 | Compound 1-4 | 6.0 | 4.39 | 237 | 5.40 |
| Ex. 3 | Compound 14-7 | 3.7 | 7.74 | 532 | 6.87 |
| Ex. 4 | Compound 14-1 | 3.0 | 2.00 | 127 | 6.40 |
| Ex. 5 | Compound 14-2 | 3.0 | 2.10 | 146 | 7.10 |
| Ex. 6 | Compound 14-6 | 3.3 | 1.90 | 139 | 7.30 |
| Ex. 7 | Compound 14-9 | 4.2 | 2.60 | 150 | 5.80 |
| Ex. 8 | Compound 15-1 | 3.0 | 1.40 | 93 | 6.80 |
| Ex. 9 | Compound 15-3 | 3.5 | 3.30 | 242 | 7.40 |
| Ex. 10 | Compound 15-4 | 3.5 | 4.60 | 330 | 7.20 |
| Ex. 11 | Compound 15-5 | 3.5 | 3.00 | 222 | 7.40 |
| Ex. 12 | Compound 16-3 | 3.5 | 2.70 | 200 | 7.50 |
| Ex. 13 | Compound 19-1 | 3.0 | 1.70 | 123 | 7.30 |
| Ex. 14 | Compound 19-5 | 4.0 | 2.20 | 137 | 6.20 |
| Ex. 15 | Compound 26-8 | 4.8 | 3.40 | 178 | 5.30 |
| Co. Ex. 1 | Alq | 6.0 | 5.20 | 190 | 3.75 |

From the results in the above Table 1, it is verified that employing the above compounds of the present invention as the electron injecting material enables to produce the organic EL device with extremely high current efficiency.

EXAMPLE 16

Preparation of the Organic EL Device Employing the Compounds of the Present Invention in a Light Emitting Layer A glass substrate (manufactured by GEOMATEC Company) with a dimension of 25 mm×75 mm and 1.1 mm in thickness having an ITO transparent electrode was cleaned by application of ultrasonic wave in isopropyl alcohol for 5 minutes and then by exposure to ozone generated by ultraviolet light for 30 minutes. The glass substrate having the transparent electrode line which had been cleaned was adhered to a substrate holder of a vacuum vapor deposition apparatus. On the surface of the cleaned substrate at the side having the transparent electrode line, a film of TPD232 having a thickness of 60 nm was formed in accordance with the resistance heating deposition method in a manner such that the formed film covered the transparent electrode. The formed film of TPD232 worked as the first hole injecting layer (hole transporting layer). Subsequent to the film-forming of TPD232, a film of the foregoing NPD having a thickness of 20 nm was formed over the formed film of TPD232 in accordance with the resistance heating deposition method. The formed film of NPD worked as the second hole injecting layer (hole transporting layer). Subsequent to the film-forming of the film of NPD, a film of Compound (14-7) of the present invention having a thickness of 40 nm was further formed over the film of NPD in accordance with the resistance heating deposition method. The formed film of compound (14-7) worked as the light emitting layer. Thereafter, Li (the source of lithium: produced by SAES GETTERS Company) was binary vapor deposited and Compound (14-7): Li film having a thickness of 20 nm was formed as the electron injecting layer (or, the cathode) with the film-forming rate of 1.6 Å/second: 1Å/minute. On the formed compound (14-7): Li film, metallic aluminum was vapor deposited to form a metal cathode and an organic EL device was prepared. When a direct current voltage of 4.6 V was applied to the organic EL device prepared above, bluish green light was emitted at a luminance of 1030 $cd/m^2$ and current efficiency of 3.05 cd/A.

EXAMPLE 17

Organic EL devices were prepared in a similar manner as Example 16 except that Compound (1-3) obtained in Synthesis Example was employed instead of Compound (14-7).

Evaluation of the Organic EL Device

The organic EL devices prepared in the above Examples 16 and 17 were subjected to measurements of luminance, current efficiency and chromaticity while applying DC voltages described in Table 2 below. The evaluation results are shown in Table 2.

TABLE 2

| | Compound in light emitting layer | Voltage (V) | Current Density (mA/cm²) | Luminance (nit) | Current efficiency (cd/A) | Chromaticity |
|---|---|---|---|---|---|---|
| Ex. 16 | Compound 14-7 | 4.6 | 33.80 | 1,030 | 3.05 | (0.186, 0.212) |
| Ex. 17 | Compound 1-3 | 6.5 | 4.80 | 103 | 2.15 | (0.229, 0.325) |

From the results in the above Table 2, it is verified that the foregoing compounds employed even as a light emitting layer reveals enough effect.

EXAMPLE 18

An organic EL device was prepared in a similar manner as Example 1 except that Compound (2-7') was used instead of Compound (1-3) and that a film of Compound (2-7'): Li film having a thickness of 10 nm was formed as an electron injecting layer or a cathode with a film-forming rate of 1.5 Å/second: 1 Å/min.

The organic EL device thus, prepared was subjected to measurements of luminance, current efficiency and chromaticity while applying voltages and current densities described in Table 3 below. The results and color of emitted light are shown in Table 3.

EXAMPLES 19 TO 21

Preparation of the Organic EL Device Employing the Compounds of the Present Invention in an Electron Injecting Layer Organic EL devices were prepared in similar manners as Example 18 except that compounds described in Table 3 were employed instead of Compound (2-7').

The organic EL device thus prepared was subjected to measurements of luminance, current efficiency and chromaticity while applying voltages and current densities described in Table 3 below. The results and color of emitted light are shown in Table 3.

COMPARATIVE EXAMPLE 2

Preparation of the Organic EL Device

An organic EL device was prepared in a similar manner as Example 18 except that aluminum complex of 8-hydroxyquinoline (Alq) was employed instead of Compound (2-7').

The organic EL device thus prepared was subjected to measurements of luminance, current efficiency and chromaticity while applying voltages and current densities described in Table 3 below. The results and color of emitted light are shown in Table 3.

COMPARATIVE EXAMPLE 3

Preparation of the Organic EL Device

Organic EL devices was prepared in a similar manner as Example 18 except that Compound A below that is described in Japanese Unexamined Patent Application Laid Open No. 2001-6887 was employed instead of Compound (2-7').

The organic EL device thus prepared was subjected to measurements of luminance, current efficiency and chromaticity while applying voltages and current densities described in Table 3 below. The results and color of emitted light are shown in Table 3.

TABLE 3

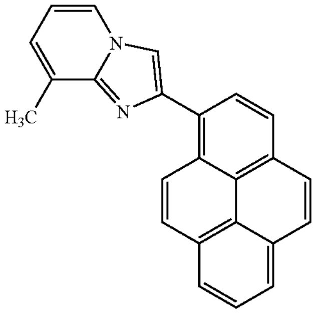

Compound A

| | Kind of electron injecting layer | Voltage (V) | Current Density (mA/cm²) | Luminance (nit) | Current efficiency (cd/A) | Chromaticity | Color of light emission |
|---|---|---|---|---|---|---|---|
| Ex. 18 | Compound 2–7' | 3.8 | 2.8 | 192 | 6.8 | (0.146, 0.157) | Blue |
| Ex. 19 | Compound 3–5' | 3.8 | 3.1 | 208 | 6.6 | (0.144, 0.152) | Blue |
| Ex. 20 | Compound 3–6' | 4.0 | 2.5 | 150 | 6.1 | (0.147, 0.161) | Blue |
| Ex. 21 | Compound 7–8' | 3.3 | 2.2 | 167 | 7.4 | (0.150, 0.170) | Blue |
| Co. Ex. 2 | Alq | 6.0 | 5.2 | 190 | 3.8 | (0.149, 0.164) | Blue |
| Co. Ex. 3 | Compound A | 7.0 | 3.2 | 135 | 4.2 | (0.144, 0.144) | Blue |

As shown in Table 3, the organic EL devices prepared in Examples 18 to 21 employing hetero cyclic derivatives containing nitrogen atom of the present invention as an electron injecting material exhibit excellent luminance and current efficiency respectively even under applying very lower voltage than Comparative Example 2 and 3.

INDUSTRIAL APPLICABILITY

The present invention provides an organic EL device achieving elevation of luminance and excellent efficiency of light emission even under low driving voltage, and also achieving long term stabilization by improvement of an electrode adhesion in accordance with an employment of the derivative of heterocyclic compound having nitrogen atom for at least one layer composing organic compound layers of the EL device.

What is claimed is:

1. A derivative of heterocyclic compound having nitrogen atom represented by general formula (1):

$$HAr\text{-}L\text{-}Ar^1—Ar^2 \quad (1)$$

wherein HAr is one of the following groups:

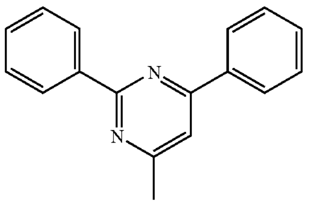

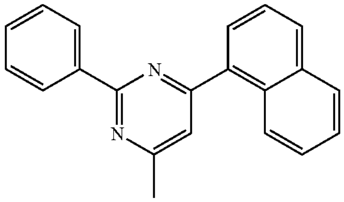

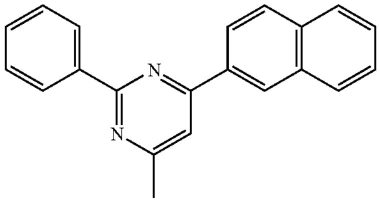

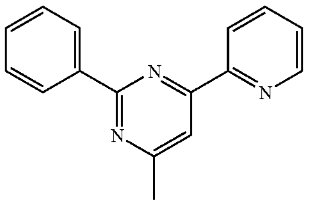

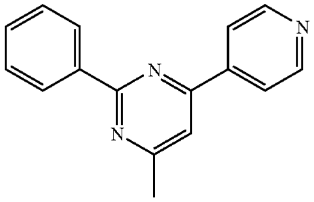

-continued

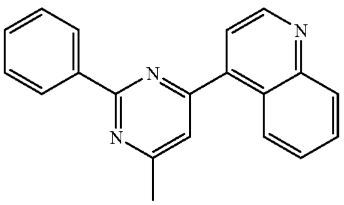

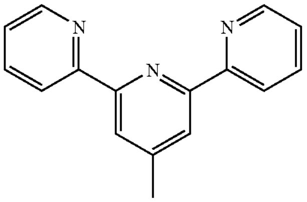

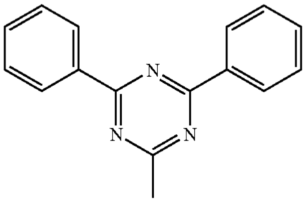

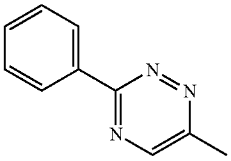
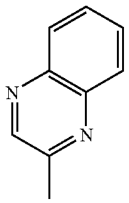
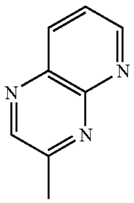

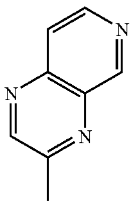
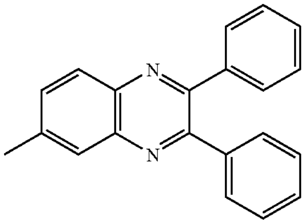

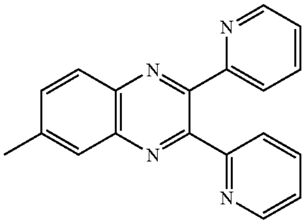

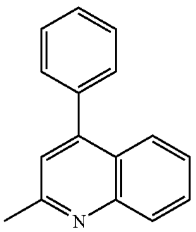
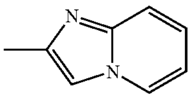

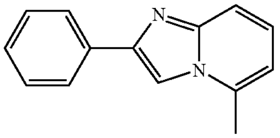

-continued
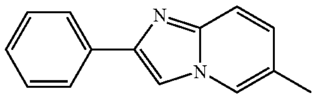
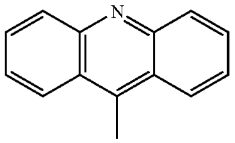
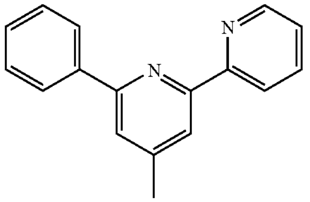
L represents a single bond, an arylene group having 6 to 60 carbon atoms and may have a substituent, a heteroarylene group having 3 to 60 carbon atoms and may have a substituent or a fluorenylene group which may have a substituent;
$Ar^1$ represents a divalent aromatic hydrocarbon group represented by one of general formulae (43) to (54):
(43)
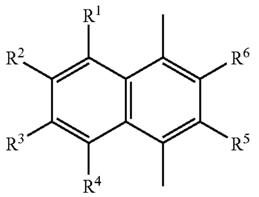
(44)
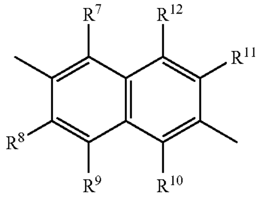
(45)
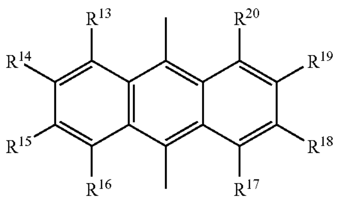
(46)
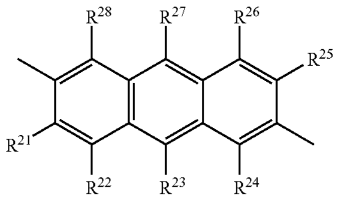
-continued
(47)
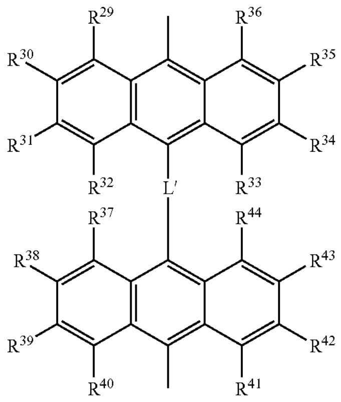
(48)
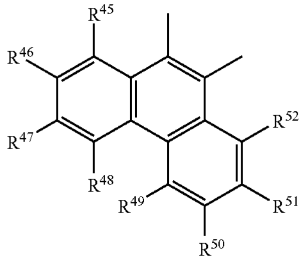
(49)
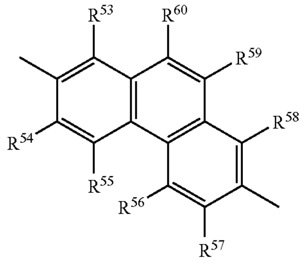
(50)
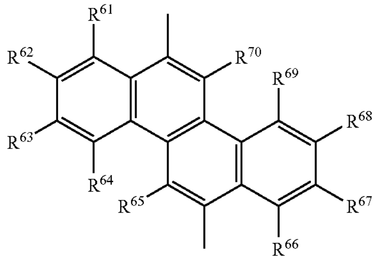
(51)
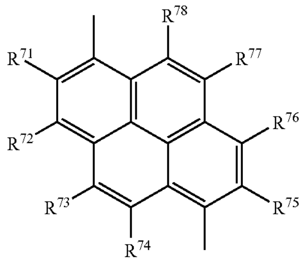

-continued (52)

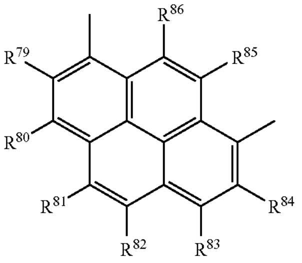

(53)

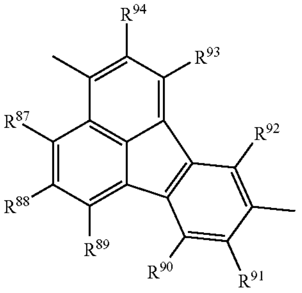

(54)

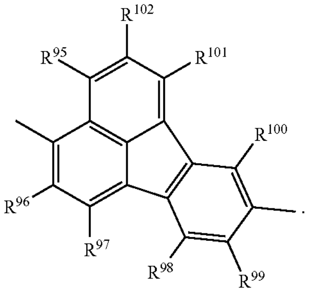

wherein $R^1$ to $R^{102}$ each independently represents a hydrogen atom, a halogen atom, an alkyl group having 1 to 20 carbon atoms and may have a substituent, an alkoxyl group having 1 to 20 carbon atoms and may have a substituent, an aryloxyl group having 6 to 40 carbon atoms and may have a substituent, a diarylamino group having 12 to 80 carbon atoms and may have a substituent, an aryl group having 6 to 40 carbon atoms and may have a substituent, a heteroaryl group having 3 to 40 carbon atoms and may have a substituent, or a diarylamino group having 18 to 120 carbon atoms and may have a substituent; and L' represents a single bond or a group selected from the following groups:

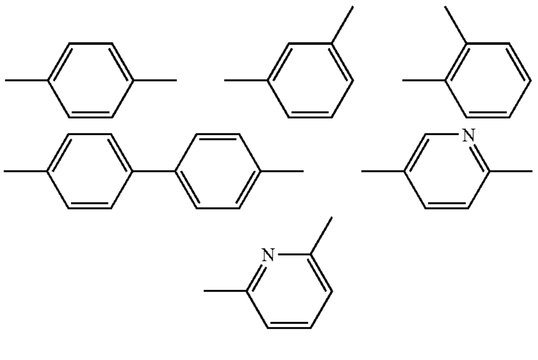

-continued

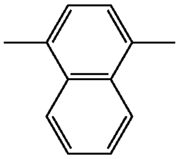

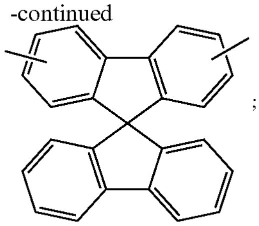

; and $Ar^2$ represents an aryl group which may optionally be substituted, wherein $Ar^2$ is one of the following groups:

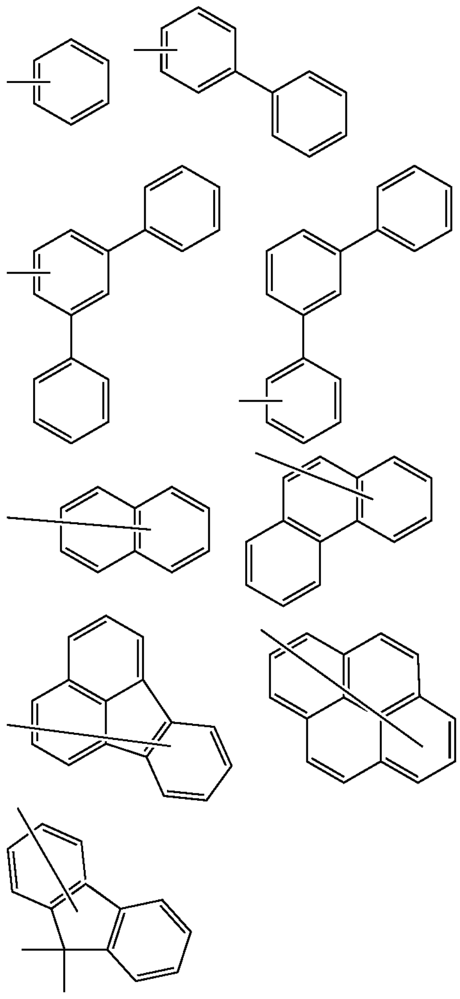

and the optional substituent to $Ar^2$ is selected from the group consisting of a halogen atom, a substituted or unsubstituted alkyl group having 1 to 20 carbon atoms, a substituted or unsubstituted alkoxyl group having 1 to 20 carbon atoms, a substituted or unsubstituted aryloxyl group having 6 to 40 carbon atoms, a substituted or unsubstituted diarylamino group having 12 to 80 carbon atoms, and a substituted or unsubstituted aryl group having 6 to 40 carbon atoms.

2. The derivative of heterocyclic compound having nitrogen atom according to claim 1, wherein L represents an arylene group having 6 to 60 carbon atoms and may have a substituent, a heteroarylene group having 3 to 60 carbon atoms and may have a substituent or a fluorenylene group which may have a substituent.

3. The derivative of heterocyclic compound having nitrogen atom according to claim 1, wherein L represents a single bond.

4. The derivative of heterocyclic compound having nitrogen atom according to claim 1, wherein L is any one group selected from the following groups:

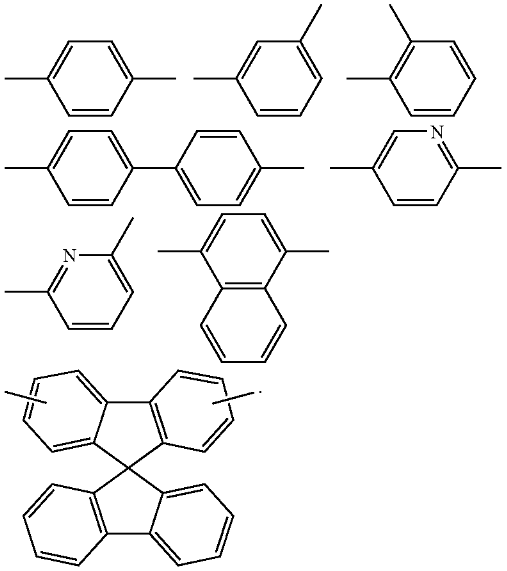

5. The derivative of heterocyclic compound having nitrogen atom according to claim 1, wherein the substituent for $Ar^2$ is an alkyl group having 1 to 6 carbon atoms.

6. An organic electroluminescence device comprising the derivative of heterocyclic compound having nitrogen atom according to claim 1.

7. An organic electroluminescence device comprising at least one organic compound layer containing a light emitting layer sandwiched between a pair of electrodes, wherein the device contains the derivative of heterocyclic compound having nitrogen atom according to claim 1 among the compound layer.

8. The organic electroluminescence device according to claim 7, wherein said derivative of heterocyclic compound having nitrogen atom is contained in a light emission area.

9. The organic electroluminescence device according to claim 7, wherein said derivative of heterocyclic compound having nitrogen atom is contained in the light emitting layer.

10. The organic electroluminescence device according to claim 7, wherein said derivative of heterocyclic compound having nitrogen atom is employed for at least one of an electron injection material and an electron transport material.

11. The organic electroluminescence device according to claim 10, wherein a layer comprising said at least one of the electron injection material and the electron transport material further comprises a reductive dopant.

12. The organic electroluminescence device according to claim 11, wherein said reductive dopant is at least one selected from the group consisting of alkali metal, alkaline earth metal, rare earth metal, oxide of alkali metal, halide of alkali metal, oxide of alkaline earth metal, halide of alkaline earth metal, oxide of rare earth metal, halide of rare earth metal, organic complexes of alkali metal, organic complexes of alkaline earth metal and organic complexes of rare earth metal.

* * * * *